US009233960B2

(12) United States Patent
Hergenrother et al.

(10) Patent No.: US 9,233,960 B2
(45) Date of Patent: Jan. 12, 2016

(54) COMPOUNDS AND ANTI-TUMOR NQO1 SUBSTRATES

(71) Applicants: Paul J. Hergenrother, Champaign, IL (US); David A. Boothman, Dallas, TX (US); Joseph S. Bair, Albany, CA (US); Rahul Palchaudhuri, Cambridge, MA (US); Elizabeth I. Parkinson, Champaign, IL (US)

(72) Inventors: Paul J. Hergenrother, Champaign, IL (US); David A. Boothman, Dallas, TX (US); Joseph S. Bair, Albany, CA (US); Rahul Palchaudhuri, Cambridge, MA (US); Elizabeth I. Parkinson, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 14/351,861

(22) PCT Filed: Oct. 12, 2012

(86) PCT No.: PCT/US2012/059988
§ 371 (c)(1),
(2) Date: Apr. 14, 2014

(87) PCT Pub. No.: WO2013/056073
PCT Pub. Date: Apr. 18, 2013

(65) Prior Publication Data
US 2015/0011509 A1 Jan. 8, 2015

Related U.S. Application Data

(60) Provisional application No. 61/547,166, filed on Oct. 14, 2011, provisional application No. 61/662,163, filed on Jun. 20, 2012.

(51) Int. Cl.
| | | |
|---|---|---|
| C07D 471/00 | (2006.01) |
| A61K 31/675 | (2006.01) |
| C07D 471/04 | (2006.01) |
| A61K 31/47 | (2006.01) |
| C07H 15/26 | (2006.01) |
| C07F 9/6561 | (2006.01) |

(52) U.S. Cl.
CPC ............. C07D 471/04 (2013.01); A61K 31/47 (2013.01); C07F 9/6561 (2013.01); C07H 15/26 (2013.01)

(58) Field of Classification Search
None
See application file for complete search history.

(56) References Cited

U.S. PATENT DOCUMENTS

| 4,906,562 A | 3/1990 | Hellstrom et al. |
| 5,716,963 A | 2/1998 | Avendano Lopez et al. |

FOREIGN PATENT DOCUMENTS

| WO | 2012040492 A1 * | 3/2012 | ............. A61K 31/22 |
| WO | 2012085532 A2 | 6/2012 | |

OTHER PUBLICATIONS

Tudor, G. et al Biochem Pharmacol 2003 vol. 65 pp. 1061-1075.*
CAPLUS 2000:458475.*
Pettit, G. et al J. Nat. Prod. 2006 vol. 69 pp. 804-806.*
Chu Bioorg Med Chem Lett 2003 pp. 3827-3829.*
CAPLUS 1996 80360.*
Bair, Joseph S. et al., "Chemistry and Biology of Deoxynyboquinone, a Potent Inducer of Cancer Cell Death", J. Am. Chem. Soc. 2010, 132, 5469-5478.
Huang, Xuimei et al., "An NQO1 Substrate with Potent Antitumor Activity That 3 Q1 Selectively Kills by PARP1-Induced Programmed Necrosis", American Association for Cancer Research, 2012, 11 pp.
International Search Report and Written Opinion for PCT/US12/59988 dated Dec. 24, 2012, 7 pp.
Lee, Heesoon et al., "Total Synthesis of 4-Acetyloxynnethyl-1,6,9-triniethyl-1, 9-diazaanthracene-2,5,8,10-tetraone, A Nybomycin Acetate Analogue", Tetrahedron Letters, vol. 31, No. 31, May 23, 1990, pp. 4405-4408.
Li, Long Shan et al., "Modulating Endogenous NQO1 Levels Identifies Key Regulatory Mechanisms of Action of B-Lapachone for Pancreatic Cancer Therapy", American Association for Cancer Research, published online Jan. 11, 2011, pp. 275-285.
Tudor, Gabriela et al., "Cytotoxicity and apoptosis of benzoquinones: redox cycling, cytochrome c release, and BAD protein expression", Biochemical Pharmacology 65 (2003), 1061-1075.
Diaz-Guerra, Luis M. et al., "Half-Wave Potentials of 1-Aza and 1,8-Diazaanthraquinones," CAPLUS, Jan. 1, 1995, XP002480321.
European Search Report corresponding to related European Application No. 12840771.5.
Perez, Jose et al., "Concise Preparation of 1,8-Diazaanthracene-2,7,9,10-Tetraones. Two Alternative Syntheses of the Natural Antifolate Diazaquinomycin A," Tetrahedron 56 (2000) 4575-4583.

* cited by examiner

*Primary Examiner* — Heidi Reese
(74) *Attorney, Agent, or Firm* — Haukaas Fortius PLLC; Michael H. Haukaas

(57) ABSTRACT

Compounds of Formula (I) can be selectively lethal toward a variety of different cancer cell types. The compounds are useful for the management, treatment, control, or adjunct treatment of diseases, where the selective lethality is beneficial in chemotherapeutic therapy.

20 Claims, 14 Drawing Sheets

10--41

9-255

9-257

2--99

2--97

DNQ_d-3

2--77

2--103

COMPOUNDS AND ANTI-TUMOR NQO1 SUBSTRATES

GOVERNMENT SUPPORT

This invention was made with government support under contract number CA102792 awarded by the National Institutes of Health. The government has certain rights in the invention.

RELATED APPLICATIONS

This application is a national stage filing under 35 U.S.C. §371 of PCT/US2012/059988, filed Oct. 12, 2012, which claims priority to U.S. Provisional Patent Application Nos. 61/547,166 filed Oct. 14, 2011 and 61/662,163 filed Jun. 20, 2012, which applications are incorporated herein by reference in their entireties.

BACKGROUND OF THE INVENTION

A fundamental challenge in cancer treatment is the discovery of compounds that are toxic to cancer cells but not healthy cells. A salient feature of cancer is rapid and unrestricted cell division. The vast majority of traditional chemotherapeutics target rapidly dividing cells by disrupting the cell cycle, causing cell death. Because some healthy tissues require cell division as part of their function, antiproliferative cytotoxins can also kill healthy cells, resulting in severe, dose-limiting side effects. Accordingly, new drugs and new cellular targets must be identified that better differentiate healthy and cancerous cells. These targets may be present in only a small fraction of cancer patients, making this a personalized strategy to treat cancer.

NAD(P)H quinone oxidoreductase (NQO1, DT diaphorase) is an FAD-dependent 2-electron reductase whose primary function is to protect the cell from cytotoxins, especially quinones. It is a member of the Phase II detoxifying enzymes, the expression of which is regulated by NRF-2 and the antioxidant response element (ARE) in response to electrophilic or oxidative stress. Although generally identified as a cytosolic protein, NQO1 has been identified in subcellular compartments such as the mitochondria and nucleus.

Quinone-containing molecules are frequently cytotoxic and harm cells through two mechanisms. Many quinones are conjugate addition acceptors and readily alkylate nucleophilic species such as DNA and cysteine residues. Quinones are also substrates for 1-electron reductases, such as cytochrome P450s, cytochrome b5, xanthine oxidase, and glutathione reductase. Reduction of quinones by these enzymes generates a highly reactive semiquinone that can damage biomolecules directly, or can be oxidized by dissolved oxygen resulting in the formation of an equivalent of superoxide anion radical and the parent quinone. Thus, 1-electron reduction of quinones can catalytically create reactive oxygen species (ROS) that damage the cell.

By reducing quinones in a 2-electron process, NQO1 bypasses the toxic semiquinone and forms hydroquinones, which are commonly unreactive toward oxygen. Hydroquinones are then conjugated with molecules such as glutathione, glucose, or sulfate, and excreted by the cell. However, some hydroquinone-containing molecules are unstable and react with oxygen in two 1-electron oxidations back to the quinone, generating ROS. The relative stability of hydroquinones toward air oxidation cannot be predicted based on molecular structure and it does not correlate with reduction potential.

NQO1 has attracted much attention as a potential target for the treatment of cancer because it has been shown to be frequently expressed at much higher levels in tumors relative to adjacent healthy tissue, particularly in the case of lung cancer. In addition, NQO1 activity appears to increase during tumor progression. Other than for lung, breast, and colon tissues, relatively little data on the levels of NQO1 in normal tissues has been reported. Whereas low levels of NQO1 are reported in bone marrow and liver cells—two tissues frequently damaged by chemotherapeutics—high levels of NQO1 have been noted in stomach and kidney cells.

The prospect of discovering toxins that are activated, instead of deactivated, by NQO1 has attracted researchers for many years. Such molecules would turn this normally cytoprotective enzyme into a liability for the cell. Two general classes of molecules have been discovered that fit this description: DNA alkylators whose electrophilicity is increased after bioreduction, and redox cycling molecules that generate ROS catalytically after reduction. Examples of such DNA alkylators include Mitomycin C, EO9, and MeDZQ and examples of such ROS generators include β-lapachone and streptonigrin, the cytotoxic mechanisms of which each involve NQO1-mediated bioreduction. These classes of molecules are composed almost exclusively of quinone-containing compounds.

The concentration of β-lap delivered to cells may induce different forms of cell death, with lower concentrations inducing apoptosis and higher concentrations initiating calcium-dependent necroptosis. In addition to ROS generation in RBCs, the poor aqueous solubility of β-lap necessitates the use of hydroxypropyl-β-cyclodextrin (HPβCD) as a solubility aid, high concentrations of which cause hemolysis of RBCs in vitro. To address the issues of compound instability and damage to RBCs, the Boothman and Gao groups have designed a micellar formulation of β-lap that demonstrates greatly improved PK properties and efficacy in murine tumor models (Blanco, Boothman, Gao et al., *Cancer Res.* 2010, 70, 3896).

While personalized medicine strategies have produced life-saving anticancer drugs, they affect only a small percentage of cancer patients. Because NQO1 levels are highly elevated in a large number of solid tumors, a treatment that successfully exploits NQO1 levels could benefit a significant fraction of all cancer patients. Despite the extensive efforts expended in discovering and developing NQO1-dependent cytotoxins, none of these compounds are both sufficiently selective for NQO1 and sufficiently stable in vivo to prove whether or not targeting NQO1 overexpression is a viable anticancer strategy. What is needed is evidence that DNQ and its derivatives possess the selectivity and stability required to validate NQO1 as a target for the treatment of cancer. What is also needed is new compounds and compositions that can selectively inhibit cancer cells and be used in therapeutic cancer therapies.

SUMMARY

The invention provides compounds, compositions and methods to treat tumor cells, for example, tumor cells having elevated levels of NQO1. A first aspect of the invention thus provides novel DNQ compounds of Formula (I):

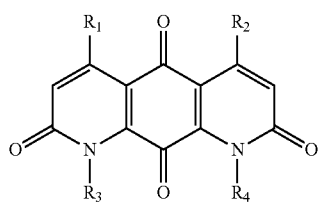

(I)

wherein
$R_1$, $R_2$, $R_3$, and $R_4$ are each independently —H or —X—R;
each X is independently a direct bond or a bridging group, wherein the bridging group is —O—, —S—, —NH—, —C(=O)—, —O—C(=O)—, —C(=O)—O—, —O—C(=O)—O—, or a linker of the formula —W-A-W—, wherein
each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-10, or a direct bond, wherein each R' is independently H, (C$_1$-C$_6$)alkyl, or a nitrogen protecting group; and
each A is independently (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— — interrupted between two carbons, or between a carbon and an oxygen, with a cycloalkyl, heterocycle, or aryl group;
each R is independently alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^y$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;
wherein any alkyl or aryl can be optionally substituted with one or more hydroxy, amino, cyano, nitro, or halo groups;
or a salt or solvate thereof;
provided that when $R_1$, $R_2$, and $R_3$ are methyl, $R_4$ is not H or methyl; and provided that when $R_1$, $R_3$, and $R_4$ are methyl, the group —X—R of $R_2$ is not —CH$_2$—OAc. In some embodiments, when $R_1$, $R_3$, and $R_4$ are methyl, the X group of $R_2$ is not —CH$_2$—, or the R group of $R_2$ is not acyloxy.

A second aspect of the invention provides pharmaceutical compositions that contain at least one compound of Formula (I) and a pharmaceutically acceptable diluent, carrier, or excipient. The invention also provides for the use of compounds of Formula (I) for the preparation of pharmaceutical compositions, and the subsequent use of the compositions in the treatment of patients or subjects. Patients or subjects can be mammals, including humans.

A third aspect of the invention provides methods of treating, killing, or inhibiting the growth tumor cells that have elevated NQO1 levels or a tumor having cells that have elevated NQO1 levels, where at least one tumor cell is exposed to a therapeutically effective amount of a compound of Formula (I), a pharmaceutically acceptable salt or solvate thereof, or a pharmaceutically acceptable composition thereof.

DETAILED DESCRIPTION

Figure 1:
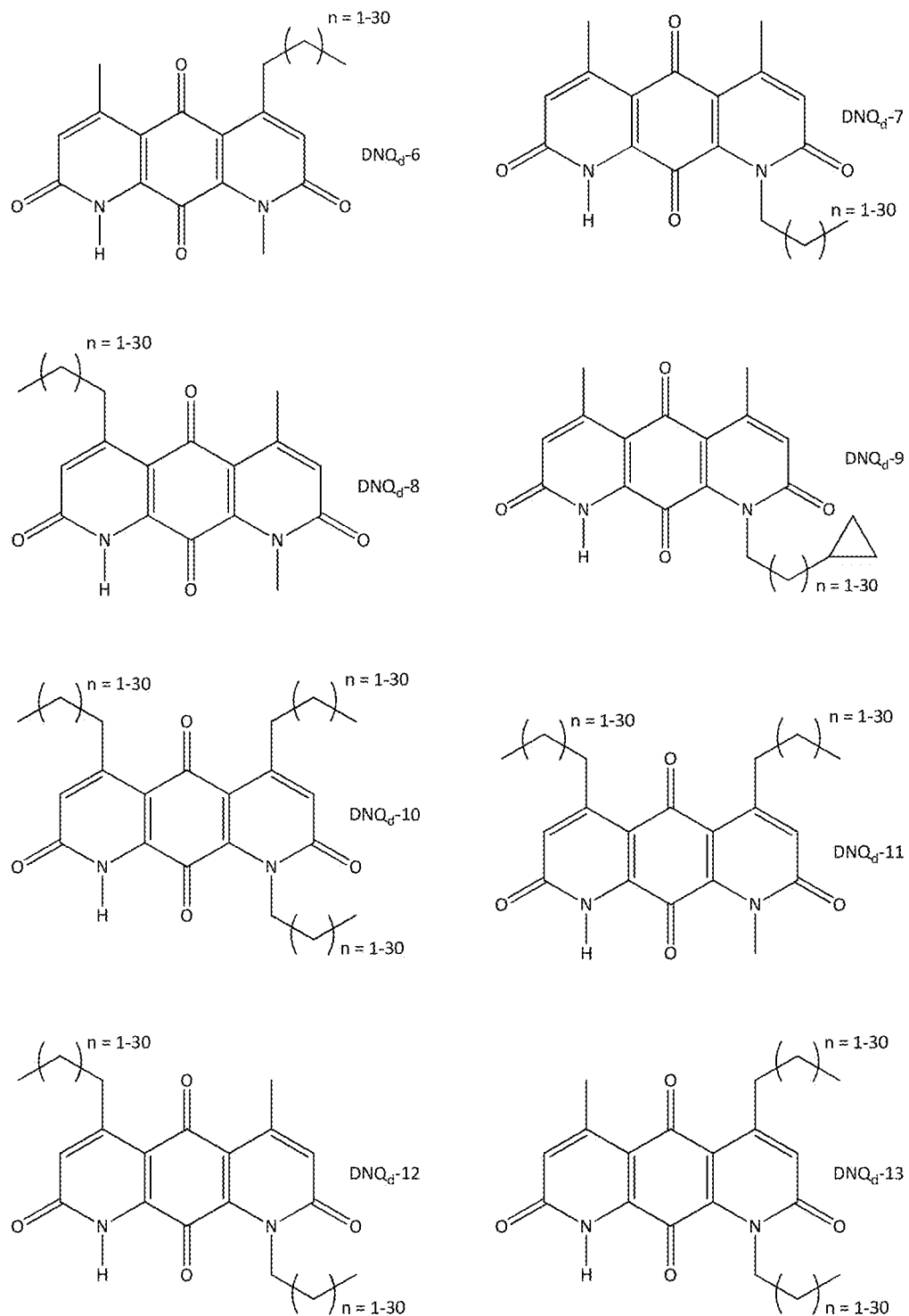
FIG. 1. Formulas of certain DNQ compounds, according to various embodiments of the invention.
Figure 1:
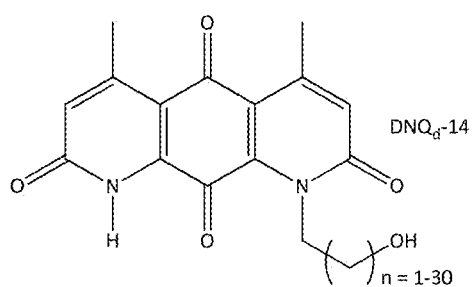
Figure 1:
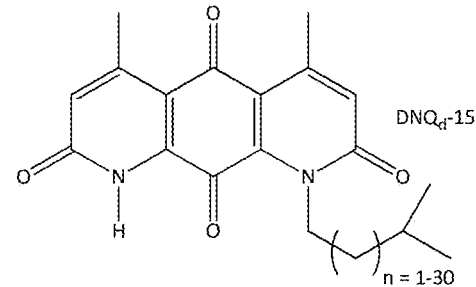
Figure 1:
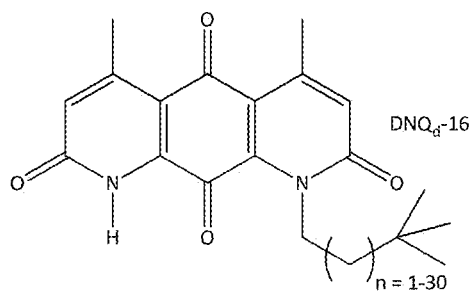
Figure 1:
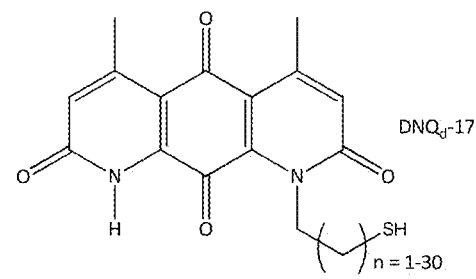
Figure 1:
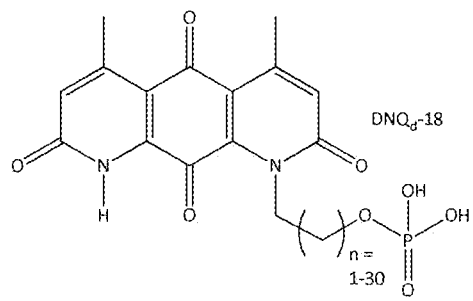
Figure 1:
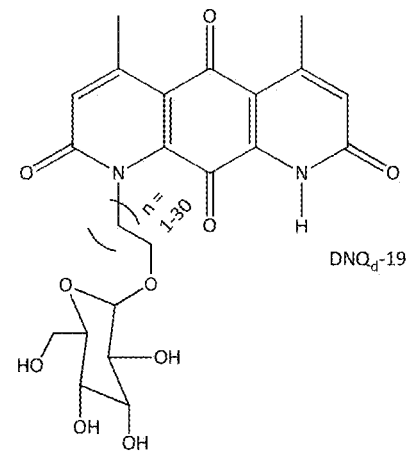
Figure 1:
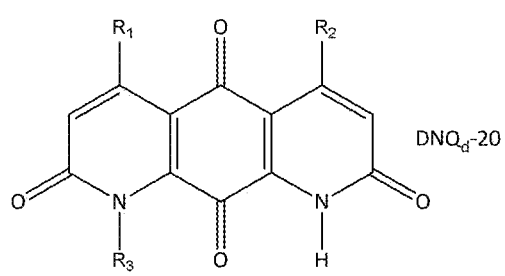
Figure 1:
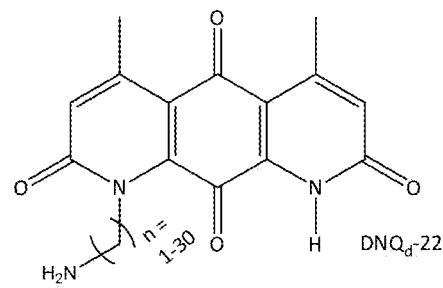
Figure 1:
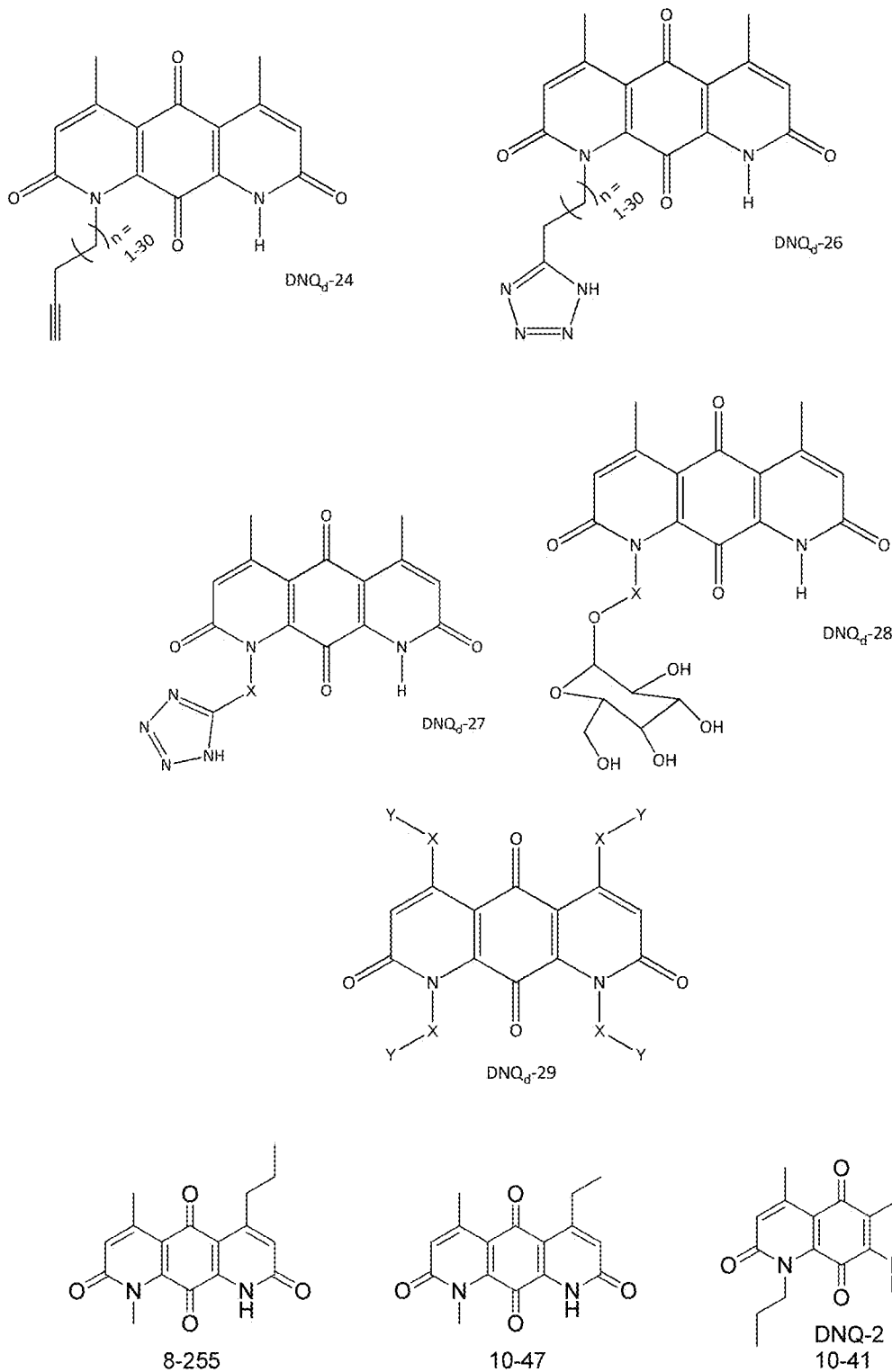

Tumor-selectivity remains a challenge for efficacious chemotherapeutic strategies against cancer. Although the recent development of β-lapachone to specifically exploit elevated levels of NAD(P)H:quinone oxidoreductase 1 (NQO1) in most solid tumors represents a novel chemotherapeutic approach, additional compounds that kill by programmed necrosis at increased potency are needed. This disclosure demonstrates that deoxynyboquinone (DNQ) kills a wide spectrum of cancer cell types (i.e., breast, non-small-cell lung, prostate, pancreatic) in an NQO1-dependent manner with greatly improved (20- to 100-fold) potency compared to β-lapachone. DNQ lethality relies on NQO1-dependent futile redox cycling, using oxygen and generating extensive reactive oxygen species (ROS), particularly superoxide and hydrogen peroxide. Elevated ROS levels cause extensive DNA lesions and PARP-1 hyperactivation that, in turn, results in severe NAD+/ATP depletion that stimulates calcium-dependent programmed necrotic cell death responses unique to this class of NQO1 'bioactivated' drugs (i.e., β-lapachone and DNQ).

A 2 hour exposure of NQO1+ cells to DNQ ($LD_{90}$: 50-250 nM) was sufficient for complete cell death, while genetically match NQO1− cells were unaffected. NQO1 or PARP-1 knockdown spared the short-term lethality of DNQ-treated NQO1+ cells. BAPTA-AM (cytosolic $Ca^{2+}$ chelator) and catalase (enzymatic $H_2O_2$ scavenger) rescued DNQ-induced lethality by long-term survival assessments. Thus, DNQ is a potent chemotherapeutic agent exhibiting a wide therapeutic window that holds great promise for targeted therapy against a wide spectrum of difficult to treat cancers, including pancreatic and non-small cell lung cancer.

Despite considerable advances in cancer chemotherapy, the lack of selectivity of most cancer chemotherapeutics remains a major limiting factor. This disclosure describes the evaluation of elevated NAD(P)H:quinone oxidoreductase-1 (NQO1, DT-diaphorase, EC 1.6.99.2) levels found in most solid tumors, particularly in non-small-cell lung cancer cells (NSCLC), prostate, pancreatic and breast, for development of therapeutic treatments. NQO1 is an inducible Phase II detoxifying two-electron oxidoreductase capable of reducing most quinones, forming stable hydroquinones. In most cases, glutathione transferase then detoxifies hydroquinones, conjugating them with glutathione for secretion, and effectively avoiding more toxic semiquinones.

For some rare compounds, however, NQO1-mediated bioreduction can be exploited for antitumor activity. Rather than promoting detoxification, NQO1 activity can convert specific quinones into highly cytotoxic species. Most antitumor quinones dependent on NQO1 are DNA alkylators: (a) mitomycin C (MMC); (b) RH1; (c) E09; and (d) AZQ. However, these DNA alkylators are not only subject to detoxification pathways, but resistance from elevated or inducible DNA repair pathways limit their usefulness. Furthermore, many of these drugs are efficient substrates for one-electron oxidoreductases ubiquitously expressed in normal tissues.

The ortho-naphthoquinone, β-lapachone (β-lap, Scheme 1), kills cultured cancer cells and murine xenograft and orthotopic human or mouse tumor models in vivo in an NQO1-dependent manner. In contrast to alkylating quinones, β-lap induces cell death by NQO1-dependent reactive oxygen species (ROS) formation and oxidative stress. NQO1 metabolism of β-lap results into an unstable hydroquinone that is spontaneously oxidized by two equivalents of dioxygen, generating superoxide.

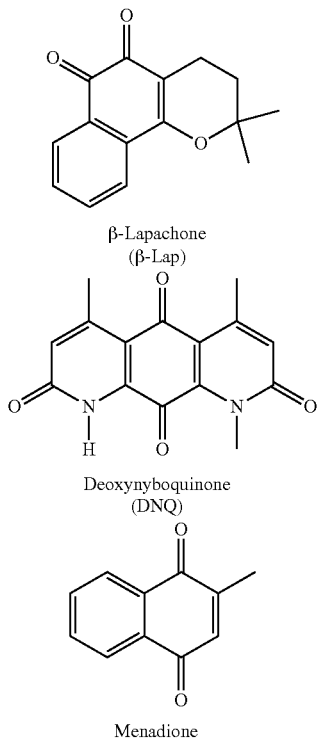

Scheme 1. Examples of Quinone Compounds.

β-Lapachone
(β-Lap)

Deoxynyboquinone
(DNQ)

Menadione

A futile cycle of oxidoreduction is thus established, and elevated superoxide levels, in turn cause massive DNA base and single strand break (SSBs) lesions that normally are easily and rapidly repaired. However, extensive DNA lesions created in β-lap-treated NQO1 over-expressing cancer cells results in hyperactivation of poly(ADP-ribose)polymerase-1 (PARP1), an otherwise essential base and SSB repair enzyme. In turn, PARP1 hyperactivation results in dramatic reduction of the NAD+/ATP pool due to ADP-ribosylation, causing tremendous energy depletion and cell death. As a result, β-lap kills NQO1+ cancer cells by a unique programmed necrosis mechanism that is: (a) independent of caspase activation or p53 status; (b) independent of bcl-2 levels; (c) not affected by BAX/BAK deficiencies; (d) independent of EGFR, Ras or other constitutive signal transduction activation; and/or (e) not dependent on proliferation, since NQO1 is expressed in all cell cycle phases. Thus, β-lap is an attractive experimental chemotherapeutic, and various β-lap formulations have been, or are in, phase I/II clinical trials.

However, β-lap has a fairly low potency ($LD_{50}$: 2-10 μM) in vitro, and has limited aqueous solubility that complicates formulation and delivery. Although nanoparticle strategies for β-lap delivery solved formulations issues, resulting in promising antitumor efficacy, there is a clear need for better compounds to efficiently exploit NQO1 over-expression in solid tumors.

Deoxynyboquinone (DNQ Scheme 1) is a promising antineoplastic agent whose mechanism of action has not been elucidated. Prior data indicated that DNQ killed cancer cells through oxidative stress and ROS formation. The cytotoxicity of DNQ was partially prevented by N-acetylcysteine, a global free radical scavenger and precursor to glutathione. It has now been show that DNQ undergoes an NQO1-dependent futile cycle similar to β-lap, where oxygen is consumed, ROS is formed and extensive DNA damage triggers PARP1 hyperactivation, with dramatic decreases in essential $NAD^+$/ATP nucleotide pools, indicative of programmed necrosis. Importantly, DNQ is 20- to 100-fold more potent than β-lap, with a significantly enhanced therapeutic window in NQO1+ versus NQO1− NSCLC cells. Efficacious NQO1-dependent killing by DNQ is also shown in breast, prostate, and pancreatic cancer models in vitro. Furthermore, we show that in vitro NQO1 processes DNQ much more efficiently than β-lap, suggesting that increased utilization accounts for its increased potency. Thus, DNQ offers significant promise as a selective chemotherapeutic agent for the treatment of solid tumors with elevated NQO1 levels.

Because NQO1 is overexpressed in the majority of solid tumors, and the cytotoxicity of DNQ depends predominately on the elevated expression of the enzyme NQO1, DNQ and its derivatives can be an excellent way to approach targeting solid tumors. The invention provides numerous new cytotoxic compounds that can be used as new cancer therapeutics.

The foregoing and other objects and features of the disclosure will become more apparent from the following detailed description, which proceeds with reference to the accompanying figures. Further embodiments, forms, features, aspects, benefits, objects, and advantages of the present application shall become apparent from the detailed description and figures provided herewith.

DEFINITIONS

In general, the terms and phrases used herein have their art-recognized meaning, which can be found by reference to standard texts, journal references and contexts known to those skilled in the art. Such art-recognized meanings may be obtained by reference to technical dictionaries, such as *Hawley's Condensed Chemical Dictionary* $14^{th}$ Edition, by R. J. Lewis, John Wiley & Sons, New York, N.Y., 2001.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase one or more is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments and any further applications of the principles of the invention as described herein are contemplated as would normally occur to one skilled in the art to which the invention relates.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Whenever a range is given in the specification, for example, a temperature range, a time range, a carbon chain range, or a composition or concentration range, all intermediate ranges and subranges, as well as all individual values included in the ranges given are intended to be individually included in the disclosure. It will be understood that any subranges or individual values in a range or subrange that are included in the description can be optionally excluded from embodiments of the invention.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

A "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

A "therapeutically effective amount" of a compound with respect to the subject method of treatment refers to an amount of the compound(s) in a preparation which, when administered as part of a desired dosage regimen (to a mammal, such as a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. The term "treating" or "treatment" can include reversing, reducing, or arresting the symptoms, clinical signs, and underlying pathology of a condition in manner to improve or stabilize a subject's condition.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

The term "exposing" is intended to encompass definitions as broadly understood in the art. In an embodiment, the term means to subject or allow to be subjected to an action, influence, or condition. For example and by way of example only, a cell can be subjected to the action, influence, or condition of a therapeutically effective amount of a pharmaceutically acceptable form of a chemotherapeutic agent.

The term "cancer cell" is intended to encompass definitions as broadly understood in the art. In an embodiment, the term refers to an abnormally regulated cell that can contribute to a clinical condition of cancer in a human or animal. In an embodiment, the term can refer to a cultured cell line or a cell within or derived from a human or animal body. A cancer cell can be of a wide variety of differentiated cell, tissue, or organ types as is understood in the art.

The term "tumor" refers to a neoplasm, typically a mass that includes a plurality of aggregated malignant cells.

The following groups can be R groups or bridging groups, as appropriate.

The term "alkyl" refers to a monoradical branched or unbranched saturated hydrocarbon chain preferably having from 1 to 30 carbon atoms. Short alkyl groups are those having 1 to 12 carbon atoms including methyl, ethyl, propyl, butyl, pentyl and hexyl groups, including all isomers thereof. Long alkyl groups are those having 12-30 carbon atoms. The group may be a terminal group or a bridging group.

Alkyl, heteroalkyl, aryl, heteroaryl, and heterocycle groups, and cyclic and/or unsaturated versions thereof, can be R groups of Formula I, and each group can be optionally substituted.

The term "substituted" indicates that one or more hydrogen atoms on the group indicated in the expression using "substituted" is replaced with a "substituent". The number referred to by 'one or more' can be apparent from the moiety one which the substituents reside. For example, one or more can refer to, e.g., 1, 2, 3, 4, 5, or 6; in some embodiments 1, 2, or 3; and in other embodiments 1 or 2. The substituent can be one of a selection of indicated groups, or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)O$_2$RR, —P(=O)O$_2$RR, —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle (alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on a substituted group.

The term "heteroalkyl," by itself or in combination with another term, means, unless otherwise stated, a stable straight or branched chain, or cyclic hydrocarbon radical, or combinations thereof, often having from 2 to 14 carbons, or 2 to 10 carbons in the chain, including at least one carbon atom and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. The heteroalkyl group can have, for example, one to about 20 carbon atoms in a chain. Examples include, but are not limited to, —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, O—CH$_3$, —O—CH$_2$—CH$_3$, and —CN. Additional examples of heteroalkyl groups include alkyl ethers, secondary and tertiary alkyl amines, amides, alkyl sulfides, and the like. The group may be a terminal group or a bridging group. As used herein, reference to a chain when used in the context of a bridging group refers to the direct chain of atoms linking the two terminal positions of the bridging group.

The term "alcohol" as used herein may be defined as an alcohol that comprises a $C_{1-12}$ alkyl moiety substituted at a hydrogen atom with one hydroxyl group. Alcohols include ethanol, n-propanol, i-propanol, n-butanol, i-butanol, s-butanol, t-butanol, n-pentanol, i-pentanol, n-hexanol, cyclohexanol, n-heptanol, n-octanol, n-nonanol, n-decanol, and the like. The carbon atoms in alcohols can be straight, branched or cyclic.

"Acyl" may be defined as an alkyl-CO— group in which the alkyl group is as described herein. Examples of acyl include acetyl and benzoyl. The alkyl group can be a $C_1$-$C_6$ alkyl group. The group may be a terminal group or a bridging (i.e., divalent) group.

"Alkoxy" refers to an —O-alkyl group in which alkyl is defined herein. Preferably the alkoxy is a $C_1$-$C_6$alkoxy. Examples include, but are not limited to, methoxy and ethoxy. The group may be a terminal group or a bridging group.

"Alkenyl" as a group or part of a group denotes an aliphatic hydrocarbon group containing at least one carbon-carbon double bond and which may be straight or branched preferably having 2-14 carbon atoms, more preferably 2-12 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkynyl" as a group or part of a group may be defined as an aliphatic hydrocarbon group containing a carbon-carbon triple bond, the chain of which may be straight or branched preferably having from 2-14 carbon atoms, more preferably 2-12 carbon atoms, more preferably 2-6 carbon atoms in the normal chain. Exemplary structures include, but are not limited to, ethynyl and propynyl. The group may be a terminal group or a bridging group.

"Alkenyloxy" refers to an —O— alkenyl group in which alkenyl is as defined herein. Preferred alkenyloxy groups are $C_1$-$C_6$ alkenyloxy groups. The group may be a terminal group or a bridging group.

"Alkynyloxy" refers to an —O-alkynyl group in which alkynyl is as defined herein. Preferred alkynyloxy groups are $C_1$-$C_6$ alkynyloxy groups. The group may be a terminal group or a bridging group.

"Alkoxycarbonyl" refers to an —C(O)—O-alkyl group in which alkyl is as defined herein. The alkyl group is preferably a $C_1$-$C_6$ alkyl group. Examples include, but not limited to, methoxycarbonyl and ethoxycarbonyl. The group may be a terminal group or a bridging group.

"Alkylsulfinyl" may be defined as a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group is preferably a $C_1$-$C_6$ alkyl group. Examples include, but not limited to methylsulfonyl and ethylsulfonyl. The group may be a terminal group or a bridging group.

"Amino" refers to —NH$_2$, and "alkylamino" refers to —NR$_2$, wherein at least one R is alkyl and the second R is alkyl or hydrogen. The term "acylamino" refers to RC(=O)NH—, wherein R is alkyl or aryl. The alkyl group can be, for example, a $C_1$-$C_6$ alkyl group. Examples include, but are not limited to methylamino and ethylamino. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle of 3 to about 30 carbon atoms, often containing 3 to about 9 carbons per ring, such as cyclopropyl, cyclobutyl, cyclopentyl, cyclohexyl, cyclooctyl, and the like. It includes monocyclic systems such as cyclopropyl and cyclohexyl, bicyclic systems such as decalin, and polycyclic systems such as adamantane. The group may be a terminal group or a bridging group.

"Cycloalkenyl" may be defined as a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

Alkyl and cycloalkyl groups can be substituents on the alkyl portions of other groups, such as without limitation, alkoxy, alkyl amines, alkyl ketones, arylalkyl, heteroarylalkyl, alkylsulfonyl and alkyl ester substituents and the like. The group may be a terminal group or a bridging group.

"Cycloalkylalkyl" may be defined as a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Heterocycloalkyl" refers to a saturated or partially saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morpholino, 1,3-diazapane, 1,4-diazapane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, and (2-tetrahydrothiofuranyl)methyl. The group may be a terminal group or a bridging group.

"Halo" refers to a halogen substituent such as fluoro, chloro, bromo, or iodo.

The term "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 18 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, as described above in the definition of "substituted". Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$alkylaryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The abbreviation "$DNQ_d$" as used herein refers to an analog or derivative of DNQ.

Additional groups that can be bridging groups or terminal groups of $R_1$, $R_2$, $R_3$, and $R_4$ are described below.

The term "carbonate ester" may be defined as a functional group having a general structure R'OC(=O)OR, where R' can be the tricyclic core of Formula I and R can be as defined in the definitions of the variables of Formula I.

The term "ester" may be defined as a functional group having a general structure RC(=O)OR', where R' can be the tricyclic core of Formula I and R can be as defined in the definitions of the variables of Formula I, or vice versa.

The term "hemiacetal" may be defined as a functional group having a general structure

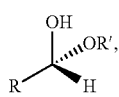

where R' can be the tricyclic core of Formula I and R can be as defined in the definitions of the variables of Formula I, or vice versa.

The term "carboxamide" may be defined as a functional group having a general structure

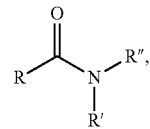

where R' can be the tricyclic core of Formula I and R can be as defined in the definitions of the variables of Formula I, or vice versa, and R" can be R can be as defined in the definitions of the variables of Formula I.

The term "imine" may be defined as a functional group having general structures

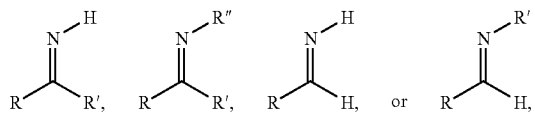

where R' can be the tricyclic core of Formula I and R can be as defined in the definitions of the variables of Formula I, or vice versa, and R" can be the tricyclic core of Formula I or R can be as defined in the definitions of the variables of Formula I.

A "pyridyl" group can be a 2-pyridyl, 3-pyridyl, or 4-pyridyl group.

The term "imide" may be defined as a functional group having a general structure

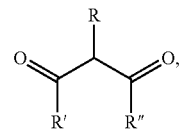

where R' can be the tricyclic core of Formula I and R can be as defined in the definitions of the variables of Formula I, or vice versa, and R" can be the tricyclic core of Formula I or R can be as defined in the definitions of the variables of Formula I.

The term "sulfhydryl" may be defined as a functional group having a general structure —S—H.

The term "sulfinyl" may be defined as a functional group having a general structure

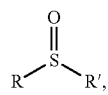

where R' can be the tricyclic core of Formula I and R can be as defined in the definitions of the variables of Formula I, or vice versa.

The term "sulfonyl" may be defined as a functional group having a general structure

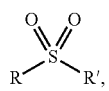

where R' can be the tricyclic core of Formula I and R can be as defined in the definitions of the variables of Formula I, or vice versa.

The term "phosphate" may be defined as a functional group having general structures

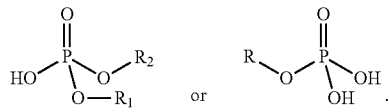

The term "phosphono" may be defined as a functional group having a general structure

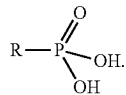

The term "hexose" may be defined as a monosaccharide having six carbon atoms having the general chemical formula $C_6H_{12}O_6$ and can include aldohexoses which have an aldehyde functional group at position 1 or ketohexoses which have a ketone functional group at position 2. Example aldohexoses include, allose, altrose, glucose, mannose, gulose, idose, galactose, and talose, in either D or L form.

Compounds and Methods of the Invention

The invention provides DNQ compounds and methods of using such compounds. Accordingly, the invention provides compounds of Formula (I):

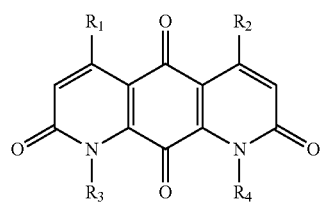

wherein $R_1$, $R_2$, $R_3$, and $R_4$ are each independently —H or —X—R;

each X is independently a direct bond or a bridging group, wherein the bridging group is —O—, —S—, —NH—, —C(=O)—, —O—C(=O)—, —C(=O)—O—, —O—C(=O)—O—, or a linker of the formula —W-A-W—, wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-10, or a direct bond, wherein each R' is independently H, (C$_1$-C$_6$)alkyl, or a nitrogen protecting group; and each A is independently (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a cycloalkyl, heterocycle, or aryl group;

each R is independently alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^y$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;

wherein any alkyl or aryl can be optionally substituted with one or more hydroxy, amino, cyano, nitro, or halo groups;

or a salt or solvate thereof.

In some embodiments, when $R_1$, $R_2$, and $R_3$ are methyl, $R_4$ is not H or methyl. In other embodiments, when $R_1$, $R_3$, and $R_4$ are methyl, the group —X—R of $R_2$ is not —CH$_2$—OAc. In certain embodiments, when $R_1$, $R_3$, and $R_4$ are methyl, the R group of $R_2$ is not acyloxy. In various embodiments, $R_1$-$R_4$ are not each H. In certain embodiments, $R_1$-$R_4$ are not each alkyl, such as unsubstituted alkyl. In some embodiments, $R_1$-$R_4$ are not each methyl.

In one embodiment, $R_1$, $R_2$, $R_3$, and $R_4$ are each (C$_{1-20}$) alkyl groups. In some embodiments, the (C$_{1-20}$)alkyl group is a (C$_{2-20}$)alkyl group, a (C$_{3-20}$)alkyl group, a (C$_{4-20}$)alkyl group, a (C$_{5-20}$)alkyl group, or a (C$_{10-20}$)alkyl group. The alkyl groups can be substituted, for example, with a hydroxyl or phosphate group. The phosphate group can be a phosphonic acid or a phosphonic acid salt, such as a lithium salt, a sodium salt, a potassium salt, or other known salt of phosphonic acids.

A specific value for $R_1$ is H. A specific value for $R_2$ is H. A specific value for $R_3$ is H. A specific value for $R_4$ is H.

A specific value for $R_1$ is methyl. A specific value for $R_2$ is methyl. A specific value for $R_3$ is methyl. A specific value for $R_4$ is methyl. The methyl can be substituted as described above for the term "substituted".

Figure 2:
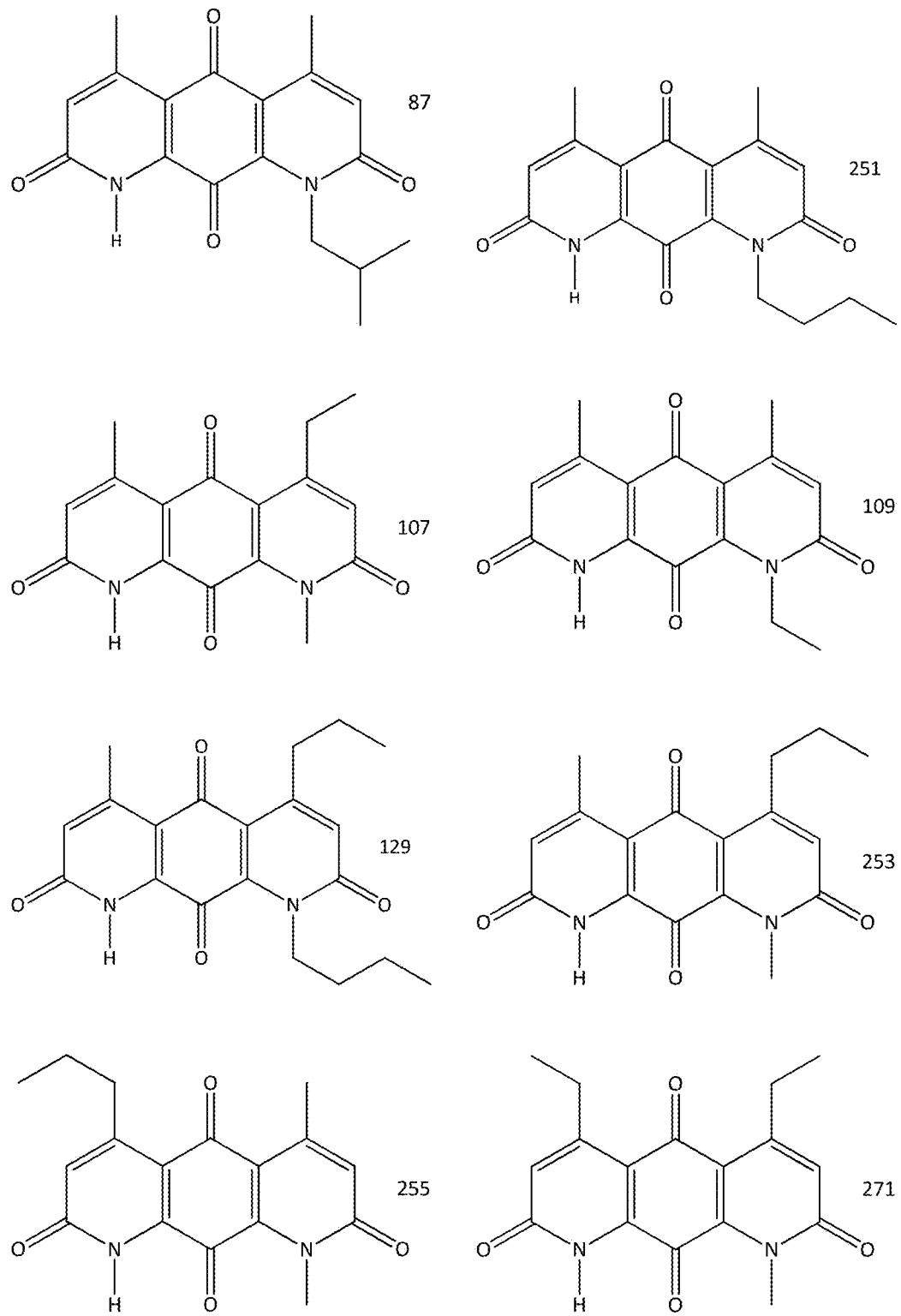
FIG. 2. Examples of specific DNQ compounds.
Figure 2:
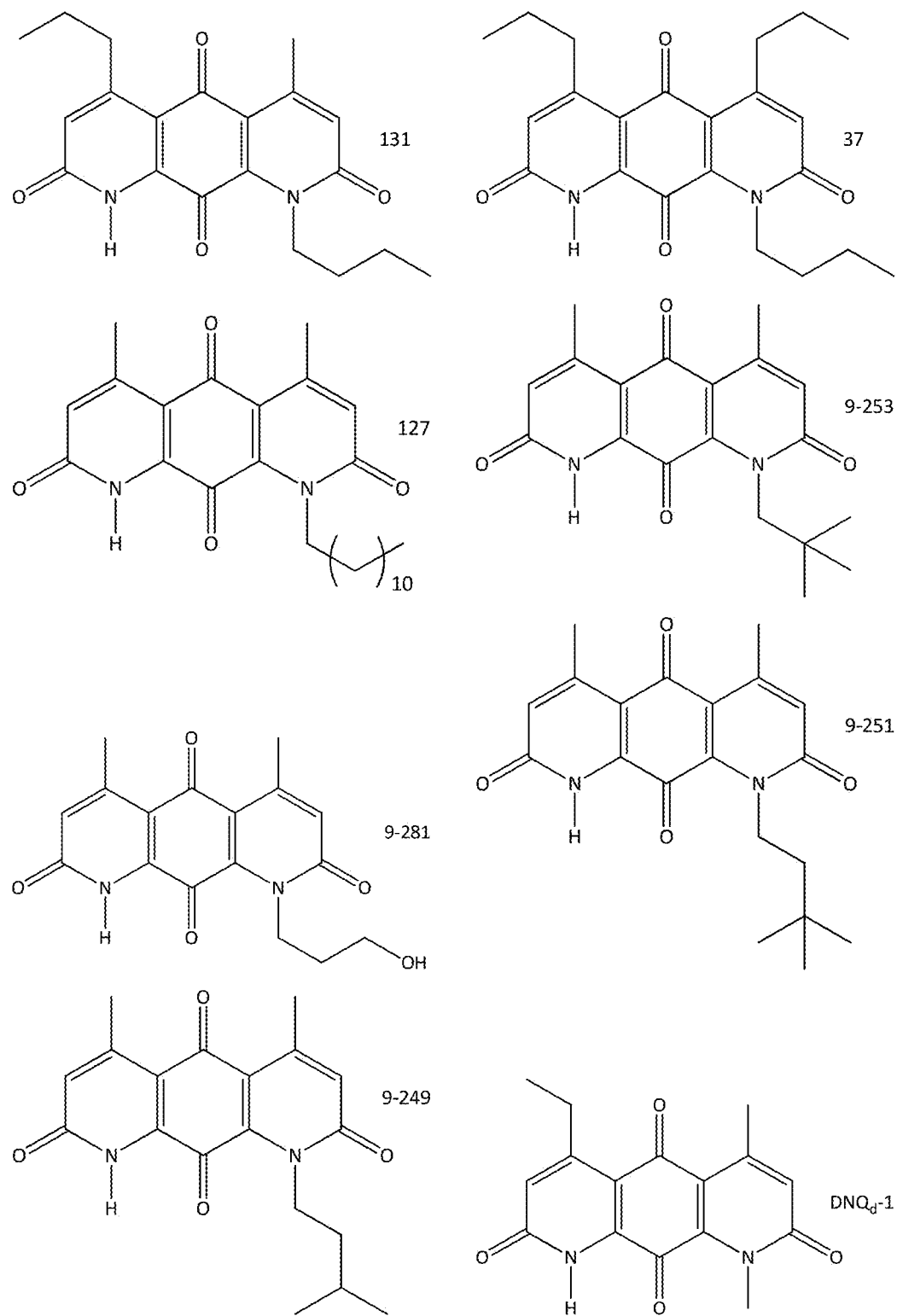
Figure 2:
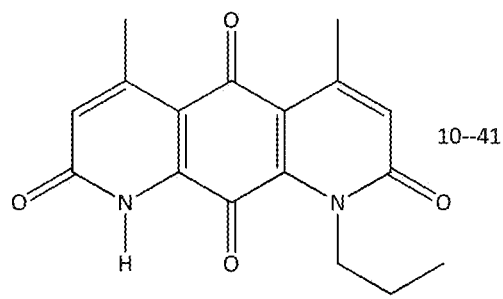
Figure 2:
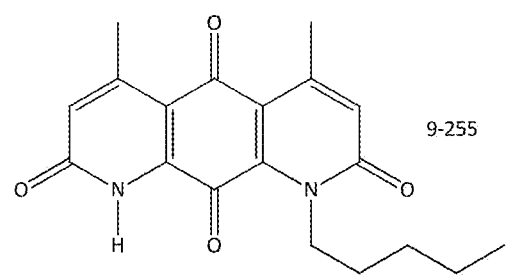
Figure 2:
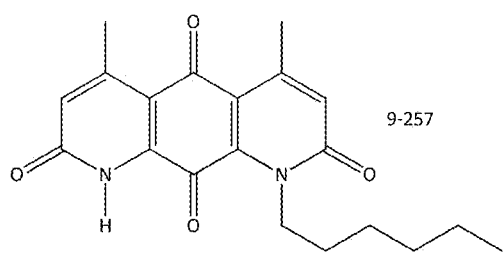
Figure 2:
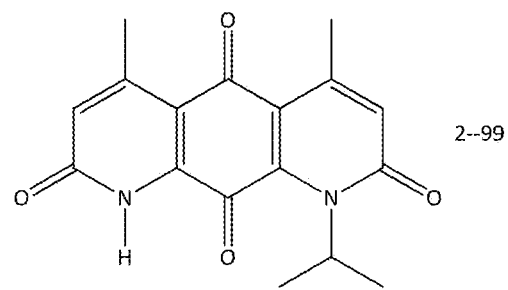
Figure 2:
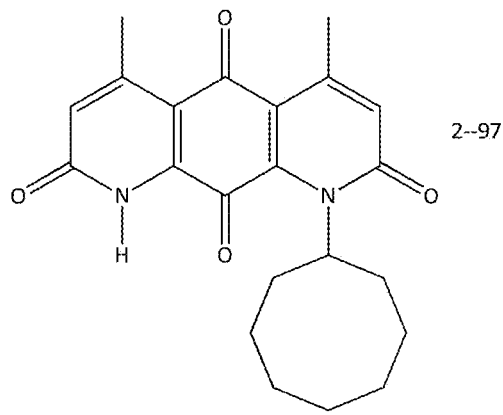
Figure 2:
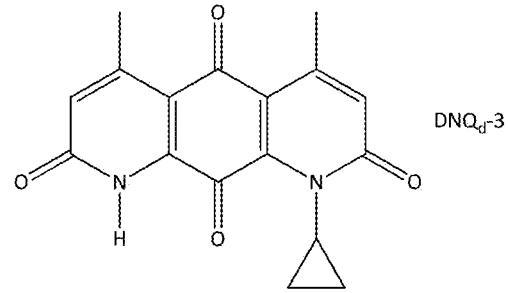
Figure 2:
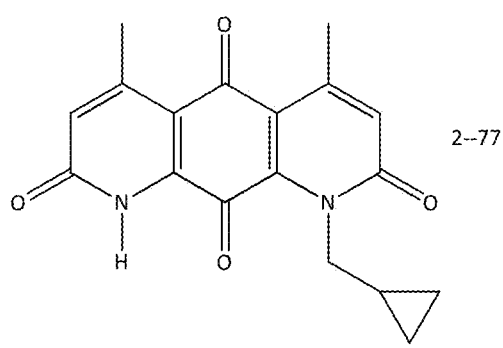
Figure 2:
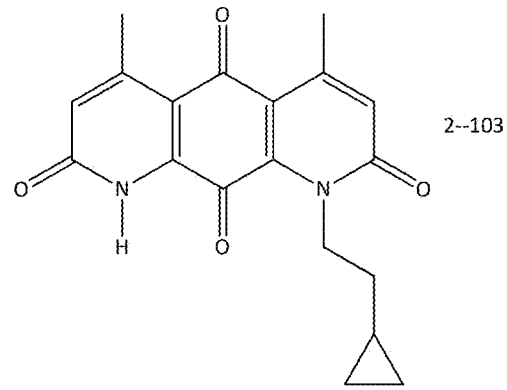
Figure 2:
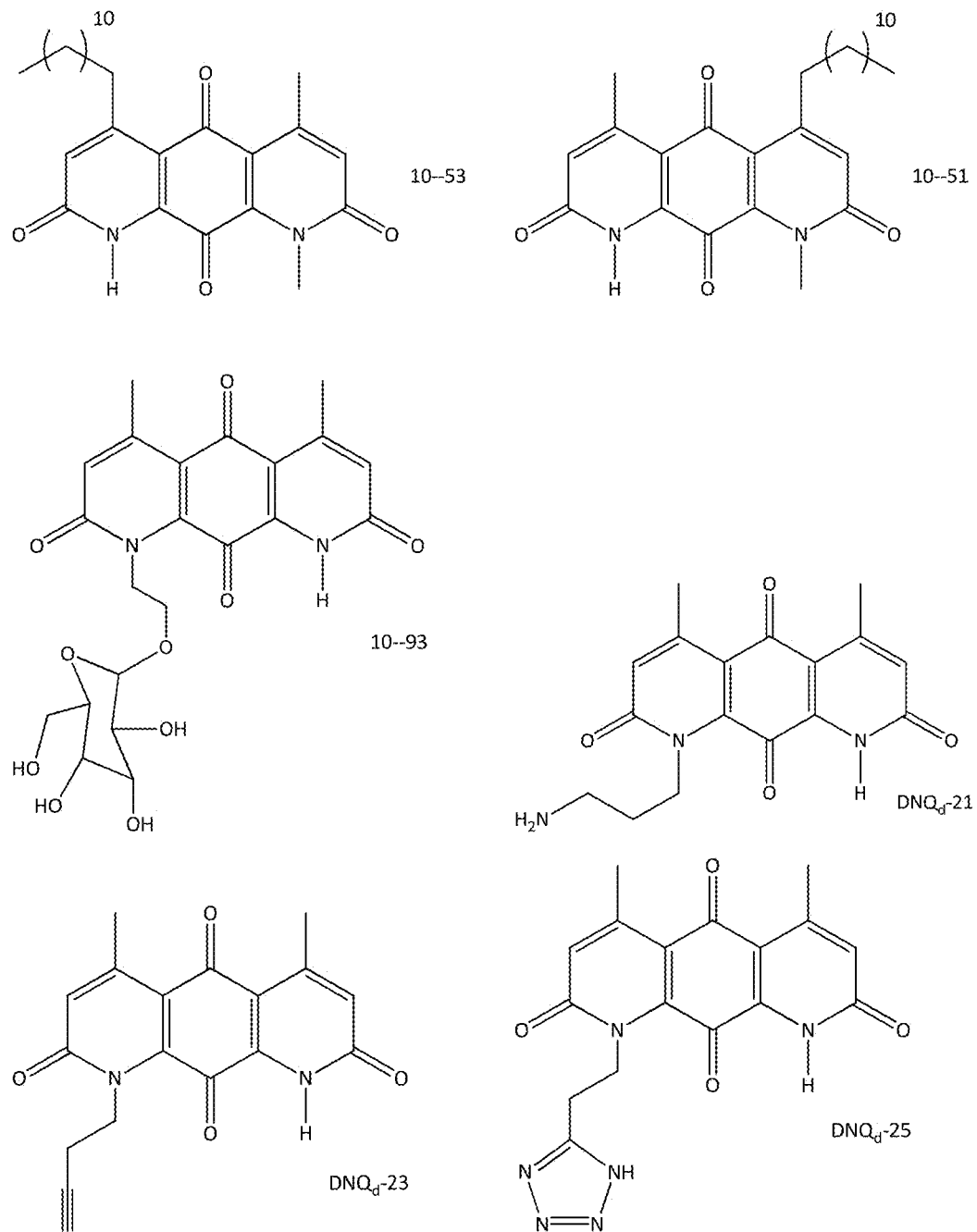

In some embodiments of Formula (I):

$R_1$ and $R_2$ are methyl; $R_3$ is hydrogen; and $R_4$ is 2-methylpropane;

$R_1$ and $R_2$ are methyl; $R_3$ is hydrogen; and $R_4$ is butyl;

$R_1$ and $R_4$ are methyl and $R_3$ is hydrogen; and $R_2$ is ethyl;

$R_1$ and $R_2$ are methyl and $R_3$ is hydrogen; and $R_4$ is ethyl;

$R_1$ is methyl; $R_3$ is hydrogen; $R_2$ is propyl; and $R_4$ is butyl;

$R_1$ and $R_4$ are methyl; $R_2$ is propyl and $R_3$ is hydrogen;

$R_1$ is propyl; $R_2$ and $R_4$ are methyl and $R_3$ is hydrogen;

$R_1$ and $R_2$ are ethyl; $R_3$ is hydrogen; and $R_2$ is methyl;

$R_1$ is propyl; $R_2$ is methyl; $R_3$ is hydrogen; and $R_4$ is butyl;

$R_1$ and $R_2$ are propyl; $R_3$ is hydrogen; and $R_4$ is butyl;

$R_1$ and $R_2$ are methyl; $R_3$ is hydrogen; and $R_4$ is $C_{12}$alkyl;

$R_1$ and $R_2$ are methyl; $R_3$ is hydrogen; and $R_4$ is tert-butyl;

$R_1$ and $R_2$ are methyl; $R_3$ is hydrogen; and $R_4$ is hydroxypropyl;
$R_1$ and $R_2$ are methyl; $R_3$ is hydrogen; and $R_4$ is 3,3-dimethylbutyl [—$CH_2CH_2C(CH_3)_2CH_3$];
$R_1$ and $R_2$ are methyl; $R_3$ is hydrogen; and $R_4$ is 3-methylbutyl [—$CH_2CH_2CH(CH_3)CH_3$];
$R_2$ and $R_4$ are methyl; $R_3$ is hydrogen; and $R_1$ is ethyl;
$R_1$ and $R_2$ are methyl; $R_3$ is hydrogen; and $R_4$ is propyl;
$R_1$ and $R_2$ are methyl; $R_3$ is hydrogen; and $R_4$ is n-pentyl;
$R_1$ and $R_2$ are methyl; $R_3$ is hydrogen; and $R_4$ is n-hexyl;
$R_1$ and $R_2$ are methyl; $R_3$ is hydrogen; and $R_4$ is isopropyl;
$R_1$ and $R_2$ are methyl; $R_3$ is hydrogen; and $R_4$ is cyclooctyl;
$R_1$ and $R_2$ are methyl; $R_3$ is hydrogen; and $R_4$ is cyclopropyl;
$R_1$ and $R_2$ are methyl; $R_3$ is hydrogen; and $R_4$ is methylcyclopropyl;
$R_1$ and $R_2$ are methyl; $R_3$ is hydrogen; and $R_4$ is ethylcyclopropyl;
$R_1$ is $C_{12}$alkyl; $R_2$ and $R_4$ are methyl; and $R_3$ is hydrogen;
$R_1$ and $R_4$ are methyl; $R_3$ is hydrogen; and $R_2$ is $C_{12}$alkyl;
$R_1$, $R_2$, and $R_3$ are methyl; and $R_4$ is —$CH_2OPO_3Na_2$;
$R_1$ is —$CH_2OPO_3Na_2$; $R_2$ and $R_3$ are methyl; and $R_4$ is hydrogen;
$R_1$ and $R_3$ are methyl; $R_2$ is —$CH_2OPO_3Na_2$; and $R_4$ is hydrogen;
$R_1$ and $R_2$ are methyl; $R_3$ is —$CH_2OPO_3Na_2$; and $R_4$ is hydrogen;
$R_1$ and $R_2$ are methyl; $R_3$ is —$CH_2CH_2OPO_3Na_2$; and $R_4$ is hydrogen;
$R_1$, $R_2$, and $R_3$ are methyl; and $R_4$ is —$CH_2OH$;
$R_1$ is —$CH_2OH$; $R_2$ and $R_3$ are methyl; and $R_4$ is hydrogen;
$R_1$ and $R_3$ are methyl; $R_2$ is —$CH_2OH$; and $R_4$ is hydrogen;
$R_1$ and $R_2$ are methyl; $R_3$ is —$CH_2OH$; and $R_4$ is hydrogen; or
$R_1$ and $R_2$ are methyl; $R_3$ is —$CH_2CH_2OH$; and $R_4$ is hydrogen. Additional specific compounds and formulas of the invention are illustrated in FIGS. 1 and 2.

In certain embodiments of Formula I, $R^1$ is $(C_{1-4})$ alkyl group. In certain instances, $R^1$ is $(C_{1-3})$ alkyl group. In certain instances, $R^1$ is $(C_{1-2})$ alkyl group.

In certain embodiments of Formula I, $R^2$ is $(C_{1-4})$ alkyl group. In certain instances, $R^2$ is $(C_{1-3})$ alkyl group. In certain instances, $R^2$ is $(C_{1-2})$ alkyl group.

In certain embodiments of Formula I, $R^3$ is hydrogen.

In certain embodiments of Formula I, $R^4$ is an optionally substituted $(C_{1-10})$ alkyl group, where the alkyl group is substituted with hydroxyl, halogen, amino, or thiol. In certain instances, $R^4$ is $(C_{1-10})$ alkyl group, $(C_{1-8})$ alkyl group, $(C_{1-6})$ alkyl group, or $(C_{1-4})$ alkyl group. In certain instances, $R^4$ is $(C_{2-6})$ alkyl group. In certain instances, $R^4$ is a substituted $(C_{1-10})$ alkyl group, substituted $(C_{1-8})$ alkyl group, substituted $(C_{1-6})$ alkyl group, or substituted $(C_{1-4})$ alkyl group, where the alkyl group is substituted with hydroxyl, halogen, amino, or thiol. In certain instances, $R^4$ is an alkyl group is substituted with hydroxyl. In certain instances, $R^4$ is an alkyl group is substituted with halogen. In certain instances, $R^4$ is an alkyl group is substituted with amino. In certain instances, $R^4$ is an alkyl group is substituted with thiol.

In certain embodiments of Formula I, $R^1$ and $R^2$ are independently $(C_{1-4})$ alkyl groups; $R^3$ is hydrogen; and $R^4$ is an optionally substituted $(C_{1-10})$ alkyl group, where the alkyl group is substituted with hydroxyl, halogen, amino, and thiol.

In certain embodiments of Formula I, $R^1$ and $R^2$ are independently $(C_{1-2})$ alkyl groups; $R^3$ is hydrogen; and $R^4$ is an optionally substituted $(C_{1-10})$ alkyl group, where the alkyl group is substituted with hydroxyl, halogen, amino, and thiol.

In certain embodiments of Formula I, $R^1$ and $R^2$ are independently $(C_{1-2})$ alkyl groups; $R^3$ is hydrogen; and $R^4$ is $(C_{1-10})$ alkyl group.

In certain embodiments of Formula I, $R^1$ and $R^2$ are independently $(C_{1-2})$ alkyl groups; $R^3$ is hydrogen; and $R^4$ is $(C_{1-8})$ alkyl group.

In certain embodiments of Formula I, $R^1$ and $R^2$ are independently $(C_{1-2})$ alkyl groups; $R^3$ is hydrogen; and $R^4$ is $(C_{1-6})$ alkyl group.

In certain embodiments of Formula I, $R^1$ and $R^2$ are independently $(C_{1-2})$ alkyl groups; $R^3$ is hydrogen; and $R^4$ is $(C_{1-4})$ alkyl group.

In certain embodiments of Formula I, $R^1$ and $R^2$ are independently $(C_{1-2})$ alkyl groups; $R^3$ is hydrogen; and $R^4$ is $(C_{2-6})$ alkyl group.

In certain embodiments of Formula I, $R^1$ and $R^2$ are independently $(C_{1-2})$ alkyl groups; $R^3$ is hydrogen; and $R^4$ is a substituted $(C_{1-6})$ alkyl group, where the alkyl group is substituted with hydroxyl, halogen, amino, and thiol.

In certain embodiments of Formula I, $R^1$ and $R^2$ are independently $(C_{1-2})$ alkyl groups; $R^3$ is hydrogen; and $R^4$ is a substituted $(C_{1-4})$ alkyl group, where the alkyl group is substituted with hydroxyl, halogen, amino, and thiol.

In certain embodiments, a compound of Formula I is Compound 87 or a salt or solvate thereof:

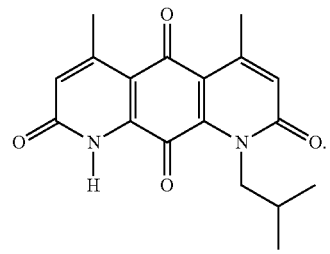 [SMILES: Cc1cc(=O)[nH]c2c1C(=O)c1c(C)cc(=O)n(CC(C)C)c1C2=O]

In certain embodiments, a compound of Formula I is Compound 9-253 or a salt or solvate thereof:

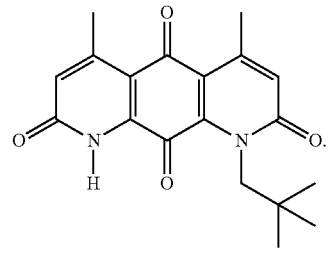 [SMILES: Cc1cc(=O)[nH]c2c1C(=O)c1c(C)cc(=O)n(CC(C)(C)C)c1C2=O]

In certain embodiments, a compound of Formula I is Compound 9-251 or a salt or solvate thereof:

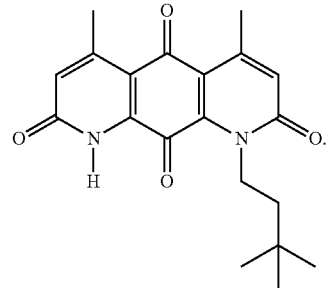 [SMILES: Cc1cc(=O)[nH]c2c1C(=O)c1c(C)cc(=O)n(CCC(C)(C)C)c1C2=O]

In certain embodiments, a compound of Formula I is Compound 10-41 or a salt or solvate thereof:

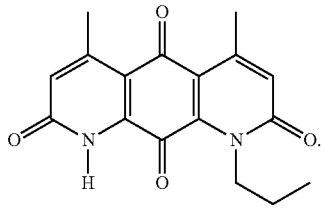 [SMILES: CCCn1c2c(c(C)cc1=O)C(=O)c1c(C)cc(=O)[nH]c1C2=O]

In certain embodiments, a compound of Formula I is Compound 109 or a salt or solvate thereof:

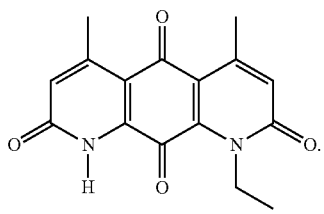 [SMILES: CCn1c2c(c(C)cc1=O)C(=O)c1c(C)cc(=O)[nH]c1C2=O]

In certain embodiments, a compound of Formula I is Compound 107 or a salt or solvate thereof:

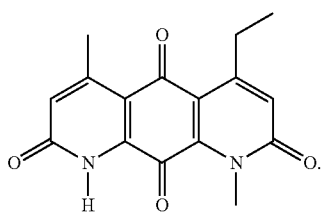 [SMILES: CCc1cc(=O)n(C)c2c1C(=O)c1c(C)cc(=O)[nH]c1C2=O]

In certain embodiments, a compound of Formula I is Compound 9-281 or a salt or solvate thereof:

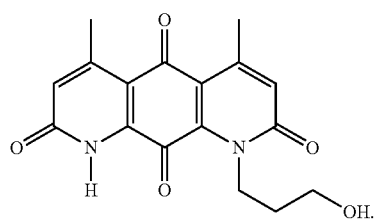 [SMILES: Cc1cc(=O)[nH]c2c1C(=O)c1c(C)cc(=O)n(CCCO)c1C2=O]

In certain embodiments, a compound of Formula I is Compound 9-249 or a salt or solvate thereof:

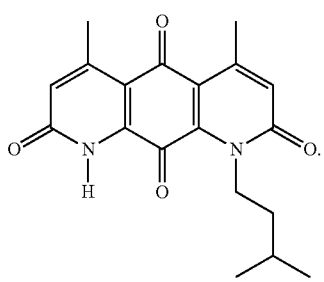 [SMILES: Cc1cc(=O)[nH]c2c1C(=O)c1c(C)cc(=O)n(CCC(C)C)c1C2=O]

In certain embodiments, a compound of Formula I is Compound 9-255 or a salt or solvate thereof:

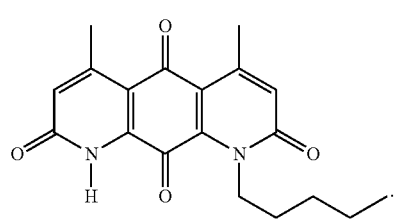 [SMILES: CCCCCn1c2c(c(C)cc1=O)C(=O)c1c(C)cc(=O)[nH]c1C2=O]

In certain embodiments, a compound of Formula I is Compound 9-257 or a salt or solvate thereof:

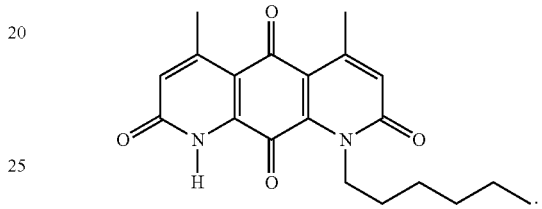

The invention also provides a pharmaceutical composition comprising a compound of Formula (I) and a pharmaceutically acceptable diluent, excipient, or carrier. The carrier can be water, for example, in the presence of hydroxypropyl-β-cyclodextrin (HPβCD). The solubility of the compound can be increase by about 100 times, about 200 times, about 500 times, about 1000 times, about 2000 times, or about 3000 times, compared to the compounds solubility in water without HPβCD.

The invention further provides DNQ compounds of formula (II):

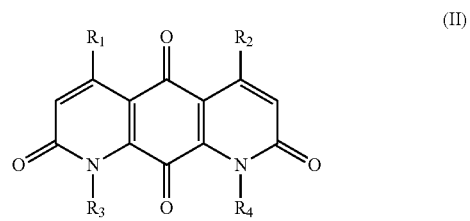

wherein
  $R_1$ and $R_2$ are each independently $C_{1-30}$alkyl;
  $R_3$ is hydrogen or $C_{1-30}$alkyl;
  $R^4$ is $C_{1-30}$alkyl or $C_{3-30}$cycloalkyl-$C_{1-30}$alkyl;
  where the $C_{1-30}$alkyl groups can include, for example, methyl, ethyl, n-propyl, isopropyl, butyl, isobutyl, sec- and tert-butyl, pentyl, hexyl, heptyl, octyl, nonyl, and the like;
  where each $R^1$, $R^2$, or $R^4$ alkyl can be optionally functionalized with functional group $R^a$;
  where $R^a$ is either a bridging group or a terminal group selected from:

| | |
|---|---|
| (1) | Hydroxyl, |
| (2) | Carbonyl, |
| (3) | Aldehyde, |
| (4) | Haloformyl, |
| (5) | Carbonate ester, |
| (6) | Carboxyl, |
| (7) | Ester, |
| (8) | Hydroperoxy, |
| (9) | Peroxy, |
| (10) | Phenyl, |
| (11) | Alkenyl, |
| (12) | Benzyl, |
| (13) | Alkynyl, |
| (14) | Ether, |
| (15) | Hemiacetal, |
| (16) | Hemiketal, |
| (17) | Acetal, |
| (18) | Ketal, |
| (19) | Orthoester, |
| (20) | Orthocarbonate ester, |
| (21) | Carboxamide, |
| (22) | Amine, |
| (23) | Ketamine, |
| (24) | Imide, |
| (25) | Azide, |
| (26) | Azo, |
| (27) | Cyanate, |
| (28) | Isocyanate, |
| (29) | Nitrate, |
| (30) | Nitrile, |
| (31) | Isonitrile, |
| (32) | Nitrosooxy, |
| (33) | Nitro, |
| (34) | Nitroso, |
| (35) | Pyridyl, |
| (36) | Sulfhydryl, |
| (37) | Sulfide, |
| (38) | Disulfide, |
| (39) | Sulfinyl, |
| (40) | Sulfonyl, |
| (41) | Sulfino, |
| (42) | Sulfo, |
| (43) | Thiocyanate, |
| (44) | Isothiocyanate, |
| (45) | Carbonothioyl, |
| (46) | Phosphine, |
| (47) | Phosphono, |
| (48) | Phosphate, |
| (49) | Halogen; or |
| (50) | Hexose; | or a pharmaceutically acceptable salt or solvate thereof.

In some embodiments, when $R_1$, $R_2$, and $R_4$ are methyl, $R_3$ is not hydrogen or methyl.

As to any of the above formulas or groups that contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds.

Selected substituents of the compounds described herein may be present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above. In some embodiments, recursive substituents are present only to the extent that the molecular mass of the compound is about 400 to about 1600, about 450 to about 1200, about 500 to about 100, about 600 to about 800. In other embodiments, recursive substituents are present only to the extent that the molecular mass of the compound is less than 2000, less than 1800, less than 1600, less than 1500, less than 1400, less than 1200, less than 1000, less than 900, less than 800, less than 750, less than 700, or less than about 600.

Patients with solid tumors having elevated NQO1 levels can be treated through the administration of an effective amount of a pharmaceutically active form of DNQ and/or $DNQ_d$ (DNQ compounds). DNQ and $DNQ_d$ compounds can be, for example, a compound defined by one of the formulas of FIG. 1, or a compound illustrated in FIG. 2. In FIG. 1 where n=1-30, the value of n can be 1 or any integer from 1 up to about 30. Thus, the range 1-30 includes each individual integer from 1 to 30 and any ranges from any one to any second number from 1 to 30. In each range described herein, a portion of the range may also be excluded from the embodiment defined. For example, in various embodiments, a variable n can be 6-24, and another n variable of the same formula can be 1-24.

In FIG. 1 for $DNQ_d$-20, $R_1$, $R_2$, and $R_3$ can be as defined for Formula I above. In various embodiments, $R_1$, $R_2$, and $R_3$ can also each independently be $C_{1-20}$alkyl, or each of $R_1$, $R_2$ or $R_3$ can be independently be linked to the anomeric position of a hexose, optionally through a linker, such as a linker of formula —W-A-W— or a $(C_1-C_{10})$alkylene group.

In FIG. 1 for $DNQ_d$-27 and $DNQ_d$-28, X can be a linker of formula —W-A-W— or a divalent bridging group such as a divalent alkyl, alkenyl, alkynyl, heteroalkyl, acycloalkyl, cycloalkenyl, heterocycloalkyl, heterocycloalkenyl, cycloalkylalkyl, heterocycloalkylalkyl, cycloalkylheteroalkyl, heterocycloalkylheteroalkyl, alkoxy, alkoxyalkyl, alkenyloxy, alkynyloxy, cycloalkylkoxy, heterocycloalkyloxy, amino, alkylamino, aminoalkyl, acylamino, arylamino, sulfonylamino, sulfinylamino, alkoxycarbonyl, alkylaminocarbonyl, sulfonyl, alkylsulfonyl, alkylsulfinyl, arylsulfonyl, arylsulfinyl, aminosulfonyl, or acyl, each of which may be optionally substituted.

In FIG. 1 for $DNQ_d$-29, each X can independently be a linker of formula —W-A-W— or a divalent bridging group as described above for $DNQ_d$-27 and $DNQ_d$-28; and each Y can independently be:

| | |
|---|---|
| (1) | Hydroxyl, |
| (2) | Aldehyde, |
| (3) | Carboxyl, |
| (4) | Haloformyl, |
| (5) | Hydroperoxy, |
| (6) | Phenyl, |
| (7) | Benzyl, |
| (8) | Alkyl, |
| (9) | Alkenyl, |
| (10) | Alkynyl, |
| (11) | Acetate, |
| (12) | Amino, |
| (13) | Azide, |
| (14) | Azo, |
| (15) | Cyano, |
| (16) | Isocyanato, |
| (17) | Nitrate, |
| (18) | Isonitrile, |
| (19) | Nitrosooxy, |
| (20) | Nitro, |

-continued

| | |
|---|---|
| (21) | Nitroso, |
| (22) | Pyridyl, |
| (23) | Sulfhydryl, |
| (24) | Sulfonic acid, |
| (25) | Sulfonate, |
| (26) | Isothiocyanato, |
| (27) | Phosphine, |
| (28) | Phosphate, |
| (29) | Halo, or |
| (30) | Hexose. |

The invention also provides methods of treating a patient that has tumor cells having elevated NQO1 levels. The methods can include administering to a patient having tumor cells with elevated NQO1 levels a therapeutically effective amount of a compound of Formula (I), or a composition described herein. The invention further provides methods of treating a tumor cell having an elevated NQO1 level comprising exposing the tumor cell to a therapeutically effective amount of a compound or composition described herein, wherein the tumor cell is treated, killed, or inhibited from growing. The tumor or tumor cells can be malignant tumor cells. In some embodiments, the tumor cells are cancer cells, such as Non-Small-Cell Lung Carcinoma.

The methods of the invention may be thus used for the treatment or prevention of various neoplasia disorders including the group consisting of acral lentiginous melanoma, actinic keratoses, adenocarcinoma, adenoid cycstic carcinoma, adenomas, adenosarcoma, adenosquamous carcinoma, astrocytic tumors, bartholin gland carcinoma, basal cell carcinoma, bronchial gland carcinomas, capillary, carcinoids, carcinoma, carcinosarcoma, cavernous, cholangiocarcinoma, chondosarcoma, choriod plexus papilloma/carcinoma, clear cell carcinoma, cystadenoma, endodermal sinus tumor, endometrial hyperplasia, endometrial stromal sarcoma, endometrioid adenocarcinoma, ependymal, epitheloid, Ewing's sarcoma, fibrolamellar, focal nodular hyperplasia, gastrinoma, germ cell tumors, glioblastoma, glucagonoma, hemangiblastomas, hemangioendothelioma, hemangiomas, hepatic adenoma, hepatic adenomatosis, hepatocellular carcinoma, insulinoma, intaepithelial neoplasia, interepithelial squamous cell neoplasia, invasive squamous cell carcinoma, large cell carcinoma, leiomyosarcoma, lentigo maligna melanomas, malignant melanoma, malignant mesothelial tumors, medulloblastoma, medulloepithelioma, melanoma, meningeal, mesothelial, metastatic carcinoma, mucoepidermoid carcinoma, neuroblastoma, neuroepithelial adenocarcinoma nodular melanoma, oat cell carcinoma, oligodendroglial, osteosarcoma, pancreatic polypeptide, papillary serous adenocarcinoma, pineal cell, pituitary tumors, plasmacytoma, pseudosarcoma, pulmonary blastoma, renal cell carcinoma, retinoblastoma, rhabdomyosarcoma, sarcoma, serous carcinoma, small cell carcinoma, soft tissue carcinomas, somatostatin-secreting tumor, squamous carcinoma, squamous cell carcinoma, submesothelial, superficial spreading melanoma, undifferentiated carcinoma, uveal melanoma, verrucous carcinoma, vipoma, well differentiated carcinoma, and Wilm's tumor. Accordingly, the compositions and methods described herein can be used to treat bladder cancer, brain cancer (including intracranial neoplasms such as glioma, meninigioma, neurinoma, and adenoma), breast cancer, colon cancer, lung cancer (SCLC or NSCLC) ovarian cancer, pancreatic cancer, and prostate cancer.

Methods of Making the Compounds of the Invention

The invention also relates to methods of making the compounds and compositions of the invention. The compounds and compositions can be prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as standard organic reference texts such as *March's Advanced Organic Chemistry: Reactions, Mechanisms, and Structure*, $5^{th}$ Ed. by M. B. Smith and J. March (John Wiley & Sons, New York, 2001), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing)); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be $-100°$ C. to $200°$ C., solvents will be aprotic or protic depending on the conditions required, and reaction times will be 1 minute to 10 days. Work-up typically consists of quenching any unreacted reagents followed by partition between a water/organic layer system (extraction) and separation of the layer containing the product.

Oxidation and reduction reactions are typically carried out at temperatures near room temperature (about $20°$ C.), although for metal hydride reductions frequently the temperature is reduced to $0°$ C. to $-100°$ C. Heating can also be used when appropriate. Solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures ($0°$ C. to $-100°$ C.) are also common. Solvents can be either protic (common in equilibrating reactions) or aprotic (common in kinetically controlled reactions). Standard synthetic techniques such as azeotropic removal of reaction by-products and use of anhydrous reaction conditions (e.g. inert gas environments) are common in the art and will be applied when applicable.

Protecting Groups. The term "protecting group", "blocking group", or "PG" refers to any group which, when bound to a hydroxy or other heteroatom prevents undesired reactions from occurring at this group and which can be removed by conventional chemical or enzymatic steps to reestablish the hydroxyl group. The particular removable blocking group employed is not always critical and preferred removable hydroxyl blocking groups include conventional substituents such as, for example, allyl, benzyl, acetyl, chloroacetyl, thiobenzyl, benzylidene, phenacyl, methyl methoxy, silyl ethers (e.g., trimethylsilyl (TMS), t-butyl-diphenylsilyl (TB- DPS), or t-butyldimethylsilyl (TBS)) and any other group that can be introduced chemically onto a hydroxyl functionality and later selectively removed either by chemical or enzymatic methods in mild conditions compatible with the nature of the product. The R groups of Formula (I) can also be protecting groups, as described herein.

Suitable hydroxyl protecting groups are known to those skilled in the art and disclosed in more detail in T. W. Greene, *Protecting Groups In Organic Synthesis*; Wiley: New York, 1981 ("Greene") and the references cited therein, and Kocienski, Philip J.; *Protecting Groups* (Georg Thieme Verlag Stuttgart, New York, 1994), both of which are incorporated herein by reference.

Protecting groups are available, commonly known and used, and are optionally used to prevent side reactions with the protected group during synthetic procedures, i.e. routes or methods to prepare the compounds by the methods of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis.

Protecting groups do not need to be, and generally are not, the same if the compound is substituted with multiple PGs. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art. For further detail regarding carboxylic acid protecting groups and other protecting groups for acids, see Greene, cited above. Such groups include by way of example and not limitation, esters, amides, hydrazides, and the like.

Salts and Solvates

Pharmaceutically acceptable salts of compounds described herein are within the scope of the invention and include acid or base addition salts which retain the desired pharmacological activity and are not biologically undesirable (e.g., the salt is not unduly toxic, allergenic, or irritating, and is bioavailable). When a compound has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g. alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the invention has an acidic group, such as for example, a carboxylic acid group, it can form salts with metals, such as alkali and earth alkali metals (e.g. $Na^+$, $Li^+$, $K^+$, $Ca^{2+}$, $Mg^{2+}$, $Zn^{2+}$), ammonia or organic amines (e.g. dicyclohexylamine, trimethylamine, triethylamine, pyridine, picoline, ethanolamine, diethanolamine, triethanolamine) or basic amino acids (e.g. arginine, lysine and ornithine). Such salts can be prepared in situ during isolation and purification of the compounds or by separately reacting the purified compound in its free base or free acid form with a suitable acid or base, respectively, and isolating the salt thus formed.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds described herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Examples of suitable salts of the compounds described herein include their hydrochlorides, hydrobromides, sulfates, methanesulfonates, nitrates, maleates, acetates, citrates, fumarates, tartrates (e.g., (+)-tartrates, (−)-tartrates or mixtures thereof including racemic mixtures), succinates, benzoates and salts with amino acids such as glutamic acid. These salts may be prepared by methods known to those skilled in the art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the invention can contain both basic and acidic functionalities that allow the compounds to be converted into either base or acid addition salts.

Certain compounds of the invention can exist in unsolvated forms as well as solvated forms, including hydrated forms. In general, the solvated forms are equivalent to unsolvated forms and are encompassed within the scope of the invention. Certain compounds of the invention may exist in multiple crystalline or amorphous forms. In general, all physical forms are equivalent for the uses contemplated by the invention and are intended to be within the scope of the invention.

The term "solvate" refers to a solid compound that has one or more solvent molecules associated with its solid structure. Solvates can form when a compound is crystallized from a solvent. A solvate forms when one or more solvent molecules become an integral part of the solid crystalline matrix upon solidification. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. Hydrates can form when a compound is solidified or crystallized in water, where one or more water molecules become an integral part of the solid crystalline matrix. The compounds of the formulas described herein can be hydrates.

Pharmaceutical Compositions

The following describes information relevant to pharmaceutical and pharmacological embodiments and is further supplemented by information in the art available to one of ordinary skill. The exact formulation, route of administration and dosage can be chosen by an individual physician or clinician in view of a patient's condition (see e.g., Fingl et al., in *The Pharmacological Basis of Therapeutics*, 1975, Ch. 1).

It should be noted that the attending physician would know how to and when to terminate, interrupt, or adjust administration due to toxicity, or to organ dysfunctions, etc. Conversely, the attending physician would also know to adjust treatment to higher levels if the clinical response were not adequate (in light of or precluding toxicity aspects). The magnitude of an administered dose in the management of the disorder of interest can vary with the severity of the condition to be treated and to the route of administration. The severity of the condition may, for example, be evaluated, in part, by standard prognostic evaluation methods. Further, the dose and perhaps dose frequency, can also vary according to circumstances, e.g. the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995) and elsewhere in the art.

The compounds can be administered to a patient in combination with a pharmaceutically acceptable carrier, diluent, or excipient. The phrase "pharmaceutically acceptable" refers to those ligands, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" includes any and all solvents, dispersion media, diluents, coatings, surfactants, antioxidants, preservatives (e.g., antibacterial agents, antifungal agents), isotonic agents, absorption delaying agents, salts, buffers, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, *Remington's Pharmaceutical Sciences*, 18th Ed. Mack Printing Company, 1990, pp. 1289-1329, incorporated herein by reference). Except insofar as any conventional carrier is incompatible with the active ingredient, its use in the chemotherapeutic or pharmaceutical compositions is contemplated.

A $DNQ_d$ or DNQ compound may be combined with different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, *Remington's Pharmaceutical Sciences*, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

When administered to a subject, effective amounts will depend, of course, on the particular cancer being treated; the genotype of the specific cancer; the severity of the cancer; individual patient parameters including age, physical condition, size and weight, concurrent treatment, frequency of treatment, and the mode of administration. These factors are well known to the physician and can be addressed with no more than routine experimentation. In some embodiments, it is preferred to use the highest safe dose according to sound medical judgment.

In certain embodiments, pharmaceutical compositions may comprise, for example, at least about 0.1% of a $DNQ_d$ or DNQ compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

A $DNQ_d$ or DNQ compound may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, triethylamine, histidine or procaine.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are optionally provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose (HPC); or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose.

The composition should be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Formulation of DNQ Compounds for In Vivo Administration

The aqueous solubility of DNQ at pH 7.4 in phosphate buffered saline (PBS) was measured by LC-MS. DNQ was sonicated for 30 minutes in PBS then undissolved solid was removed by filtration through a 0.45 µm syringe filter and the filtrate was analyzed by LC-MS ($\lambda$=275 nm, ESI-TOF in negative mode). The optimal sonication time was determined by sonicating DNQ for 1, 5, 10, and 30 minutes. While the concentration of DNQ in solution increased substantially between 1, 5, and 10 minutes, there was only a minor difference between 10 and 30 minutes. During the 30 minute sonication the water bath warmed to 45° C. (samples were cooled to room temperature before filtration). A calibration curve was generated from 1-100 µM by dissolving DNQ in methanol to a concentration of 500 µM and making dilutions of this stock in 80:20 water:methanol. The calibration curve (measure by UV absorbance) was linear over this range; 1 µM was approximately the limit of detection. The solubility of DNQ in PBS was measured to be 115 µM. The solution was very pale yellow.

Because of the poor aqueous solubility of DNQ we investigated the use of 2-hydroxypropyl-beta-cyclodextrin (HPβCD), a common excipient, to improve the solubility of DNQ. In the absence of HPβCD, the solubility of DNQ increases significantly in strongly basic solutions and DNQ precipitates when the pH is returned to neutral. However, in the presence of a sufficient amount of HPβCD, DNQ does not precipitate when the pH is returned to neutral. This same neutral solution of DNQ in HPβCD cannot be made directly (i.e. without pH adjustment). This indicates that DNQ compounds deprotonate in base and this deprotonated molecule forms a tight complex with HPβCD which is stable enough to prevent protonation as the pH decreases. The only proton on DNQ that might reasonably be deprotonated in aqueous base is the N—H. Although the acidity of the N—H bond of DNQ has not been measured, it has been measured for a derivative of DNQ and found to have a pKa of 8.0.

The protocol for formulating DNQ compounds in HPβCD is as follows: the DNQ compound is slurried in a 20% solution of HPβCD in pH 7.4 PBS and the pH is then increased by the addition of 10 M NaOH to induce dissolution of the DNQ compound. The pH is returned to pH 7.5-8.0 by the careful addition of 1 M HCl. A 3.3 mM solution of the DNQ compound can be made by this method which is stable at least 24 hours. This represents a 30-fold increase in solubility of DNQ over PBS alone.

We initially chose a 20% HPβCD solution. However, we have found that β-lap was formulated as a 40% solution of HPβCD for human clinical trials and our experience with DNQ indicates that the concentration of DNQ increases linearly with that of HPβCD; thus a 40% HPβCD solution would permit the creation of a 6.6 mM solution of DNQ and other DNQ compounds.

Combination Therapy

Active ingredients described herein (e.g., compounds of Formula (I)) can also be used in combination with other active ingredients. Such combinations are selected based on the condition to be treated, cross-reactivities of ingredients and pharmaco-properties of the combination. For example, when treating cancer, the compositions can be combined with other anti-cancer compounds (such as paclitaxel or rapamycin).

It is also possible to combine a compound of the invention with one or more other active ingredients in a unitary dosage form for simultaneous or sequential administration to a patient. The combination therapy may be administered as a simultaneous or sequential regimen. When administered sequentially, the combination may be administered in two or more administrations.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-cancer effect denotes an anti-cancer effect that is greater than the predicted purely additive effects of the individual compounds of the combination.

Combination therapy is further described by U.S. Pat. No. 6,833,373 (McKearn et al.), which includes additional active agents that can be combined with the compounds described herein, and additional types of cancer and other conditions that can be treated with a compound described herein.

Accordingly, it is an aspect of this invention that a $DNQ_d$ or DNQ can be used in combination with another agent or therapy method, preferably another cancer treatment. A $DNQ_d$ or DNQ may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 6 hours, about 8 hours, about 9 hours, about 12 hours, about 15 hours, about 18 hours, about 21 hours, about 24 hours, about 28 hours, about 31 hours, about 35 hours, about 38 hours, about 42 hours, about 45 hours, to about 48 hours or more prior to and/or after administering the organic arsenical. In certain other embodiments, an agent may be administered within from about 1 day, about 2 days, about 3 days, about 4 days, about 5 days, about 6 days, about 8 days, about 9 days, about 12 days, about 15 days, about 16 days, about 18 days, about 20 days, to about 21 days prior to and/or after administering the organic arsenical. In some situations, it may be desirable to extend the time period for treatment significantly, however, where several weeks (e.g., about 1, about 2, about 3, about 4, about 6, or about 8 weeks or more) lapse between the respective administrations.

Administration of the chemotherapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery.

Chemotherapy

Cancer therapies can also include a variety of combination therapies with both chemical and radiation based treatments. Combination chemotherapies include the use of chemotherapeutic agents such as, cisplatin, etoposide, irinotecan, camptostar, topotecan, paclitaxel, docetaxel, epothilones, taxotere, taxol, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib hydrochloride), antibodies to EGFR, GLEEVEC™ (imatinib), intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, pentostatine, vinblastine, vincristine, vindesine, bleomycin, doxorubicin, dactinomycin, daunorubicin, epirubicin, idarubicin, mithramycin, deoxycoformycin, Mitomycin-C, L-Asparaginase, Teniposide 17α-Ethinylestradiol, Diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, Avastin, herceptin, Bexxar, Velcade, Zevalin, Trisenox, Xeloda, Vinorelbine, Porfimer, Erbitux™ (cetuximab), Liposomal, Thiotepa, Altretamine, Melphalan, Trastuzumab, Lerozole, Fulvestrant, Exemestane, Fulvestrant, Ifosfomide, Rituximab, C225, Campath, carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP 16), tamoxifen, raloxifene, estrogen receptor binding agents, taxol (paclitaxel), gemcitabine, navelbine, farnesyl-protein transferase inhibitors, transplatinum, 5-fluorouracil, vincristine, vinblastine and methotrexate, or any analog or derivative variant of the foregoing.

Radiotherapy

Other factors that cause DNA damage and have been used extensively include what are commonly known as .gamma.-rays, X-rays, and/or the directed delivery of radioisotopes to tumor cells. Other forms of DNA damaging factors are also contemplated such as microwaves and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy

In yet another embodiment, the secondary treatment is a secondary gene therapy in which a therapeutic polynucleotide is administered before, after, or at the same time a first chemotherapeutic agent. Delivery of the chemotherapeutic agent in conjunction with a vector encoding a gene product will have a combined anti-hyperproliferative effect on target tissues.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention. The invention may be further understood by the following non-limiting examples.

Abbreviations used in the Schemes and Examples may include the following:
A549=adenocarcinomic human alveolar basal epithelial cells
ATP=adenosine triphosphate
β-lap=β-lapachone
DHE=dihydroethidium
DNQ=Deoxynyboquinone
$DNQ_d$=Any analog or derivative of deoxynyboquinone
ELISA=enzyme-linked immunosorbent assay
h=hour(s)
H596=[NCI-H596] human lung adenosquamous carcinoma cell line
HT1080=primate fibrosarcoma cell line
$LD_{50}$=lethal dose having 50% probability of causing death
$LD_{90}$=lethal dose having 90% probability of causing death
$LD_{100}$=lethal dose having 100% probability of causing death
MCF-7=human breast adenocarcinoma cell line
MDA-MB-231=human breast cancer cell line
MIA-PaCa2=Pancreatic cancer cell line
mins=minute(s)
NADH=nicotinamide adenine dinucleotide
NQO1=NAD(P)H:quinone oxidoreductase 1
NSCLC=non-small-cell lung cancer cells
OCR=oxygen consumption rates
p53=a tumor suppressor protein
PC-3=human prostate cancer cell line
ROS=reactive oxygen species
±SE=standard error
siRNA=small interfering ribonucleic acid
shRNA=small hairpin ribonucleic acid
μM=micromolar
nM=nanomolar
μmol=micromole

EXAMPLES

Example 1

Preparation of SCH 538415 and DNQ

A. Synthesis of SCH 538415.

Of the potential precursors to diazaanthracenols evaluated, the most successful route was through 2-61 (Scheme 1.12). The specific disposition of halides in compound 2-61 was envisioned to arise through sequential directed ortho lithiation of 2,6-dichloroanisole. As diiodination under such conditions is difficult, intermediate disilane 2-62 was targeted. Chloride is known to be a weak directing group for ortholithiation, but has been successfully utilized in a number of settings. However, lithium-chloride exchange appeared to be the dominant reaction in a variety of n- and s-butyllithium-mediated reactions, presumably due to the strong directing effects of the methoxy group. It was found that deprotonation with lithium diisopropyl amide (LDA) was both efficient and selective for the 3- and 5-positions (Scheme 1.12). In addition, the two-step sequence could be carried out in one pot. Trimethylsilyl chloride was an effective in situ-quench reagent, with highest conversions when additions of reagent were sequential, beginning with LDA. Iododesilylation of 2-62 by the action of iodine monochloride was rapid and quantitative, producing 2-61.

Scheme 1.12. Synthesis of SCH 538415.

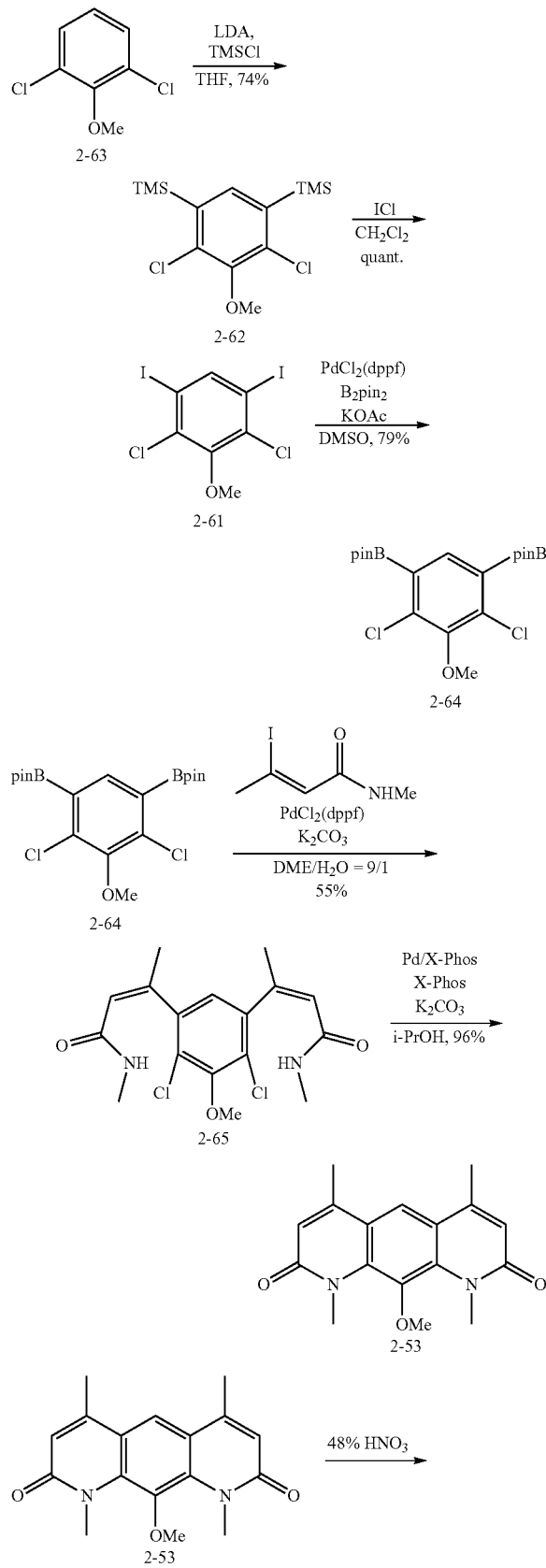

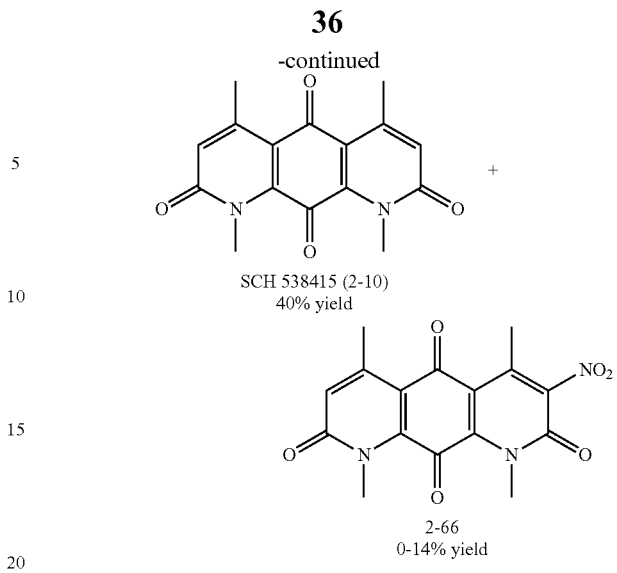

SCH 538415 (2-10)
40% yield 2-66
0-14% yield

Miyaura borylation conditions then provided cross-coupling partner 2-64 in good yield but contaminated with variable amounts of bis(pinacolborane). The two-step yield after the subsequent cross-coupling was higher when 2-64 was used without purification, thus after workup 2-64 was typically taken directly into the cross-coupling. The double Suzuki cross-coupling of 2-64 with iodoamide 2-17 proceeded as expected with an acceptable 55% yield of 2-65. Finally, the Pd(OAc)₂/X-Phos system effectively cyclized the electron-rich, ortho-substituted compound 2-65 in excellent yield.

After a brief survey of oxidants, it was found that, though more electron rich than diazaanthracene 2-51, 2-53 was still challenging to oxidize. Attempts to deprotect the phenol, which should be more prone to oxidation than the anisole, met with failure. Attempts to follow this synthetic scheme beginning with other protecting groups (e.g., —OMOM, —OBn, —OPBM, —OTHP, —OSEM) surprisingly all failed at various steps. We found that oxidation of 2-53 was possible under forcing conditions. Thus, brief heating of 2-53 in concentrated nitric acid produced SCH 538415 as a bright red-orange solid in 40% yield, along with variable amounts (0-14%) of nitrated product 2-66, the structure of which was confirmed by single-crystal x-ray diffraction. By this route the first total synthesis of the natural product was completed in six steps and 9.7% overall yield from 2,6-dichloroanisole. Spectral data matched that of the natural product.

B. Synthesis of DNQ.

The simplest approach to apply this route to the synthesis of DNQ would involve a selective mono-N-methylation of nor-methyl diazaanthracenol 2-67 (Scheme 1.13). Primary amide 2-70 was synthesized but found to be an unreactive partner in the Suzuki coupling with 2-64. The N-para-methoxybenzyl amide 2-71 was then synthesized in 82% yield from 2-butynoic acid by hydroiodination and treatment of the corresponding acid chloride with p-methoxybenzyl amine (Scheme 1.13). This route was employed because the reaction of ethyl 2-butynoate with p-methoxybenzyl amine resulted primarily in 1,4-addition to the alkyne. The Suzuki cross-coupling of 2-64 with 2-71 produced 2-72 in 42% yield. The subsequent amidation proceeded in quantitative yield to generate the protected tricyclic compound 2-73. Removal of the PMB protecting groups from 2-73 in hot concentrated HBr was rapid and produced 2-67 in 97% yield. We found that methylation of 2-67 was highly unselective, generating a mixture of mono- and di-N- and O-alkylated products.

Although a trace amount of DNQ was isolated by subsequent hydrolysis of o-alkylated products, oxidation in nitric acid, and chromatographic purification, we deemed this route impractical.

Scheme 1.13. Synthesis of DNQ by methylation of 2-67.

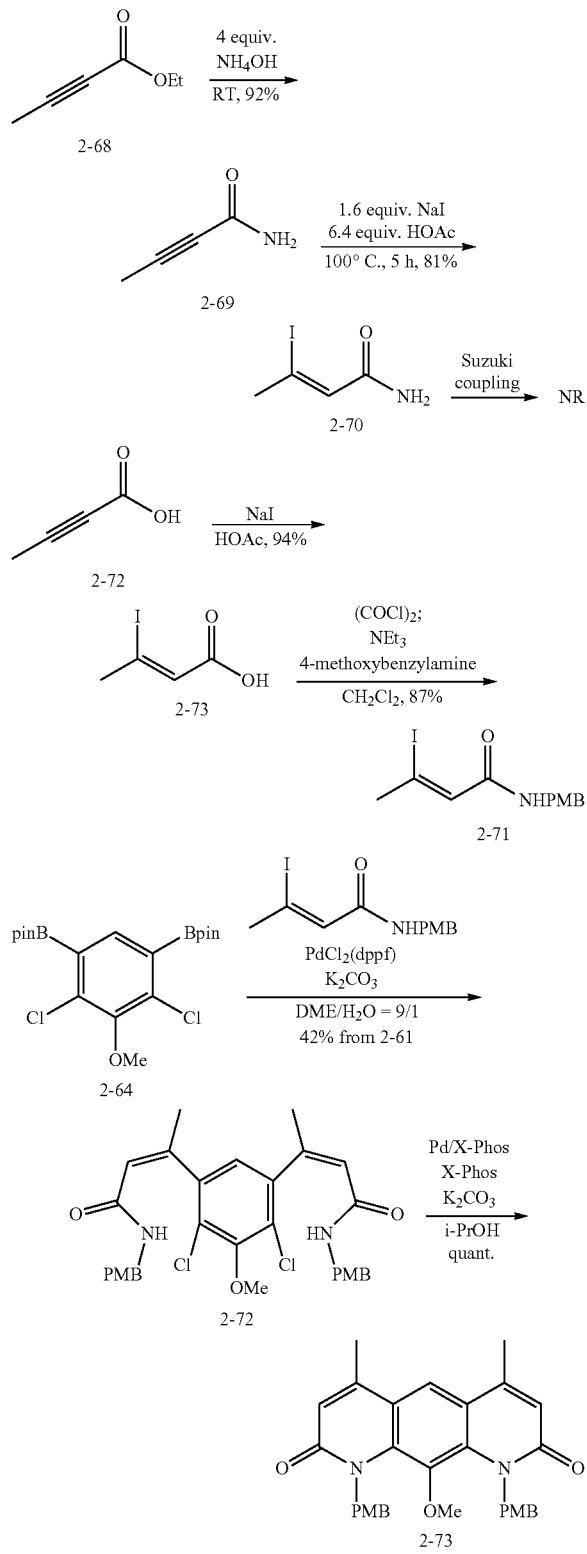

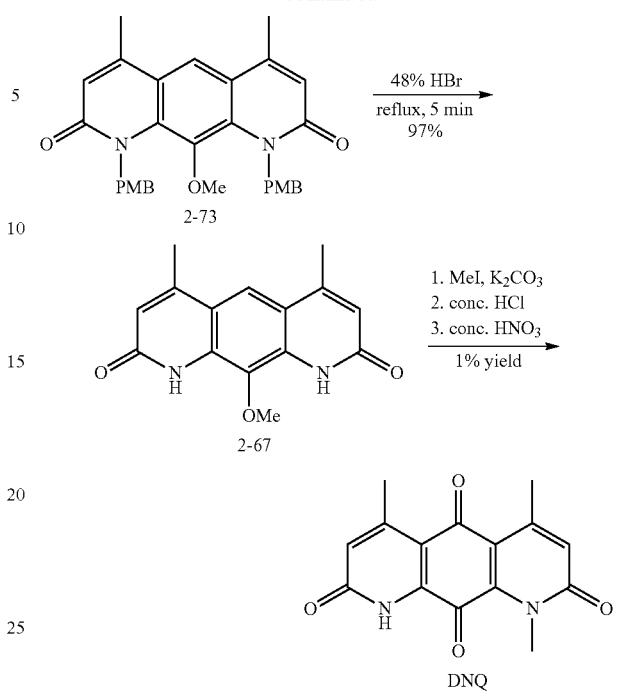

An alternate route to DNQ focused on the synthesis of nonsymmetric diamide 2-74 (Scheme 1.14). Although routes involving iterative Suzuki coupling initially appeared promising, a mixed cross-coupling between bisboronate 2-64 and iodoamides 2-17 and 2-71 was found to be the simplest method to form 2-74. Separation of 2-74 from the accompanying symmetric products was easily effected by chromatography. Aryl amidation under the previously employed conditions efficiently formed tricycle 2-75 along with variable amounts of unprotected amide 2-76. Isolation at this step was unnecessary, as subjection of the crude amidation products to acidic hydrolysis produced 2-77 in 76% yield over two steps. Oxidation of phenol 2-77 was markedly more facile than oxidation of anisole 2-53. Oxidation of 2-77 catalyzed by salcomine under $O_2$ produced DNQ in 77% yield. Overall the synthesis consisted of 7 steps in the longest linear sequence, 12% overall yield. This compares to 11 steps and <0.84% yield for the previous synthesis of DNQ (Rinehart et al. *J. Am. Chem. Soc.* 1961, 83, 3729; Forbis et al., *J. Am. Chem. Soc.* 1973, 95, 5003). By this method, 400 mg of DNQ has been synthesized in a single sequence without encountering any difficulty related to scale.

Scheme 1.14. Robust and scalable synthesis of DNQ.

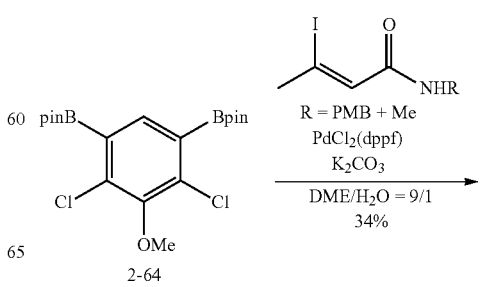

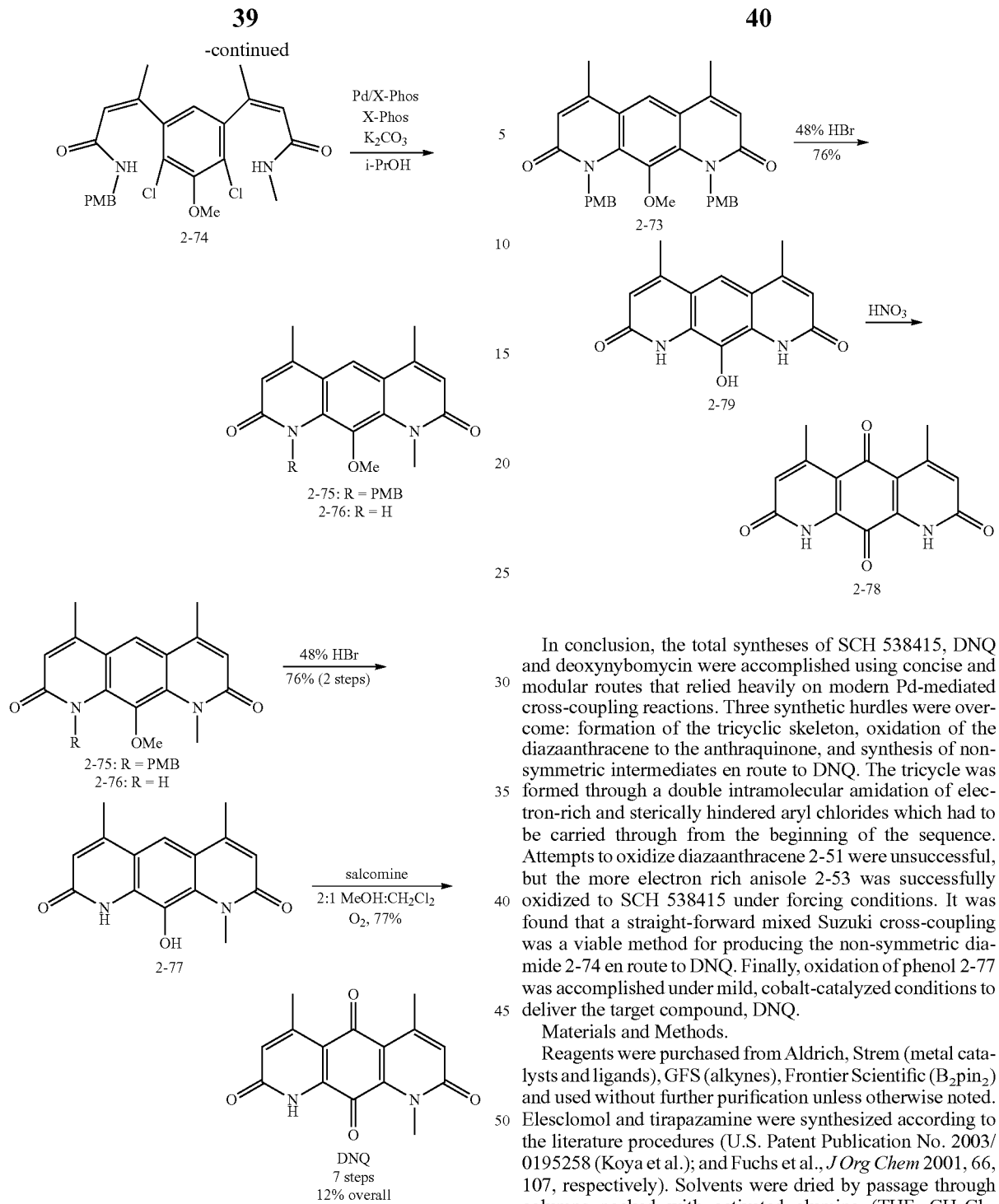

C. Synthesis of Nor-Methyl Anthraquinone 2-78.

Having previously synthesized 2-73 we sought to make the previously-reported nor-methyl DNQ derivative 2-78 for comparison with DNQ and SCH 538415. Unlike for 2-52, heating in HBr over 4 hours also removes the phenol-protecting methyl group from 2-73. Oxidation of diazaanthracenol 2-79 in $HNO_3$ at 60° C. generates a red solution from which a red-orange solid precipitates upon cooling and dilution with water. Compound 2-78 was insoluble in all solvents evaluated except concentrated acids or bases.

In conclusion, the total syntheses of SCH 538415, DNQ and deoxynybomycin were accomplished using concise and modular routes that relied heavily on modern Pd-mediated cross-coupling reactions. Three synthetic hurdles were overcome: formation of the tricyclic skeleton, oxidation of the diazaanthracene to the anthraquinone, and synthesis of non-symmetric intermediates en route to DNQ. The tricycle was formed through a double intramolecular amidation of electron-rich and sterically hindered aryl chlorides which had to be carried through from the beginning of the sequence. Attempts to oxidize diazaanthracene 2-51 were unsuccessful, but the more electron rich anisole 2-53 was successfully oxidized to SCH 538415 under forcing conditions. It was found that a straight-forward mixed Suzuki cross-coupling was a viable method for producing the non-symmetric diamide 2-74 en route to DNQ. Finally, oxidation of phenol 2-77 was accomplished under mild, cobalt-catalyzed conditions to deliver the target compound, DNQ.

Materials and Methods.

Reagents were purchased from Aldrich, Strem (metal catalysts and ligands), GFS (alkynes), Frontier Scientific ($B_2pin_2$) and used without further purification unless otherwise noted. Elesclomol and tirapazamine were synthesized according to the literature procedures (U.S. Patent Publication No. 2003/0195258 (Koya et al.); and Fuchs et al., *J Org Chem* 2001, 66, 107, respectively). Solvents were dried by passage through columns packed with activated alumina (THF, $CH_2Cl_2$, diethyl ether) or activated molecular sieves (DMSO). Amines were freshly distilled over $CaH_2$ under a nitrogen atmosphere. Reactions involving n-BuLi or LDA were performed using standard Schlenk techniques under argon.

$^1$H-NMR and $^{13}$C-NMR spectra were recorded on Varian Unity spectrometers at 500 MHz and 125 MHz, respectively. Spectra generated from a solution of $CDCl_3$ were referenced to residual chloroform ($^1$H: δ 7.26 ppm, $^{13}$C: δ 77.23 ppm). Spectra generated in mixtures of $CDCl_3$ and $CD_3OD$ were referenced to tetramethylsilane ($^1$H: δ 0.00 ppm) or $CD_3OD$ ($^{13}$C: δ 49.0 ppm). Spectra generated from d-TFA were referenced to residual H ($^1$H: δ 11.50 ppm) or $F_3CCO_2D$ ($^{13}$C: δ 164.2 ppm).

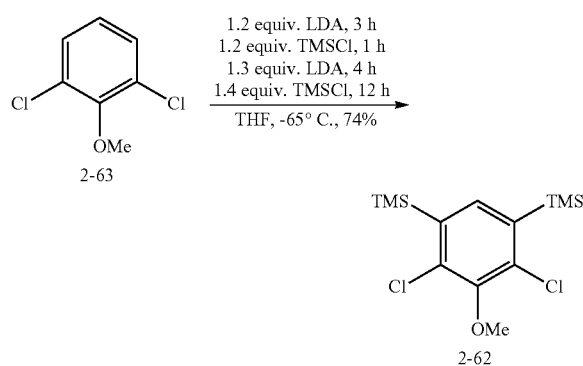

Preparation of LDA: To an oven-dried Schlenk flask was added dry THF (23.2 mL), diisopropylamine (14.0 mL, 99.9 mmol) and a stir bar. After cooling the flask in a dry ice/isopropanol bath, n-BuLi (1.6 M in hexanes, 62.8 mL, 100 mmol) was added dropwise over about 15 minutes. The flask was then transferred to an ice bath for temporary storage.

To an oven-dried 250 mL Schlenk flask and stir bar under argon was added dry THF (50 mL) and 2,6-dichloroanisole (2-63, 5.00 mL, 36.5 mmol). The flask was chilled in a −75° C. bath and freshly prepared LDA (1.0 M, 44 mL, 44 mmol) was added by syringe over 15 minutes. The reaction was stirred for 3.25 h between −65 and −75° C. and was kept in this temperature range for the duration of the reaction. TMSCl (5.60 mL, 43.8 mmol) was then added and the mixture was stirred for 1 h. A second aliquot of LDA (47 mL, 47 mmol) was then added followed, after three more hours, by a second aliquot of TMSCl (6.50 mL, 50.9 mmol). The mixture was allowed to stir and warm overnight and had reached −20° C. after 14 h. The cloudy yellow solution was quenched with 15 mL water, which dissolved the precipitate. The mixture was transferred to a separatory funnel, diluted with 1M HCl (15 mL) and ether (20 mL), and shaken and separated. The aqueous phase was extracted once with ether (1×30 mL), and the combined organic extracts were washed with brine (1×20 mL), dried over MgSO$_4$, filtered, and evaporated to a pale yellow oil which solidified under vacuum. Recrystallization from MeOH/H$_2$O in two crops yielded 7.25 and 1.42 g of 2-62 as white flakes (8.67 g, 27.0 mmol, 74%).

$^1$H-NMR (CDCl$_3$, 500 MHz): δ 7.25 (s, 1H, aryl CH), 3.89 (s, 3H, OCH$_3$), 0.36 (s, 18H, Si(CH$_3$)$_3$). $^{13}$C-NMR (CDCl$_3$, 125 MHz, d1 delay set to 20 sec, dm=nny): δ 151.9, 138.7, 137.0, 136.7, 60.5, −0.5. HRMS (EI) calcd for C$_{13}$H$_{22}$OSi$_2$Cl$_2$ (M)$^+$: 320.0586. found: 320.0583. Melting point: 78.5-80.5° C. IR (cm$^{-1}$, thin film in CDCl$_3$): 2958 (w), 1397 (w), 1342 (m), 1251 (m).

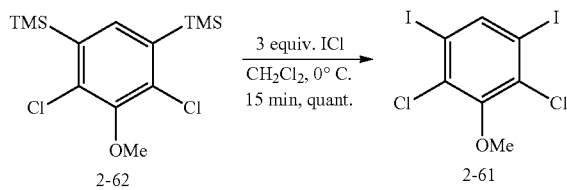 [SMILES: COc1c(Cl)c([Si](C)(C)C)cc([Si](C)(C)C)c1Cl ; COc1c(Cl)c(I)cc(I)c1Cl]

Iodine monochloride (11.41 g, 70.28 mmol) was weighed into a 100 mL round-bottom flask with a stir bar and dissolved in 35 mL CH$_2$Cl$_2$. The flask was chilled on an ice-water bath and 2-62 (7.49 g, 23.3 mmol) was added portion-wise at a slow enough rate to keep the solution temperature below 20° C. After the addition, a thick precipitate formed and more CH$_2$Cl$_2$ (35 mL) was added to dissolve it. Stirring was continued for 0.5 h, after which water (10 mL) was added and NaHSO$_3$ was added by spatula until the color of the solution ceased to fade. The aqueous layer was a clear yellow and the organic layer was colorless. The mixture was poured into a separatory funnel, diluted with water (20 mL) and CH$_2$Cl$_2$ (50 mL), and shaken and separated. The aqueous phase was further extracted with CH$_2$Cl$_2$ (2×15 mL). The combined organic extracts were then washed with brine (1×20 mL), dried over MgSO$_4$, filtered and evaporated to yield 2-61 as a white solid (9.965 g, 23.24 mmol, 99.6%). Product may be recrystallized from hexanes to produce colorless needles.

$^1$H-NMR (CDCl$_3$, 500 MHz): δ 8.14 (s, aryl CH), 3.88 (s, —OCH$_3$). $^{13}$C-NMR (CDCl$_3$, 125 MHz): δ 152.6, 144.3, 135.0, 97.7, 60.8. HRMS (EI) calcd for C$_7$H$_6$OCl$_2$ (M)$^+$: 427.7729. found: 427.7731. Melting point: 138.5-140.5° C. IR (cm$^{-1}$, thin film in CCl$_4$): 1528 (w), 1394 (m), 1361 (s), 1005 (s).

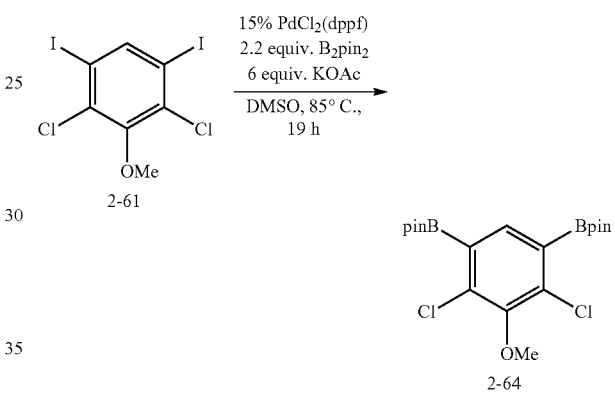

To a hot, oven-dried Schlenk flask with stir bar was added KOAc (1.24 g, 12.6 mmol) and vacuum was applied to dry the salt until the flask was cool. To this flask was added PdCl$_2$(dppf) (0.256 g, 15.0 mol %), B$_2$pin$_2$ (1.17 g, 4.59 mmol) and 2-61 (0.896 g, 2.09 mmol). The flask was evacuated and backfilled with argon (3×). Dry DMSO (12 mL) was added by syringe and the mixture was plunged into an oil bath at 80° C. Color changed from yellow to red to black over five minutes. The mixture was allowed to stir with heating for 19 hours. After cooling, the mixture was poured into a separatory funnel with an additional 5 mL DMSO and then extracted with hexanes (3×100 mL). The combined hexane extracts were washed with water (2×100 mL) until the organic layer was clear. The organic fraction was then dried over MgSO$_4$, filtered, and evaporated to an off-white solid. The crude solid (0.858 g) was a mixture of 6 and B$_2$pin$_2$ (molar ratio ~3:1). The yield of 2-64 was calculated from this ratio to be 79% (712 mg, 1.66 mmol). This material was generally used without purification in the subsequent Suzuki cross couplings. Recrystallization of the mixture from pentane yields pure 2-64 as colorless needles.

$^1$H-NMR (CDCl$_3$, 500 MHz): δ 7.67 (s, 1H, aryl CH), 3.86 (s, 3H, OCH$_3$), 1.37 (s, 24H, C(CH$_3$)$_2$). $^{13}$C-NMR (CDCl$_3$, 125 MHz): δ 152.3, 138.0, 137.1 (2C), 130 (broad, 2C), 84.5 (2C), 60.5, 25.0 (8C). HRMS (ESI-TOF) calcd for C$_{19}$H$_{28}$B$_2$O$_5$Cl$_2$ (M+H)$^+$: 429.1587. found: 429.1591. Melting point: 185-187° C. IR (cm$^{-1}$, thin film in CCl$_4$): 2982 (m), 2935 (w), 1574 (m), 1446 (m), 1362 (s), 1333 (s), 1143 (s), 1033 (m).

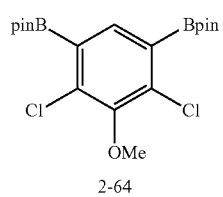

2-64

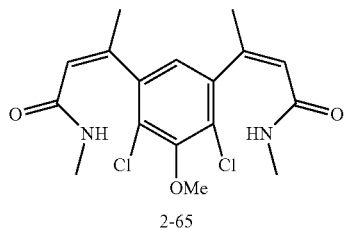

2-65

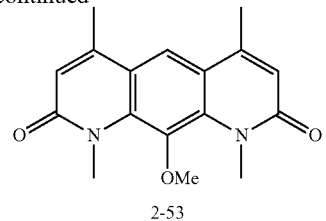

2-53

To a 1-dram vial with a stir bar was added 2-65 (16.3 mg, 0.0440 mmol), $K_2CO_3$ (36.70 mg, 0.266 mmol), Pd/X-Phos (3.25 mg, 10.0 mol %), and X-Phos (2.20 mg, 10.5 mol %). The vial was cycled between vacuum and argon three times and i-PrOH (1.75 mL) was added while flushing the vial with argon. The vial was sealed with a Teflon-lined cap and immersed in an oil bath at 110° C. The reaction was allowed to stir with heating for 16 hours. Insoluble materials were removed by filtration through Celite and rinsed with $CH_2Cl_2$. The filtrate was evaporated and the residue was purified by column chromatography (0-5% MeOH in EtOAc). Compound 2-53 (12.6 mg, 0.0422 mmol, 96%) was isolated as white solid.

To a Schlenk flask with a stir bar was added crude 2-64 (404 mg total mass, estimated 323 mg and 0.755 mmol 2-64), $PdCl_2(dppf)$ (123 mg, 20 mol %), $K_2CO_3$ (627 mg, 4.54 mmol), and 2-17 (510 mg, 2.27 mmol) and the flask was evacuated and backfilled with argon three times. Water (1 mL) and DME (9 mL) were added by syringe after degassing the solvents by bubbling with argon for 45 minutes. The flask was plunged into an oil bath at 80° C. for 3 h. The mixture was poured into a separatory funnel and diluted with water (5 mL). The mixture was extracted with EtOAc (3×20 mL). The combined organic extracts were dried over $MgSO_4$, filtered and evaporated to a deep red oil. The crude product was dissolved in $CH_2Cl_2$ and loaded onto a silica plug (diameter: 48 mm, height: 30 mm) and eluted with EtOAc. The fractions containing 2-65 were evaporated to a red solid. This solid was stirred in 3 mL EtOAc and filtered. The solid was washed twice with 2 mL portions of EtOAc then allowed to dry on the filter. Compound 2-65 was isolated as colorless crystals (152 mg, 0.409 mmol, 55% from estimated 2-64, 43% over two steps from 2-61).

$^1$H-NMR (CDCl$_3$, 500 MHz): δ 6.73 (s, 1H, aryl CH), 5.94 (q, 2H, J=1.5 Hz, vinylic CH), 5.59 (bs, 2H, NH), 3.91 (s, 3H, OCH$_3$), 2.69 (d, 6H, J=4.5 Hz, NCH$_3$), 2.12 (d, 6H, allylic CH$_3$, J=1.0 Hz). $^{13}$C-NMR (CDCl$_3$, 125 MHz): δ 165.8, 145.4, 140.0, 125.5, 124.2, 124.2, 123.3, 61.0, 26.5, 25.4. HRMS (ESI-TOF) calcd for $C_{17}H_{20}N_2O_3Cl_2$ (M+H)$^+$: 371.0929. found: 371.0915. Melting point: Darkened at 210° C., decomposed at 230° C. IR (cm$^{-1}$, thin film in CDCl$_3$): 3383 (w), 3326 (b, w), 2979 (w), 2939 (w), 1663 (m), 1641 (m), 1608 (m), 1525 (m), 1368 (m).

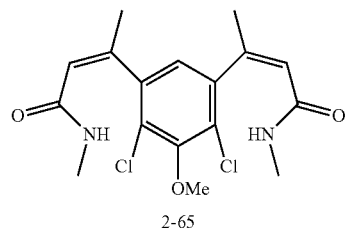

2-65

$^1$H-NMR (CDCl$_3$, 500 MHz): δ 7.68 (s, 1H, aryl CH), 6.57 (d, 2H, J=1.5 Hz, vinyl CH), 3.86 (s, 6H, N—CH$_3$), 3.50 (s, 3H, OCH$_3$), 2.50 (d, 6H, J=1.0 Hz, allylic CH$_3$). $^{13}$C-NMR (CDCl$_3$, 125 MHz): δ 164.1, 146.1, 137.2, 136.3, 120.8, 119.8, 116.9, 62.4, 35.9, 19.2. HRMS (ESI-TOF) calcd for $C_{17}H_{18}N_2O_3$ (M+H)$^+$: 299.1396. found: 299.1385. Melting point: >250° C. IR (cm$^{-1}$, thin film in CDCl$_3$): 2962 (w), 1648 (s), 1619 (m), 1583 (s), 1445 (m), 1394 (m), 1354 (m), 1325 (m), 1035 (m).

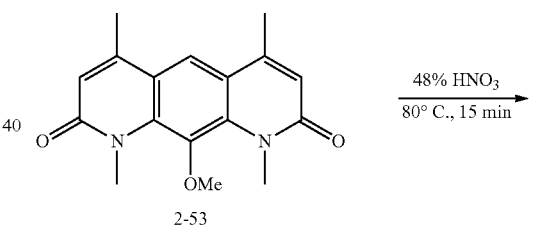

2-53

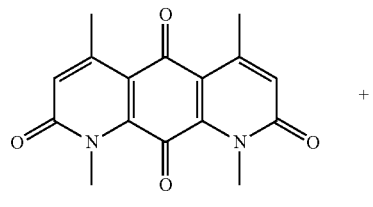

SCH 538415 (2-10)
40%

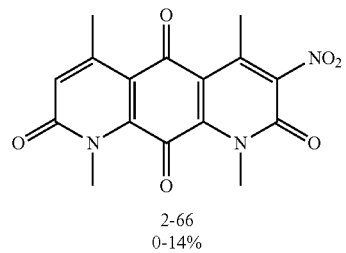

2-66
0-14%

In a 7-mL vial with a stir bar, 2-53 (29.8 mg, 0.100 mmol) was dissolved in conc. HNO$_3$ (3 mL) and the vial was plunged into an oil bath at 80° C. After 15 minutes the flask was removed from heat and the solution was diluted with water (4 mL), transferred to a separatory funnel and extracted with CH$_2$Cl$_2$ (3×10 mL). The aqueous phase was carefully neutralized with 10 M NaOH (a dark color persists when the acid is consumed) and extracted once more with CH$_2$Cl$_2$ (10 mL). The organic extracts were loaded directly onto a silica gel column and eluted with a gradient of 0 to 5% MeOH in EtOAc. Product was isolated as a deep red fraction which was evaporated to a bright red-orange solid. This was dissolved in 5 mL CH$_2$Cl$_2$ and filtered to remove a sparingly soluble yellow material. The filtrate was evaporated to yield SCH 538415 as a bright red-orange solid (11.9 mg, 0.0399 mmol, 40%). Spectral data match the reported natural product. SCH 538415 can be further purified by sublimation (180° C., 300 mtorr).

$^1$H-NMR for 2-10 (CDCl$_3$, 500 MHz): δ 6.65 (d, 2H, J=1.0 Hz, vinyl CH), 3.73 (s, 6H, NCH$_3$), 2.56 (d, 6H, J=1.0 Hz, allylic CH$_3$). $^{13}$C-NMR for 2-10 (CDCl$_3$, 125 MHz): δ 181.5, 178.9, 161.5, 149.1, 143.0, 126.6, 117.0, 34.2, 22.8. HRMS for 2-10 (ESI-TOF) calcd for C$_{16}$H$_{14}$N$_2$O$_4$ (M+H)$^+$: 299.1032. found: 299.1020. Melting point for 2-10: >250° C. IR for 2-10 (cm$^{-1}$, thin film in CDCl$_3$): 1662 (b, w), 1362 (w).
$^1$H-NMR for 2-66 (CDCl$_3$, 500 MHz): δ 6.70 (d, 1H, J=1.0 Hz, vinyl CH), 3.83 (s, 3H, NCH$_3$), 3.74 (s, 3H, NCH$_3$), 2.56 (s: accidental overlap—two separate signals are seen in other spectra, 6H, allylic CH$_3$). $^{13}$C-NMR for 2-66 (CDCl$_3$, 125 MHz): δ 180.4, 177.8, 161.2, 154.3, 148.9, 142.9, 142.5, 140.8, 127.2, 117.8, 115.4, 35.3, 34.2, 22.7, 16.9.

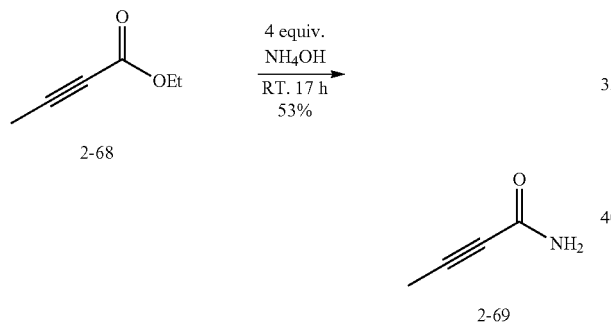

2-68

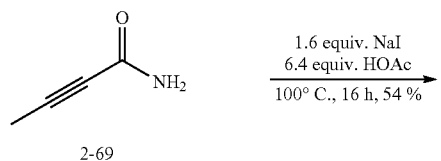

2-69

To a 7 mL vial with stirbar was added ethyl 2-butynoate (506 mg, 4.51 mmol) and concentrated NH$_4$OH (~30%, 1.5 mL, 18 mmol) and the biphasic solution was stirred vigorously for 17 h during which time a thick white precipitate formed. This solid was collected by filtration and dried under vacuum to yield 2-69 as a white solid (198 mg, 2.38 mmol, 53%).

$^1$H-NMR (d$^6$-DMSO, 500 MHz): δ 7.813 (bs, 1H, NH), 7.362 (bs, 1H, NH), 1.91 (s, 3H, CH$_3$). $^{13}$C-NMR (d$^6$-DMSO, 125 MHz): δ 154.4, 82.4, 75.9, 3.0. HRMS (EI) calcd for C$_4$H$_5$NO (M)$^+$: 83.0371. found: 83.0370. MP: 151-152.5° C. IR (cm$^{-1}$, thin film in CDCl$_3$): 1665 (w), 1583 (w), 1369 (w).

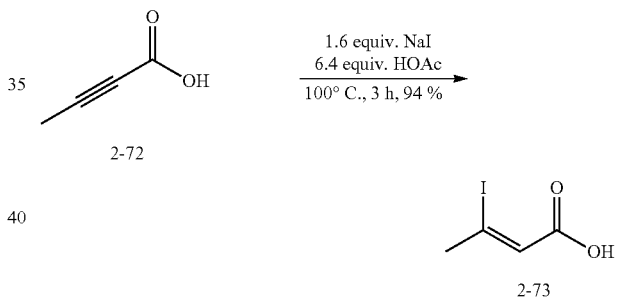

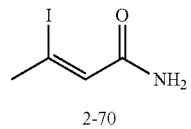

2-70

To a 1-dram vial with a stir bar was added 2-69 (118 mg, 1.41 mmol), NaI (337 mg, 2.25 mmol), and acetic acid (0.52 mL, 9.1 mmol). The vial was closed with a screw-on cap and plunged into a preheated oil bath at 100° C. for 16 h. The deep red reaction mixture was diluted with water (20 mL) and EtOAc (20 mL), treated with NaHSO$_3$ until the color stopped fading (pale yellow), then neutralized with 8 mL 1M NaOH. This mixture was poured into a separatory funnel and the aqueous layer was extracted with EtOAc (1×10 mL). The combined organic layers were washed with sat. NaHCO$_3$ (1×10 mL) and brine (1×10 mL), dried over MgSO$_4$, and evaporated to yield 162 mg (0.765 mmol, 54%) of 2-70 as a white flakey solid.

$^1$H-NMR (CDCl$_3$, 500 MHz): δ 6.28 (d, 1H, J=1.0 Hz, vinyl CH), 5.80 (bs, 2H, NH$_2$), 2.69 (d, 3H, J=1.0 Hz, allylic CH$_3$). $^{13}$C-NMR (CDCl$_3$, 100 MHz): δ 165.4, 128.7, 105.7, 35.3. HRMS (ESI-TOF) calcd for C$_4$H$_6$NOI (M+H)$^+$: 211.9572. found: 211.9582. Melting point: 87-92° C. IR (cm$^{-1}$, thin film): 3332 (s), 3167 (s), 1665 (s), 1622 (s), 1425 (m), 1403 (s), 1260 (m).

To a flask containing 2-butynoic acid (0.503 g, 5.98 mmol), NaI (1.434 g, 9.57 mmol) and a stir bar was added glacial acetic acid (2.2 mL, 38 mmol) and the flask was immersed in an oil bath at 115° C. for 3 h. The reaction mixture was poured into a separatory flask and diluted with water (10 mL) and ether (10 mL). NaHSO$_3$ was added until the color of the solution faded to a pale yellow, then the mixture was shaken and separated. The aqueous fraction was extracted with ether (3×10 mL) then the combined organic fractions were dried over MgSO$_4$ and evaporated to yield 2-73 as a white solid (1.19 g, 5.59 mmol, 94%). Acid 2-73 can be recrystallized with good recovery from CHCl$_3$/heptane to yield large prismatic crystals.

$^1$H-NMR (CDCl$_3$, 500 MHz): δ 12.19 (bs, 1H, COOH), 6.36 (d, 1H. J=1.5 Hz, vinyl CH), 2.77 (d, 3H, J=1.0 Hz, allylic CH$_3$). $^{13}$C-NMR (CDCl$_3$, 125 MHz): δ 169.8, 125.4, 117.1, 37.3. HRMS (ESI-TOF) calcd for C$_4$H$_5$O$_2$I (M+Na)$^+$: 234.9232. found: 234.9234. Melting point: 113-115° C. IR (cm$^{-1}$, thin film in CDCl$_3$): 2978 (b, m), 2702 (m), 2589 (m), 2506 (m), 1699 (s), 1619 (s), 1434 (m), 1406 (m), 1303 (m), 1222 (s).

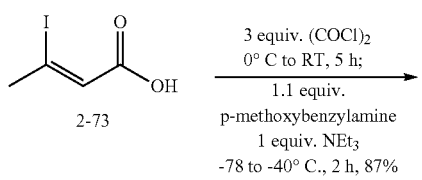

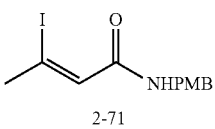

To an oven-dried 40 mL I-Chem vial with a stirbar was added 2-73 (1.03 g, 4.85 mmol) and the flask was evacuated and backfilled with argon. Dry CH$_2$Cl$_2$ (12 mL) was added and the solution was chilled on an ice-water bath. Oxalyl chloride (1.25 mL, 14.3 mmol) was added by syringe and the cold bath was removed. After 5 h at room temperature the volatile components were evaporated directly from the vial. Dry CH$_2$Cl$_2$ (10 mL) was added to the residual oil and the vial was chilled on a dry ice/isopropanol bath. Freshly distilled p-methoxybenzyl amine (740 mg, 5.39 mmol) was added dropwise by syringe followed by NEt$_3$ (0.675 mL, 4.85 mmol). The mixture was allowed to warm to −40° C. after 2 h, then 1 M HCl (20 mL) was added and the solution was poured into a separatory funnel with CH$_2$Cl$_2$ (10 mL). Shaken and separated. The aqueous fraction was extracted with CH$_2$Cl$_2$ (4×10 mL) then dried over MgSO$_4$ and evaporated to a white solid. The solid was slurried in 50 mL ether and hot filtered through Celite. The filtrate was diluted with 50 mL hexanes and heated to reflux until crystallization began. After cooling, pale tan crystals of 2-71 were collected by filtration (1.23 g). The mother liquor was purified by column chromatography (hexanes/EtOAc=2/1) then recrystallized from ether/hexanes to yield additional product as white needles (169 mg). Total 2-71: 1.40 g, 4.24 mmol, 87%.

$^1$H-NMR (CDCl$_3$, 500 MHz): δ 7.20 (d, 2H, J=8.0 Hz, aryl CH), 6.82 (d, 2H. J=8.0 Hz, aryl CH), 6.35 (bs, 1H, NH), 6.23 (q, 1H, J=1.5 Hz, vinylic CH), 4.37 (d, 2H, J=3.5 Hz, NCH$_2$), 3.75 (s, 3H, OCH$_3$), 2.61 (d, 3H, J=1.5 Hz, allylic CH$_3$). $^{13}$C-NMR (CDCl$_3$, 125 MHz): δ 164.7, 159.1, 130.0, 129.5, 128.9, 114.1, 106.5, 55.4, 43.1, 35.9. HRMS (ESI-TOF) calcd for C$_{12}$H$_{13}$NO$_2$I (M+H)$^+$: 332.0148. found: 332.0154. Melting point: 95-98° C. IR (cm$^{-1}$, thin film in CDCl$_3$): 3436 (w), 3311 (bw), 2959 (w), 2838 (w), 1656 (m), 1513 (s), 1465 (w), 1302 (w), 1250 (m), 1176 (m), 1088 (w), 1035 (m).

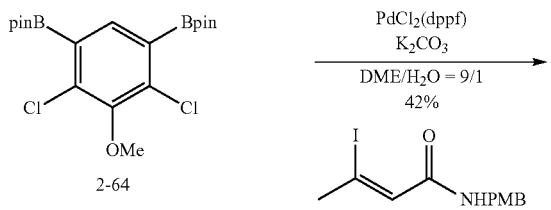

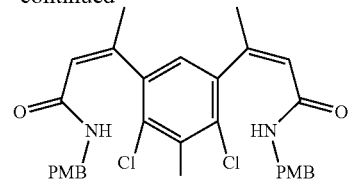

To a 7-mL vial with a stir bar was added crude 2-64 (97 mg total mass, estimated 81 mg and 0.19 mmol 2-64), PdCl$_2$(dppf) (30.6 mg, 0.038 mmol, 20 mol %), K$_2$CO$_3$ (156 mg, 1.13 mmol), and 2-71 (155 mg, 0.468 mmol) and the vial was evacuated and backfilled with argon three times. Water (1 mL) and DME (9 mL) were added by syringe after degassing the solvents by bubbling with argon for 45 minutes. The flask was plunged into an oil bath at 87° C. for 2 h. The mixture was poured into a separatory funnel and diluted with water (5 mL). The mixture was extracted with EtOAc (2×5 mL). The combined organic extracts were dried over MgSO$_4$, filtered and evaporated to a deep red oil. The crude product was dissolved in CH$_2$Cl$_2$ and purified by silica gel chromatography. The product was further purified by recrystallization from chloroform/heptanes. Compound 2-72 was isolated a microcrystalline solid (57.4 mg, 0.098 mmol, 42% over two steps from 2-61).

$^1$H-NMR (CDCl$_3$, 500 MHz): δ 6.99 (bs, 4H), 6.76-6.74 (m, 5H), 5.97 (d, 2H, J=1.5 Hz, vinylic CH), 6.0-5.3 (bd, 2H), 4.3-4.1 (bd, 4H), 3.75 (s, 6H, OCH$_3$), 3.72 (s, 3H, OCH$_3$), 2.09 (bs, 6H, allylic CH$_3$). $^{13}$C-NMR (CDCl$_3$, 125 MHz): δ 165.1, 159 (bs), 145.3, 140 (bs), 131 (bs), 129.0, 125.6, 124.3, 123.5 (bs), 114.0, 60.8, 55.5, 42.9, 25.5.

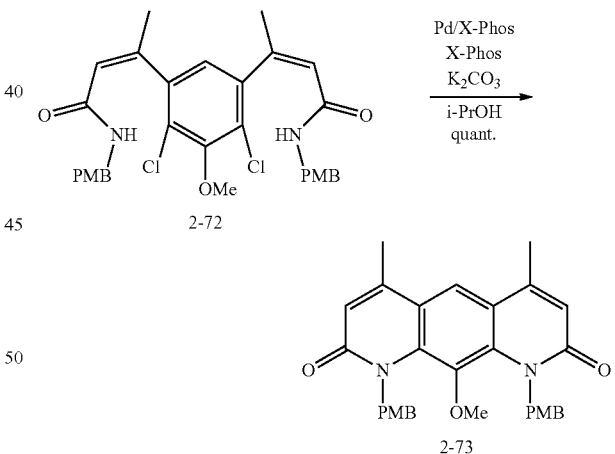

To a 1-dram vial with a stir bar was added 2-72 (29.4 mg, 0.0504 mmol), K$_2$CO$_3$ (42.2 mg, 0.305 mmol), and Pd/X-Phos (6.1 mg, 0.005 mmol, 10.0 mol %). The vial was cycled between vacuum and argon and i-PrOH (1.5 mL) was added while flushing the vial with argon. The vial was sealed with a Teflon-lined cap and immersed in an oil bath at 85° C. The reaction was allowed to stir with heating for 14.5 hours. The solvent was evaporated and the residue was purified by column chromatography (0-100% EtOAc in hexanes). Compound 2-73 (23 mg, quant.) was isolated an oily solid.

$^1$H-NMR (CDCl$_3$, 500 MHz): δ 7.62 (s, 1H, aryl CH), 7.01 (bd, 4H, J=7.5 Hz), 6.74 (d, 4H, J=8.0 Hz) 6.58 (s, 2H, vinyl CH), 5.9-5.4 (bs, 2H), 5.2-5.4 (bd, 4H), 3.72 (s, 6H, OCH$_3$), 2.9 (bs, 3H), 2.48 (s, 6H, allylic CH$_3$).

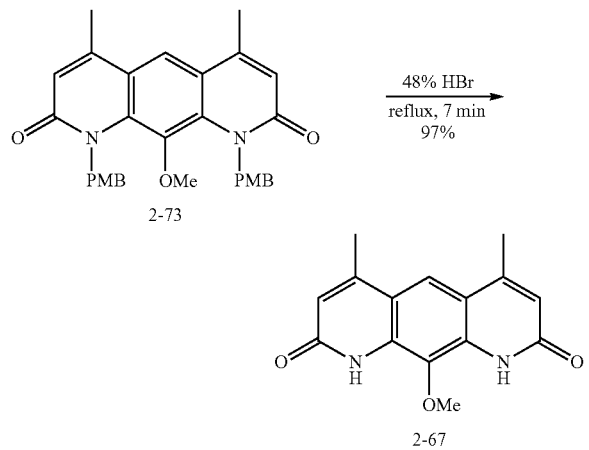

2-73 (200 mg, 0.390 mmol) was slurried in 48% HBr (8 mL) and heated in an oil bath at 115° C. for 7 minutes. The reaction was diluted to 50 mL with water and the product was collected by filtration and washing with water and EtOAc. 2-67 was collected as a light yellow solid (102 mg, 0.378 mmol, 97%). $^1$H-NMR (2:1 CDCl$_3$:CD$_3$OD, 500 MHz): δ 7.82 (s, 1H, aryl CH), 6.51 (d, 2H, J=1.5 Hz, vinyl CH), 3.94 (s, 3H), 2.59 (d, 6H, J=1.5 Hz, allylic CH$_3$).

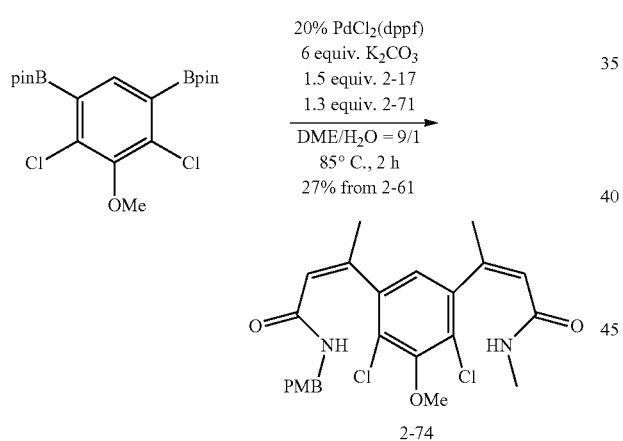

To a 40 mL I-Chem vial was added crude 2-64 (750 mg, 1.45 mmol), PdCl$_2$(dppf) (239.1 mg, 20 mol %), K$_2$CO$_3$ (1.20 g, 8.69 mmol), 2-17 (490.3 mg, 2.18 mmol), and 2-71 (625.4 mg, 1.89 mmol) and the vial was capped with a screw-on lid with a septum and evacuated and backfilled with argon. Water (1 mL) and DME (10 mL) were added by syringe after degassing the solvents by bubbling with argon for 30 minutes. The flask was immersed in an oil bath at 90° C. for 2.5 hours. The mixture was allowed to cool and then was poured into a separatory funnel, diluted with water (25 mL) and extracted with EtOAc (3×20 mL). The combined organic extracts were washed with brine (1×15 mL), dried over MgSO$_4$, filtered and evaporated. The residue was purified by column chromatography (4:1 EtOAc:hexanes) to yield 2-74 as a pale yellow foam (231 mg, 0.484 mmol, 34% yield from estimated 2-64, 27% over two steps from 2-61).

$^1$H-NMR (CDCl$_3$, 500 MHz): δ 7.03 (bs, 2H, PMB CH), 6.74 (d, 3H, J=8.0 Hz, PMB CH and aryl CH), 6.55 (bs, 1H, NH), 5.99 (bs, 1H, NH), 5.96 (s, 1H, vinyl CH), 5.92 (s, 1H, vinyl CH), 4.20 (bd, 2H, J=29 Hz, benzyl CH$_2$), 3.79 (s, 3H), 3.73 (s, 3H), 2.57 (d, 3H, J=3.5 Hz, NCH$_3$), 2.09 (s, 3H, allyl CH$_3$), 2.07 (bs, 3H, allyl CH$_3$). $^1$H-NMR (CDCl$_3$, 60° C., 500 MHz): δ 7.02 (bd, 2H, J=6.5 Hz, PMB CH), 6.75 (d, 2H, J=8.0 Hz, PMB CH), 6.74 (s, 1H, aryl CH), 6.3 (bs, 1H, NH), 5.97 (s, 1H, vinyl CH), 5.93 (s, 1H, vinyl CH), 5.87 (bs, 1H, NH), 4.21 (bs, 2H, benzyl CH$_2$), 3.80 (s, 3H), 3.73 (s, 3H), 2.58 (d, 3H, J=4.5 Hz, NCH$_3$), 2.09 (s, 6H, allyl CH$_3$), 2.06 (s, 3H, allyl CH$_3$). $^{13}$C-NMR (CDCl$_3$, 60° C., 125 MHz): δ 165.9, 165.1, 159.1, 153.5, 145.4, 144.6, 140.2, 140.1, 131.1, 128.9, 125.6, 125.5, 124.5, 124.3, 123.5, 114.2, 60.7, 55.4, 42.9, 26.3, 25.2 (2C). HRMS (ESI-TOF) calcd for C$_{24}$H$_{26}$Cl$_2$N$_2$O$_4$ (M+H)$^+$: 477.1348. found: 477.1331. Melting point: 157-162° C. IR (cm$^{-1}$, thin film in CDCl$_3$): 3404 (w), 2940 (w), 1663 (w), 1613 (w), 1514 (m), 1369 (w), 1249 (w), 1029 (w).

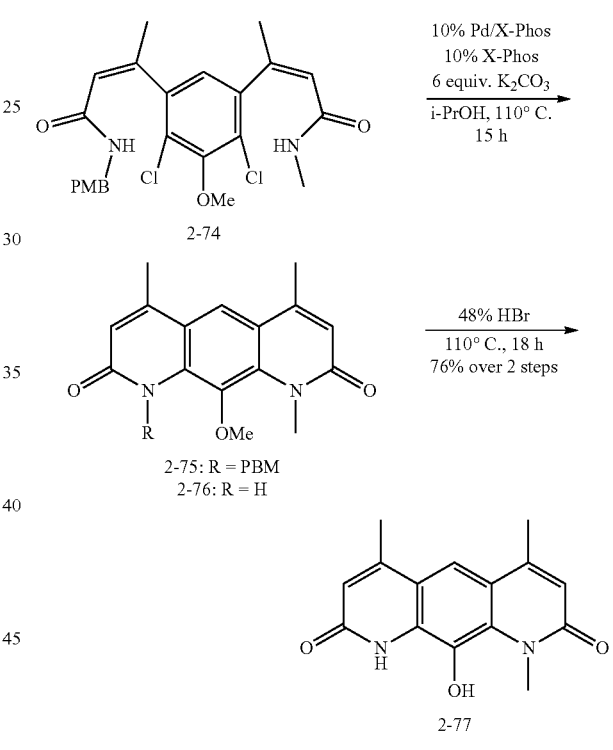

To a 1-dram vial with a stir bar was added 2-74 (39.9 mg, 0.0835 mmol), K$_2$CO$_3$ (69.9 mg, 0.506 mmol), Pd/X-Phos (6.15 mg, 10.0 mol %), and X-Phos (4.03 mg, 10.1 mol %). The vial was cycled between vacuum and argon three times and i-PrOH (3.4 mL) was added while flushing the vial with argon. The vial was sealed with a Teflon-lined cap and immersed in an oil bath at 110° C. The reaction was allowed to stir with heating for 15 hours. After cooling, insoluble materials were removed by filtration through Celite and rinsing with CH$_2$Cl$_2$. At this point 2-75 can be isolated in >95% yield by chromatographic purification with 0 to 2.5% MeOH in EtOAc.

$^1$H-NMR (CDCl$_3$, 500 MHz): δ 7.64 (s, 1H, anisole CH), 7.09 (d, 2H, J=8.5 Hz, PMB CH), 6.73 (d, 2H, J=8.5 Hz, PMB CH), 6.65 (d, 1H, J=1.0 Hz, vinyl CH), 6.52 (d, 1H, J=1.0 Hz, vinyl CH), 5.30 (bd, 2H, benzyl CH$_2$), 3.72 (s, 3H), 3.65 (s, 3H), 3.25 (bs, 3H), 2.52 (d, 3H, J=1.0 Hz, allylic CH$_3$), 2.46 (d, 3H, J=1.5 Hz, allylic CH$_3$).] The filtrate was evaporated and a stir bar and 2 mL 48% HBr were added. The flask was immersed in an oil bath at 110° C. [After 5 minutes of heating, 2-76 can be isolated in >95% yield by dilution of the acid in water and collection of the resulting precipitate. $^1$H-NMR (2:1 CDCl$_3$:CD$_3$OD, 500 MHz): δ 7.84 (s, 1H, aryl CH), 6.58 (d, 1H, J=1.5 Hz, vinyl CH), 6.55 (d, 1H, J=1.5 Hz, vinyl CH), 3.98 (s, 3H), 3.82 (s, 3H), 2.61 (d, 3H, J=1.0 Hz, allylic CH$_3$), 2.57 (d, 3H, J=1.5 Hz, allylic CH$_3$). $^{13}$C-NMR (CDCl$_3$, 125 MHz): δ 164.7, 164.0, 149.9, 148.0, 134.7, 134.2, 133.9, 120.5, 120.1, 119.7, 117.8, 117.6, 62.8, 34.2, 19.5, 19.1. HRMS (ESI-TOF) calcd for C$_{16}$H$_{16}$N$_2$O$_3$ (M+H)$^+$: 285.1239. found: 285.1226].

After 17 hours the reaction was removed from heat. The mixture was carefully rendered basic over an ice bath by adding 10 M NaOH until the precipitate dissolved into a yellow solution. The residual solid was removed by filtration through hardened filter paper and discarded. The filtrate was rendered acidic with 1 M HCl, whereupon a colloidal precipitate formed. The mixture was then centrifuged (3220×g for 5 minutes). The resulting semi-compact gelatinous solid was collected by filtration through hardened filter paper and dried to a constant mass under vacuum to yield 17.2 mg of 2-77 as light brown solid (17.2 mg, 0.0636 mmol, 76% over 3 steps).

$^1$H-NMR (d-TFA, 500 MHz): δ 8.37 (s, 1H, aryl CH), 7.20 (s, 1H, vinyl CH), 7.03 (s, 1H, vinyl CH), 4.38 (s, 3H, NCH$_3$), 2.78 (s, 3H, allylic CH$_3$), 2.75 (s, 3H, allylic CH$_3$). $^{13}$C-NMR (d-TFA, 125 MHz): δ 167.2, 166.6, 160.4, 159.3, 135.7, 134.9, 133.6, 125.2, 123.6, 120.4, 119.9, 116.1, 39.6, 20.9, 20.2. HRMS (ESI-TOF) calcd for C$_{15}$H$_{14}$N$_2$O$_3$ (M+H)$^+$: 271.1083. found: 271.1076. Melting point: >250° C. IR (cm$^{-1}$, thin film in CDCl$_3$): 3156 (b, m), 1674 (s), 1651 (s), 1589 (m), 1562 (m), 1432 (w), 1378 (m), 1351 (m), 1332 (m), 1052 (w).

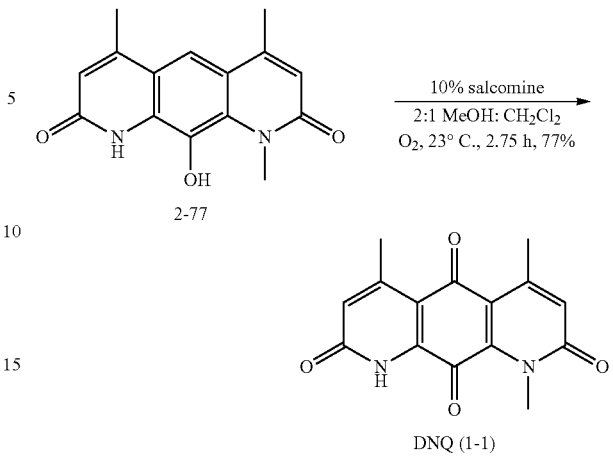

To a 7-mL vial containing 2-77 (17.2 mg, 0.0636 mmol), salcomine (2.08 mg, 0.0064 mmol), and a stir bar was added MeOH (4 mL) and CH$_2$Cl$_2$ (2 mL). A balloon containing O$_2$ was fitted over the mouth of the vial and the slurry was stirred at room temperature. The solid dissolved after about 30 minutes. After 2.75 h stirring, the solvent was evaporated and the residue was purified by silica gel chromatography (6% MeOH in CH$_2$Cl$_2$). DNQ was collected as a bright pink-red solid (13.9 mg, 0.0489 mmol, 77%). Product can be further purified by sublimation (200° C., 300 mtorr).

$^1$H-NMR (d$^5$-pyridine, 500 MHz): δ 6.81 (s, 1H, vinyl CH), 6.76 (s, 1H, vinyl CH), 4.97 (bs, NH), 3.99 (s, 3H, NCH$_3$), 2.57 (d, 3H, allylic CH$_3$), 2.53 (d, 3H, allylic CH$_3$). HRMS (ESI-TOF) calcd for C$_{15}$H$_{12}$N$_2$O$_4$ (M+H)$^+$: 285.0875. found: 285.0864. Melting point: >250° C. IR (cm$^{-1}$, thin film in CDCl$_3$): 1656 (b, w), 1585 (w), 1469 (w), 1397 (w), 1379 (w), 1344 (w), 1290 (w), 1098 (w).

Example 2

Analysis of DNQ and DNQ Derivatives

TABLE 1

Properties of Various Compounds and Compositions of the invention.

| A: ID | B: MCF7 IC$_{50}$ (μM) | C: Fold Protection of MCF7 cells w/ 25 μM dicoumarol | D: NQO1 Initial Velocity @ 1 μM | E: NQO1 K$_m$ (μM) | F: NQO1 V$_{max}$ (μmol/min/ μmol protein) | G: Catalytic Efficiency (M$^{-1}$*s$^{-1}$) | H: DMSO solubility (mM) | I: CH$_2$Cl$_2$ solubility (mM) | J: THF solubility (mM) | K: CH$_2$Cl$_2$: MeOH 2:1 solubility (mM) | L: Binding Energy (kcal/mol) |
|---|---|---|---|---|---|---|---|---|---|---|---|
| DNQ | 0.19 | 7.8 | 1900 ± 100 | 1.0 ± 0.1 | 4000 ± 100 | 6.7E + 07 | 3.1 | 0.7 | 0.42 | 8.5 | 14 |
| SCH | 3.9 | 3.5 | 32 ± 2 | 10.6 ± 0.4 | 402 ± 6 | 6.3E + 05 | 15 | 25 | 3.7 | 60 | 8 |
| 87 | 0.25 | 6.1 | 1900 ± 200 | 1.2 ± 0.1 | 4400 ± 100 | 6.1E + 07 | 110 | 180 | 34 | 140 | 17 |
| 251 | 0.27 | 5.5 | 2100 ± 300 | 0.89 ± 0.12 | 4200 ± 200 | 7.9E + 07 | 10 | 7.6 | 6.1 | 30 | 18 |
| 107 | 0.28 | 4.5 | 1400 ± 100 | 2.1 ± 0.2 | 4200 ± 100 | 3.3E + 07 | 31 | 5.5 | 4.7 | 37 | 28 |
| 109 | 0.53 | 4.5 | 1500 ± 100 | 2.7 ± 0.2 | 5000 ± 200 | 3.1E + 07 | 24 | 9.5 | 18 | 19 | 14 |
| 129 | 0.77 | 2.8 | 1300 ± 200 | 1.4 ± 0.1 | 3000 ± 100 | 3.6E + 07 | 14 | 24 | 17 | 75 | 18 |
| 253 | 0.93 | 2.8 | 600 ± 100 | 3.6 ± 0.2 | 4400 ± 100 | 1.4E + 07 | 10 | 6.1 | 4.6 | 18 | 21 |
| 255 | 3.4 | 1.6 | 250* | 6.4* | 1900* |  | 4.2 | 2 |  | 10 |  |
| 271 | 5 | 1.2 | 250 ± 20 | 3.9 ± 0.5 | 1070 ± 80 | 4.6E + 06 | 21 | 10 | 6.2 | 46 | 14 |
| 131 | 6.3 | 1.1 | 350 ± 10 | 4.2 ± 0.6 | 1600 |  | 10 | 17 | 12 | 49 | 10 |
| 37 | 36 | 0.9 | 75 ± 4 | 1.5 ± 0.3 | 200 ± 20 | 2.2E + 06 | 7.1 | 35 | 17 | 64 | 4 |
| 127 | 8 | ND | 320 ± 60 | 1.4 ± 0.1 | 750 ± 20 | 8.9E + 06 | 1.2 | 34 | 19 | 34 | 32 |
| 9-253 | 0.11 ± 0.04 | 9 | 1700 ± 100 | 1.9 ± 0.1 | 5600 ± 200 | 4.9E + 07 | 16 | 23 | 20 | 100 | 10 |
| 9-281 | 0.79 ± 0.1 | 4 | 1600 ± 200 | 2.7 ± 0.1 | 6300 ± 100 | 3.9E + 07 | 24 | 0.3 | 0.67 | 11 | 10 |
| 9-251 | 0.19 ± 0.02 | 8 | 2000 ± 100 | 1.2 ± 0.2 | 4800 ± 200 | 6.7E + 07 | 15 | 31 | 23 | 120 | 16 |
| 9-249 | 0.15 ± 0.03 | 12 | 2100 ± 90 | 1.1 ± 0.1 | 4800 ± 200 | 7.3E + 07 | 8.6 | 9.7 | 8.8 | 58 | 17 |
| DNQ-2 (10-41) | 0.12 ± 0.01 | 10 | 1590 ± 70 | 1.5 ± 0.2 | 4100 ± 200 | 4.6E + 07 | 8.9 | 3.9 | 3.4 | 32 | 20 |

TABLE 1-continued

Properties of Various Compounds and Compositions of the invention.

| A: ID | B: MCF7 IC$_{50}$ (μM) | C: Fold Protection of MCF7 cells w/ 25 μM dicoumarol | D: NQO1 Initial Velocity @ 1 μM | E: NQO1 K$_m$ (μM) | F: NQO1 V$_{max}$ (μmol/min/ μmol protein) | G: Catalytic Efficiency (M$^{-1}$*s$^{-1}$) | H: DMSO solubility (mM) | I: CH$_2$Cl$_2$ solubility (mM) | J: THF solubility (mM) | K: CH$_2$Cl$_2$:MeOH 2:1 solubility (mM) | L: Binding Energy (kcal/mol) |
|---|---|---|---|---|---|---|---|---|---|---|---|
| 9-255 | 0.19 ± 0.01 | 11 | 1700 ± 40 | 1.3 ± 0.1 | 3900 ± 100 | 5.0E + 07 | 17 | 22 | 16 | 95 | 12 |
| 9-257 | 0.26 ± 0.04 | 11 | 1850 ± 60 | 1.0 ± 0.1 | 3500 ± 100 | 5.8E + 07 | 18 | 32 | 27 | 140 | 13 |
| 2—77 | 0.22 ± 0.01 | 6 | 1260 ± 40 | 2.8 ± 0.2 | 4700 ± 100 | 2.8E + 07 | 25 | 13 | 8.1 | 51 | 13 |
| 2--99 | 0.23 ± 0.02 | 9 | 970 ± 20 | 3.58 ± 0.08 | 4320 ± 40 | 2.0E + 07 | 21 | 5.6 | 7.4 | 46 | 11 |
| 10--47 | | | | | | | 16 | 11 | 3.9 | 35 | 14 |
| 8-255 | 3.4 | 1.6 | 280 ± 40 | 4.4 ± 0.6 | 1540 ± 80 | 5.9E + 06 | 4.2 | 2 | | 10 | 19 |
| 10--53 | | | | | | | <0.1 | 1.5 | 1.8 | 5.9 | 24 |
| 10--51 | | | | | | | <0.1 | 1.8 | 1.8 | 6.4 | 21 |
| 2--97 | 0.83 ± 0.13 | 5 | 700 ± 200 | 3.1 ± 0.3 | 3200 ± 100 | 1.7E + 07 | 71 | 120 | 87 | 79 | 30 |
| β-lap | 3.7 | 2.1 | 150 | | | | 170 | 1650 | 660 | 1400 | |
| MMC | 14 | 1 | | | | | | | | | |
| RH1 | 0.21 | 0.85 | | | | | | | | | |

Example 3

Figure 3:
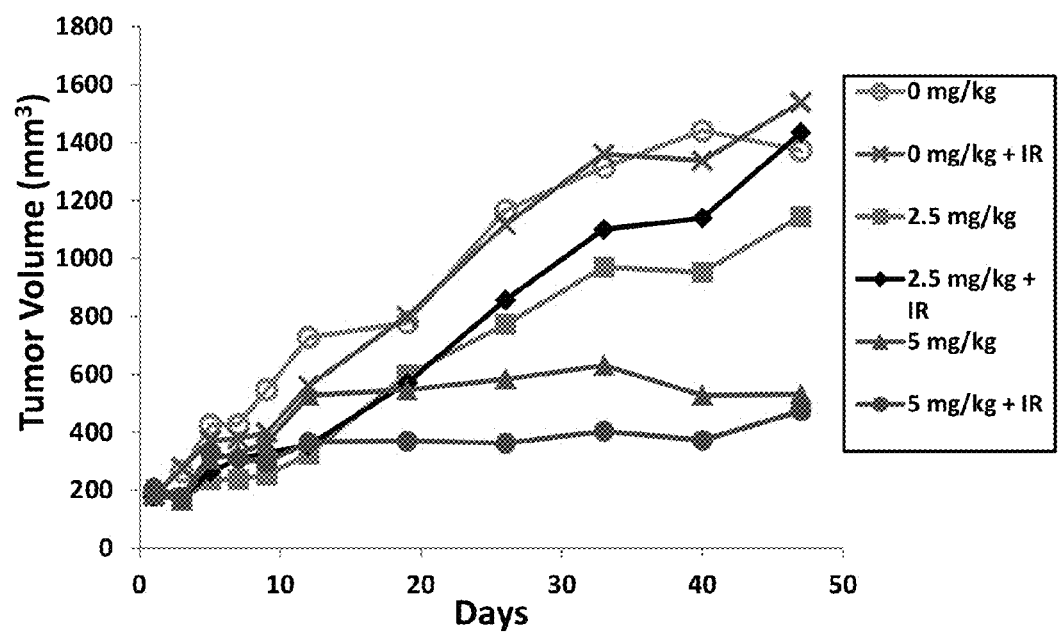
FIG. 3. Nude mice were inoculated with A549 cells and tumors were allowed to establish and grow to 200 mm$^3$. Mice were divided into 6 cohorts (4 mice per cohort) and treated on days 1, 3, 5, 7, and 9. Tumor volumes were measured by caliper.

Antitumor Effect in A549 Lung Cancer Xenograft in Nude Mice and Potentiation of Radiation A formulation of DNQ in HPβCD was sufficiently concentrated to dose at reasonable levels in mice (~10 mg/kg from a 200 μL injection). We are actively experimenting with DNQ in mouse models of cancer. The Boothman lab has completed a pilot study of DNQ in an A549 subcutaneous xenograft model in nude mice (Blanco et al., *Cancer Res.* 2010, 70, 3896). Because β-lap has been shown to potentiate the effect of ionizing radiation, and because DNQ and β-lap have similar mechanisms of cytotoxicity, mice were treated with or without ionizing radiation to determine if DNQ also potentiates the effect of radiation (FIG. 3).

Athymic nude mice were inoculated with A549 NSCLC cells and established tumors were allowed to grow to ~200 mm$^3$. Mice were assigned to one of six treatment groups—four mice per group. Three groups received DNQ (0, 2.5, or 5 mg/kg) by tail vein injection on days 1, 3, 5, 7, and 9. The doses of DNQ were chosen based on the observation that 10 mg/kg DNQ elicited adverse reactions in mice. The other three groups received the same DNQ regimen and also received 2 grays of ionizing radiation on each treatment day. Tumor volumes were measured over the subsequent weeks (FIG. 3).

Because each treatment group comprised only four animals, the statistical significance of the results is low. However, an examination of the average trends in FIG. 3 indicates that both groups that received 5 mg/kg DNQ experienced a slower the rate of tumor growth relative to control. With these exciting preliminary results in hand, mouse models of cancer with full-size treatment groups are being pursued.

The maximum tolerated dose (MTD) of DNQ in mice contained a similar concentration of HPβCD to the MTD of β-lap. Although HPβCD is tolerated at very high doses by IP injection (>5 g/kg), the MTD of HPβCD by IV injection for mice has not been reported. The MTD of HPβCD by IV injection in rats has been reported to be approximately 2.25 g/kg (Gould and Scott, *Food Chem. Toxicol.* 2005, 43, 1451). If the MTD in mice is much lower than that, it is possible that the vehicle is causing the dose-limiting toxicity.

Because of the difficulty of repeated tail vein injections in mice, our group is using IP administration of compound. The MTD of HPβCD appears to be greater than can be delivered even by a 1 mL injection of a saturated aqueous solution of HPβCD. Thus, when injected IP, the dose of HPβCD will likely be irrelevant. We have found the MTD of DNQ to be about 5 mg/kg by IP injection. At this dose mice become lethargic and unresponsive to touch. The effects subside after 1-2 hours and the mice return to a healthy state. Daily injections of this dose were not tolerated, but dosing every other day was tolerated.

Although the mouse model experiment provided encouraging results, two liabilities for future use of DNQ were noted: 1) DNQ is not well tolerated by mice at the doses required to see an anticancer effect, and 2) the low aqueous solubility of DNQ necessitates the use of HPβCD, the use of which is undesirable from both cost and potential toxicity standpoints.

Example 4

Synthesis and Evaluation of Derivatives of DNQ

Limitations of DNQ for In Vivo Administration.

Although DNQ displayed promising antitumor efficacy in the preliminary murine cancer model, we foresaw two potential hurdles for the future administration of DNQ in vivo: low aqueous solubility, and a narrow therapeutic window. We were confident that an analysis of the structure-activity relationship (SAR) of DNQ enabled by the synthesis of a library of derivatives, would reveal compounds that are both more soluble than and equipotent to DNQ. We planned to determine the MTD of all such derivatives in mice. Assuming that equivalent cytotoxicity in cell culture would translate into equivalent antitumor doses in mice, the compound with the highest MTD would provide the widest therapeutic window. Thus, we set out to discover a new lead compound by 1) synthesizing a library of DNQ derivatives, 2) establishing the SAR of DNQ 3) establishing the structure-solubility relationship of DNQ and 4) determining the MTD of the best new derivatives in healthy mice. By this process, a new lead compound would be identified and its efficacy in multiple mouse models of cancer would be explored.

Poor Aqueous Solubility.

Figure 4:
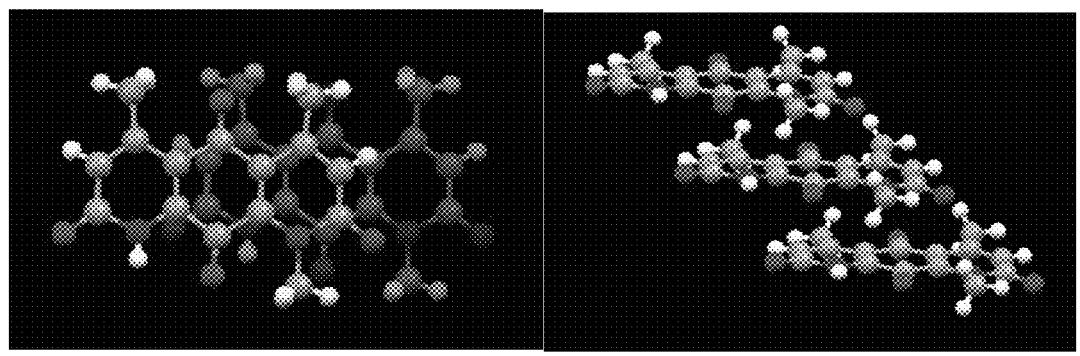
FIG. 4. X-ray crystal structure of DNQ showing π-stacking in the solid state.

Despite possessing multiple sites for hydrogen bonding interactions with water, DNQ is poorly soluble (100 μM in pH 7.4 PBS buffer). Two potential reasons for the insolubility of DNQ are its ability to π-stack in the solid state and double intermolecular hydrogen bonding. Both of these effects are clearly shown in a crystal structure of DNQ (FIG. 4) recently reported by Li and coworkers who isolated DNQ from a strain of *Pseudonocardia* isolated from the South China Sea (Li et al., *Mar. Drugs* 2011, 9, 1428). Because SCH 538415 is less potent than DNQ breaking up the intermolecular hydrogen bonding by substitution at the N—H might produce inactive derivatives. Therefore focus was placed on disruption of the π-stacking with the thought that breaking up this π-stacking by the addition of freely-rotating short alkyl chains would improve aqueous solubility despite increasing the lipophilicity.

Figure 5:
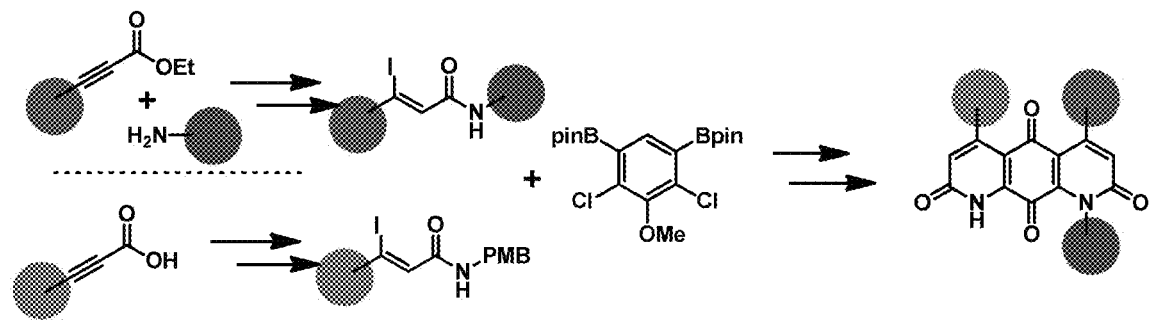
FIG. 5. Derivatization sites on DNQ according to various embodiments of the invention.

The synthetic route to DNQ was expected to be amenable to substitution at the three positions indicated by colored spheres in FIG. 5. Although it was expected that the aqueous solubility of DNQ derivatives bearing short alkyl chains would be greater than that of DNQ the lipophilicity of sufficiently long appendages would overcome the advantage of disrupting the π-stacking and result in less soluble derivatives. The optimal alkyl length for maximal aqueous solubility would be determined by synthesizing a series of n-alkyl derivatives and assessing their properties. The addition of polar functional groups (e.g., —OH, —NH$_2$, —COOH, etc.) to DNQ would be expected to have a strong positive effect on aqueous solubility.

Improving Solubility in HPβCD Solutions.

Like DNQ β-lap suffers from poor aqueous solubility (~160 μM in pH 7.4 PBS). It was found that dissolution of β-lap in a solution of HPβCD resulted in ~150-fold increase in solubility (20% HPβCD in H2O). When DNQ was dissolved in HPβCD solution, solubility increased only 30-fold. The difference in fold solubility increase between DNQ and β-lap is ascribed to the following: whereas β-lap is insoluble because of its high lipophilicity (which is offset by complexation with HPβCD) DNQ is insoluble because of stable solid packing—on which HPβCD has no effect. The same DNQ derivatives described in the previous section would likely benefit more by dissolution with HPβCD than DNQ itself—by virtue of their increased lipophilicity. Furthermore, certain appendages might display very high affinity for HPβCD which would result in significant solubility gains. Thus, the solubility of all derivatives, whether more or less soluble in water than DNQ would be tested in the presence of HPβCD.

Improving Solubility in Organic Solvents.

Another way that β-lap has been administered in vivo is encapsulated in micelles (Blanco et al., *Cancer Res.* 2010, 70, 3896). Whereas liposomal formulations are useful for water-soluble drugs—trapping them in the aqueous interior of the liposome—micelles trap lipophilic drugs in their hydrophobic interior. Thus, proposed lipophilic derivative of DNQ might be good candidates for micellar formulations. It was expected that the solubility of DNQ derivatives in organic solvents—such as DCM and THF—would be orders of magnitude greater than the solubility of DNQ itself because of the combined effects of destabilizing π-stacking and increasing lipophilicity.

Predicted SAR.

Figure 6:
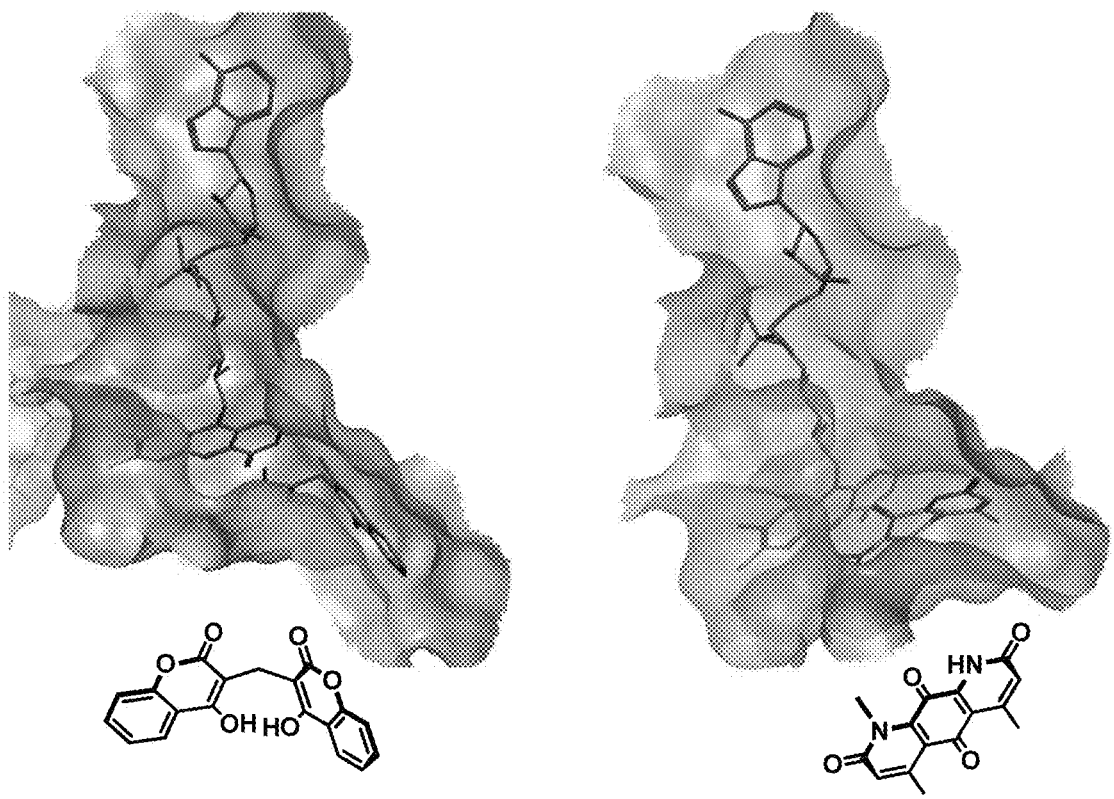
FIG. 6. X-ray crystal structure of human NQO1 with inhibitor dicoumarol (left) or with DNQ modeled in using MOE software (right). The FAD cofactor is represented in stick form with the adenine moiety at the top of the image and the tricyclin flavin in the active site. Drawings of the substrates are included to aid in visualizing the orientation of the molecules in the NQO1 active site.
Figure 7:
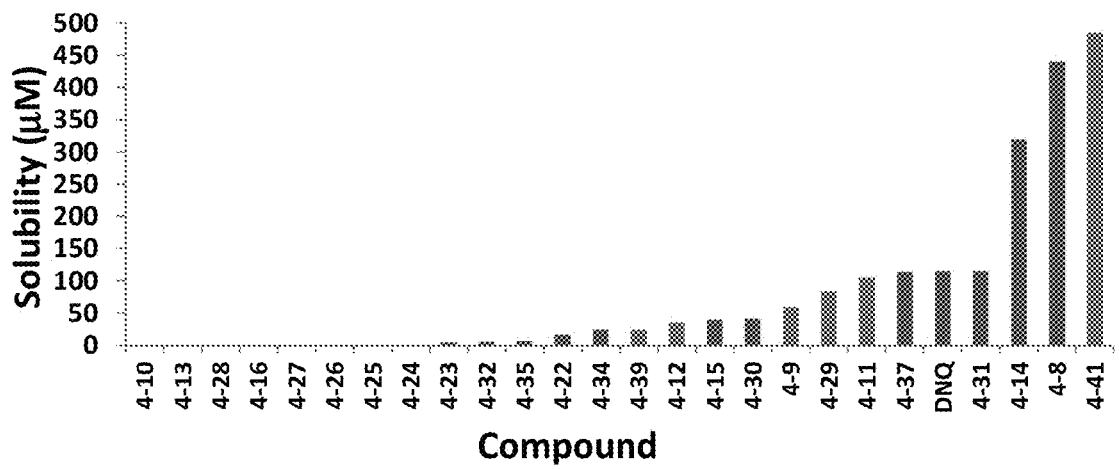
FIG. 7. Solubility of DNQ derivatives in pH 7.4 PBS. Compounds 4-23, 4-32, 4-35, 4-22, 4-34, 4-15, 4-30, 4-37, DNQ 4-31, 4-14, and 4-8 are "active" compounds (IC$_{50}$<500 nM), while compounds 4-39, 4-12, 4-9, 4-29, 4-11, and 4-41 are generally "inactive" compounds (IC$_{50}$>500 nM). The order of compounds in FIG. 7 is retained for FIGS. 8-11.
Figure 8:
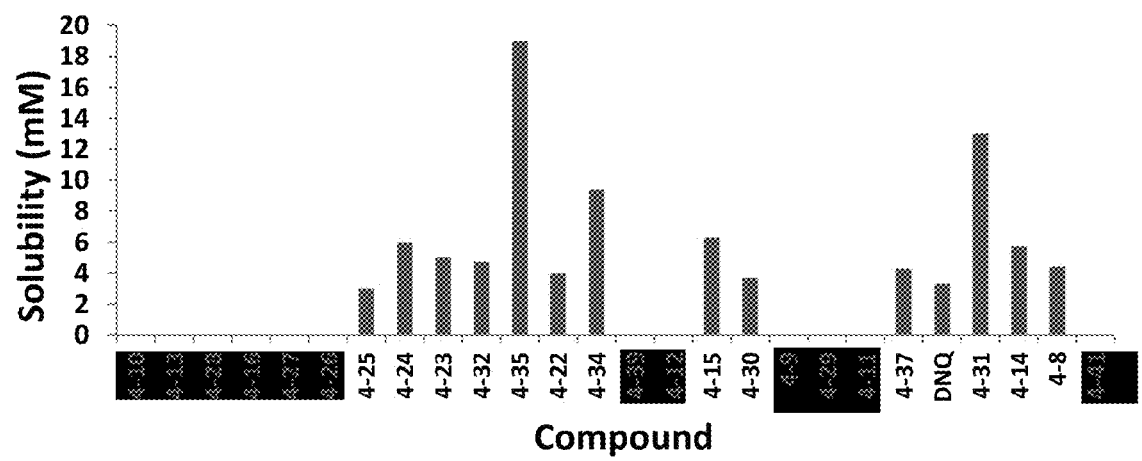
FIG. 8. Solubility of active DNQ derivatives in 20% HPβCD. Less active derivatives (4-10, 4-13, 4-28, 4-16, 4-27, 4-26, 4-39, 4-12, 4-9, 4-29, 4-11, and 4-41) were not assessed.

A large number of compounds with diverse structures have been identified as substrates of NQO1 (Colucci et al., *Org. Biomol. Chem.* 2008, 6, 637). This promiscuity suggests that derivatization of DNQ could yield compounds that are also substrates for the enzyme. Molecular modeling based on crystal structures of NQO1 support this notion. FIG. 6 (left) shows NQO1 with the inhibitor dicoumarol bound in the active site (Asher et al., *Biochemistry* 2006, 45, 6372). As drawn, the western coumarin of DIC π-stacks with the FAD cofactor, while the eastern half extends down a cavity that opens into the active site. Side chains of DNQ should be able to access this cavity as well. Northeast of the active site is another cavity through which the FAD passes that could potentially allow for substrate access as well. The western half of the active site is closed off—any side chains forced to lie in that area would reduce the binding affinity of the compound. Molecular modeling of DNQ in the NQO1 active site suggests that DNQ will π-stack with the FAD isoalloxazine moiety (FIG. 6, right), but that the orientation of DNQ in the binding pocket may not be important. The affinity of side chains of DNQ derivatives for the active site may make for stronger substrate-enzyme binding. Compounds that bind too weakly to NQO1 would be poor substrates, but compounds that bind too tightly would be inhibitors. Thus compounds with optimal binding properties should be the most potent cytotoxins in cell culture.

A preliminary set of nine derivatives was to be synthesized to probe the effect of substituents on DNQ at the three positions noted (Scheme 4.1). These compounds would be assessed for their potency in cell culture and their dependence on NQO1 for cytotoxicity by co-treating with dicoumarol. Based on the NQO1-dependent cytotoxicity of this initial set of derivatives, a second, larger set would be synthesized to further explore the SAR. Compounds that are equipotent to DNQ would then be assessed for their solubility properties in water, in HPβCD, and in organic solvents.

Scheme 4.1 Nine DNQ derivatives.

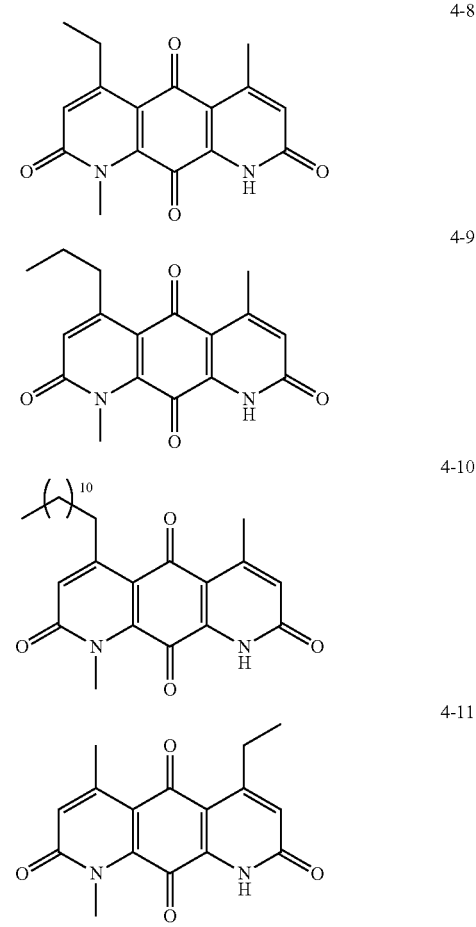

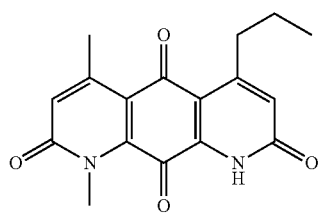

4-12

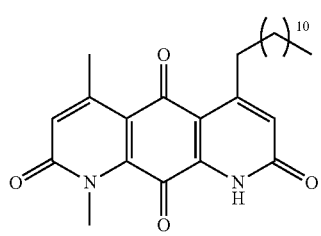

4-13

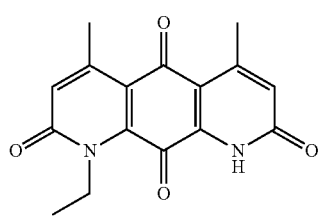

4-14

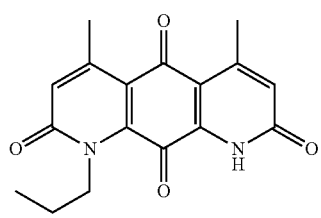

4-15

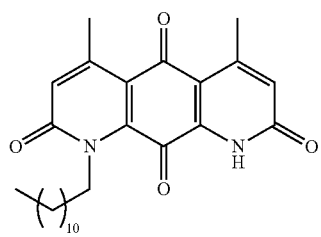

4-16

Synthesis and NQO1-Dependent Cytotoxicity of an Initial Set of 9 DNQ Derivatives.

We synthesized a set of nine derivatives bearing ethyl, propyl, or undecyl chains at each of three positions that are easily modified by the existing synthetic route to DNQ (Scheme 4.1). The required alkyne esters (of the type 4-1 for derivatives 4-8 and 4-9), alkyne acids (of the type 4-3 for derivatives 4-11 and 4-12), and primary amines (of the type 4-2 for derivatives 4-14 through 4-16) were commercially available and were used to make the indicated compounds through routes analogous to that for DNQ. The alkynes required to synthesize derivatives 4-10 and 4-13 were synthesized from alkyne 4-17 as shown in Scheme 4.2.

Scheme 4.2. Synthesis of alkynes 4-19 and 4-21 for preparation of 4-10 and 4-13.

The NQO1-dependent cytotoxicity of the first set of derivatives was determined in MCF-7 cells which express high levels of NQO1. Cells were exposed to DNQ for 2 hours in the presence or absence of 25 μM DIC. The media was then removed and cells were washed once with media then fresh media was added and the cells were incubated for 72 hours. Cell death was assessed using the sulforhodamine B assay previously described. $IC_{50}$ values for these compounds are listed in Table 4.1. While ethyl derivative 4-8 was equipotent with DNQ propyl derivative 4-9 was significantly less toxic. Dodecyl derivative 4-10 was insoluble in DMSO (<0.1 mM) and could not be assessed in this assay. We found that substitution opposite the NH (4-11 and 4-12) was poorly tolerated, with even a single methylene addition causing a significant loss of toxicity. As was the case with 4-10, compound 4-13 was insoluble in DMSO. Substitution off the nitrogen appeared well tolerated (4-14 and 4-15). Dodecyl derivative 4-16 was inactive and the protective effect of DIC could not be assessed because of its poor solubility.

As further evidence that the activity of these DNQ derivatives is dependent on their ability to be reduced by NQO1, full enzymatic measurements in vitro were performed. The results are shown in Table 4.1. We found a strong correlation between catalytic efficiency of substrates in vitro and their cell culture toxicity. The most active derivatives in cell culture displayed catalytic efficiencies above $3 \times 10^7$ $M^{-1}s^{-1}$. This provides strong evidence that the cytotoxicity of DNQ and its derivatives are dependent primarily upon the activity of NQO1 within the cell.

TABLE 4.1

Cytotoxicity and NQO1 dependence of nine initial DNQ derivatives.

| Compound | IC$_{50}$ vs. MCF-7 cells (μM ± s.e.) | | Fold protection by DIC | $k_{cat}/K_M$ (M$^{-1}$s$^{-1}$ × 10$^7$) |
|---|---|---|---|---|
|  |  | +25 μM DIC |  |  |
| DNQ  | 0.13 ± 0.02 | 1.7 ± 0.3 | 14 | 6.7 |
| 4-8  | 0.28 ± 0.06 | 1.3 ± 0.4 | 4.5 | 3.3 |
| 4-9  | 0.90 ± 0.25 | 2.6 ± 0.6 | 2.8 | 1.4 |
| 4-10 | —$^a$ | —$^a$ | —$^a$ | —$^a$ |
| 4-11 | 0.55 ± 0.06 | 4.9 ± 0.8 | 8.9 | 2.3 |
| 4-12 | 3.4 ± 0.6 | 5.3 ± 1.2 | 1.6 | 0.59 |
| 4-13 | —$^a$ | —$^a$ | —$^a$ | —$^a$ |
| 4-14 | 0.20 ± 0.01 | 3.4 ± 0.2 | 17 | 3.1 |
| 4-15 | 0.13 ± 0.01 | 1.3 ± 0.4 | 10 | 4.6 |
| 4-16 | 8.0 ± 1.6 | —$^a$ | —$^a$ | 0.89 |

$^a$Insufficiently soluble to determine.

Synthesis and NQO1-Dependent Cytotoxicity of a Second Set of DNQ Derivatives.

Having concluded that substitution off the nitrogen was likely to produce active derivatives, efforts were made to synthesize a second set of derivatives (Scheme 4.3) to determine the optimal length of an n-alkyl chain (4-22 through 4-25) as well as the effect of multiple substitutions (4-26 through 4-29), branched alkyl substituents (4-30 through 4-39), and polar functionalities (4-40 through 4-42). Deviations from the standard synthetic route are outlined below.

Scheme 4.3. New DNQ derivatives.

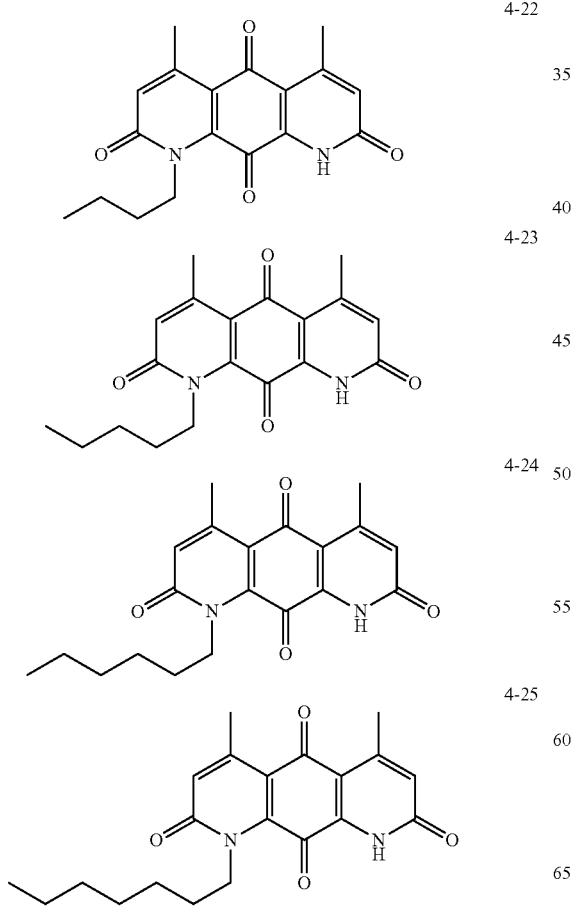

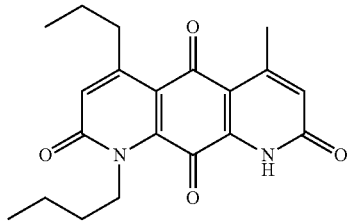

4-26

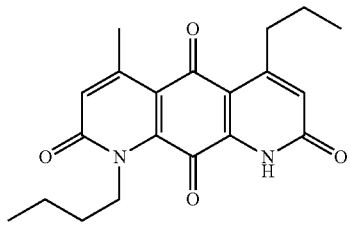

4-27

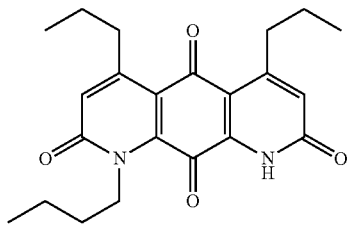

4-28

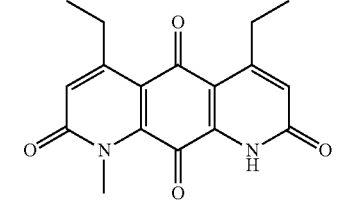

4-29

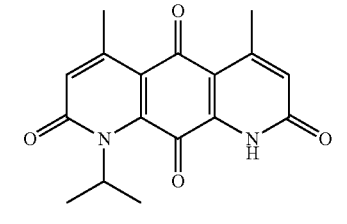

4-30

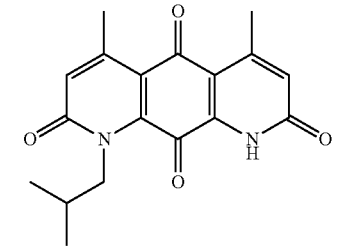

4-31

4-32

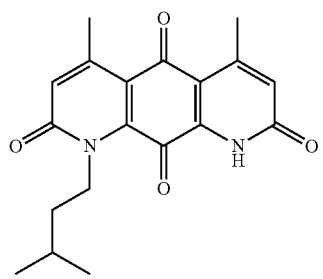

4-33

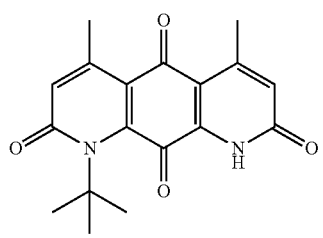

4-34

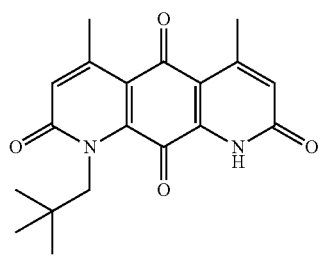

4-35

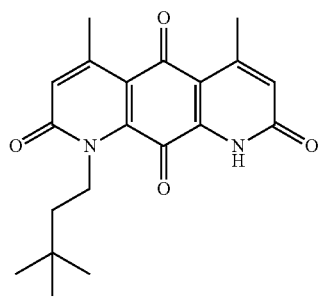

4-36

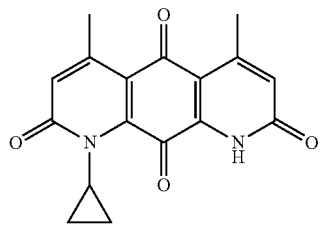

4-37

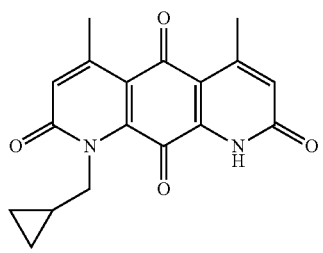

4-38

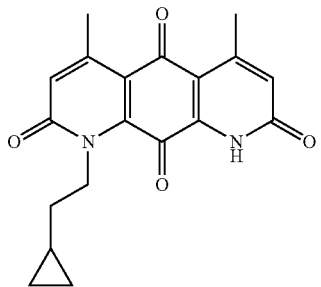

4-39

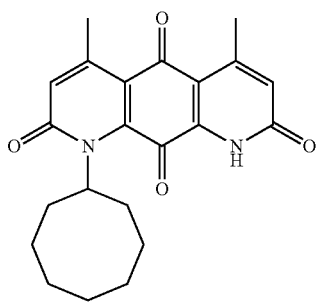

4-40

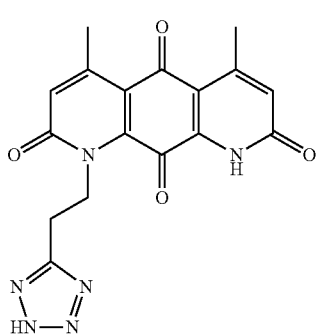

4-41

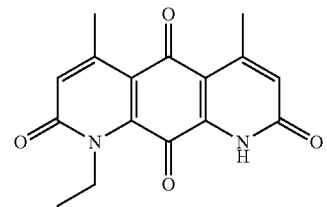

4-42

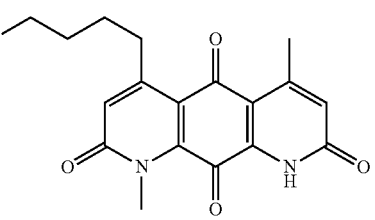

Synthesis of a Second Set of DNQ Derivatives.

Whereas most of the derivatives were synthesized by following the same protocol used to synthesize DNQ, a few derivatives required minor modifications of the route. The most sterically hindered amines were slow to react with ethyl-2-butynoate to generate the corresponding alkynyl amides, resulting in poor yields. It was found that the desired amides could be more efficiently synthesized using the route designed for the synthesis of the PMB-protected amide 2-71 (Scheme 4.4).

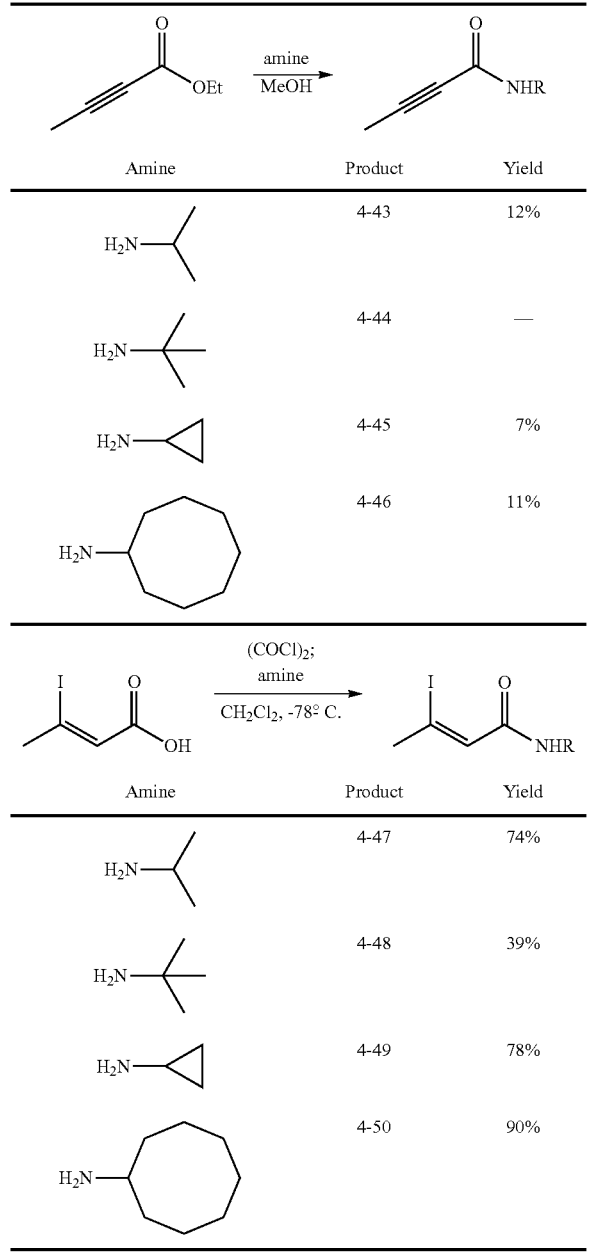

Scheme 4.4. Synthesis of amides bearing bulky substituents on nitrogen.

Other derivatives were found to be sensitive to the harsh acidic conditions used to deprotect the phenol in the penultimate step. Where this was the case, we used the following two-step Protocol (Scheme 4.5). Removal of the PMB protecting group was achieved in refluxing TFA and the product was isolated by chromatography. Treatment with $BBr_3$ in DCM at room temperature revealed the phenol which was used without purification. Oxidation under standard conditions with salcomine provided the desired DNQ derivative. Derivatives 4-36 and 4-38 were not recovered after precursors 4-59 and 4-61 were subjected to the oxidation; the reasons for this are unknown.

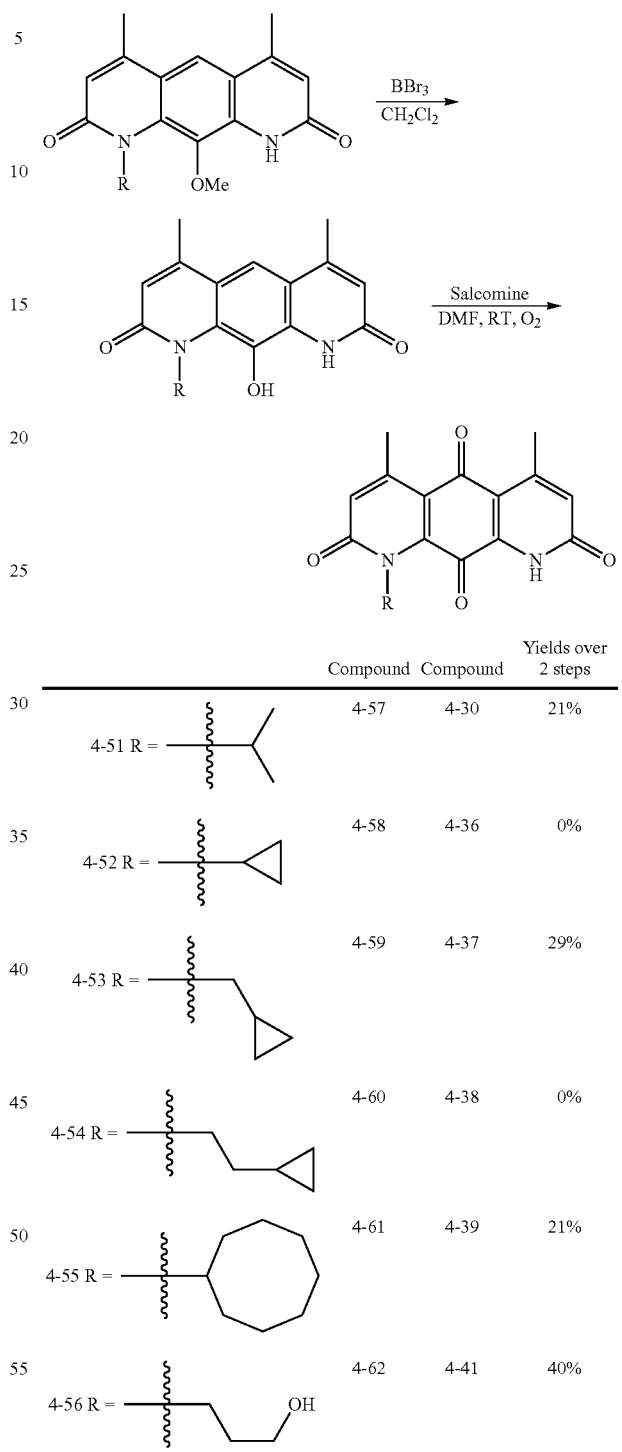

Scheme 4.5. Synthesis of DNQ derivatives bearing substituents sensitive to HBr-mediated deprotection.

In addition to 4-36 and 4-38, derivatives 4-33, 4-40, and 4-42 were not successfully synthesized. Unsurprisingly, the intramolecular amidation en route to t-butyl derivative 4-33 failed to provide the extremely congested tricyclic product even under elevated temperature and prolonged heating. Under conditions for the global deprotection of 4-63 or 4-64 en route to derivative 4-42 the pendant alcohol was converted to the alkyl bromide and attempts to convert the bromide back to the alcohol were unsuccessful (Scheme 4.6). The reason that the conversion to the bromide during deprotection occurred during synthesis of derivative 4-42 but not 4-41 is unknown.

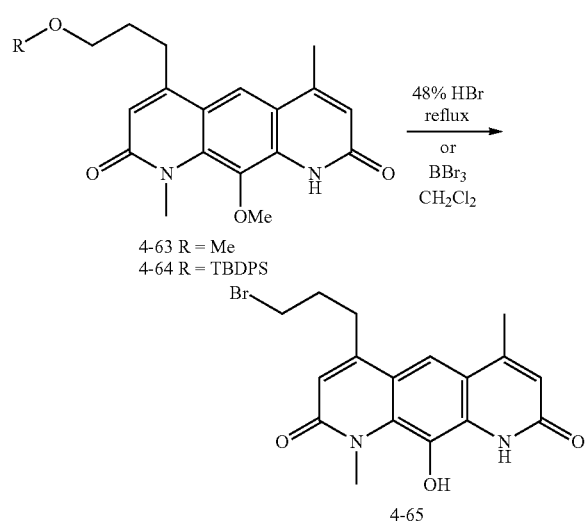

Scheme 4.6. Unexpected bromination of protected alcohols 4-63 and 4-64 during global deprotection.

NQO1-Dependent Cytotoxicity of a Second Set of DNQ Derivatives.

The DNQ derivatives synthesized were assayed for their toxicity to MCF-7 cells with or without DIC. The data from these experiments is organized in Table 4.2. Most of these compounds were found to be equipotent with DNQ and showed a strong dependence on uninhibited NQO1. Linear alkyl chains up to six carbons in length were tolerated (4-24), while the n-heptyl derivative 4-25 was somewhat less active. The only branched alkyl derivative that was significantly less toxic than DNQ was cyclooctyl compound 4-39. This tolerance of sterically-demanding substituents corresponds with a flexible and promiscuous NQO1 active site. The poor activity of hydroxyl derivative 4-41 may be a result of either poor binding with the largely hydrophobic NQO1 active site or with an excessively strong substrate-enzyme interaction because of hydrogen bonding. Alternatively, because the catalytic efficiency of 4-41 is equivalent to many of the more potent derivatives, 4-41 might be limited by other factors such as cell permeability.

TABLE 4.2

Cytotoxicity and NQO1 dependence of second set of DNQ derivatives.

| Compound | IC$_{50}$ vs. MCF-7 cells (µM ± s.e.) | | Fold protection by DIC | $k_{cat}/K_M$ (M$^{-1}$s$^{-1}$ × 10$^7$) |
|---|---|---|---|---|
| | | +25 µM DIC | | |
| DNQ | 0.13 ± 0.02 | 1.8 ± 0.3 | 14 | 6.7 |
| 4-22 | 0.27 ± 0.04 | 1.5 ± 0.4 | 5.5 | 7.9 |
| 4-23 | 0.20 ± 0.01 | 2.0 ± 0.9 | 10 | 5.0 |
| 4-24 | 0.29 ± 0.04 | 3.0 ± 0.6 | 10 | 5.8 |
| 4-25 | 0.42 ± 0.11 | 4.5 ± 0.4 | 11 | — |
| 4-26 | 0.77 ± 0.19 | 2.2 ± 0.6 | 2.8 | 3.6 |
| 4-27 | 6.3 ± 1.1 | 6.8 ± 1.6 | 1.1 | 0.63 |
| 4-28 | 36 ± 11 | 31 ± 10 | 0.9 | 0.22 |
| 4-29 | 3.8 ± 1.2 | 4.8 ± 1.1 | 1.3 | 0.46 |

TABLE 4.2-continued

Cytotoxicity and NQO1 dependence of second set of DNQ derivatives.

| Compound | IC$_{50}$ vs. MCF-7 cells (µM ± s.e.) | | Fold protection by DIC | $k_{cat}/K_M$ (M$^{-1}$s$^{-1}$ × 10$^7$) |
|---|---|---|---|---|
| | | +25 µM DIC | | |
| 4-30 | 0.24 ± 0.02 | 2.1 ± 0.8 | 8.6 | 2.0 |
| 4-31 | 0.23 ± 0.02 | 1.1 ± 0.1 | 4.8 | 6.1 |
| 4-32 | 0.18 ± 0.03 | 1.8 ± 0.5 | 10 | 7.3 |
| 4-34 | 0.23 ± 0.01 | 2.1 ± 0.7 | 8.9 | 4.9 |
| 4-35 | 0.22 ± 0.04 | 1.6 ± 0.6 | 7.1 | 6.7 |
| 4-37 | 0.22 ± 0.01 | 1.4 ± 0.2 | 6.1 | 2.8 |
| 4-39 | 0.83 ± 0.07 | 4.1 ± 0.8 | 3.8 | 1.7 |
| 4-41 | 0.68 ± 0.15 | 3.4 ± 0.6 | 5.0 | 3.9 |

Solubility of DNQ Derivatives.

To establish the relationship between structure and solubility of DNQ derivatives we assessed the solubility of every derivative in PBS buffer (pH 7.4), DCM, THF, DMSO, and a mixture of 33% methanol in DCM. The results are organized in Table 4.3 and shown graphically in the following sections. The descriptions of FIGS. 7-11 note "active" compounds (IC$_{50}$<500 nM) and generally "inactive" compounds (IC$_{50}$>500 nM).

TABLE 4.3

Solubility of DNQ derivatives in PBS, HPβCD, and several organic solvents.

| Compound | PBS (µM) | HPβCD (mM) | DMSO (mM) | CH$_2$Cl$_2$ (mM) | 2:1 CH$_2$Cl$_2$:MeOH (mM) |
|---|---|---|---|---|---|
| DNQ | 115 | 3.3 | 3.1 | 0.7 | 8.5 |
| 4.8 | 439 | 4.4 | 31 | 5.5 | 37 |
| 4.9 | 59 | — | 10 | 6.1 | 18 |
| 4.10 | <5 | — | <0.1 | 1.8 | 6.4 |
| 4.11 | 105 | — | 16 | 11 | 35 |
| 4.12 | 35 | — | 4.2 | 2.0 | 10 |
| 4.13 | <5 | — | <0.1 | 1.5 | 5.9 |
| 4.14 | 319 | 5.7 | 24 | 9.5 | 19 |
| 4.15 | 39 | 6.3 | 8.9 | 3.9 | 32 |
| 4.16 | <5 | — | 1.2 | 34 | 34 |
| 4-22 | 17 | 4.0 | 10 | 7.6 | 30 |
| 4-23 | <5 | 5.0 | 17 | 22 | 95 |
| 4-24 | <5 | 6.0 | 18 | 32 | 140 |
| 4-25 | <5 | 3.0 | 13 | 30 | — |
| 4-26 | <5 | — | 14 | 24 | 75 |
| 4-27 | <5 | — | 10 | 17 | 49 |
| 4-28 | <5 | — | 7.1 | 35 | 64 |
| 4-29 | 84 | — | 21 | 10 | 46 |
| 4-30 | 41 | 3.7 | 21 | 5.6 | 79 |
| 4-31 | 115 | 13 | 110 | 180 | 140 |
| 4-32 | 6 | 4.7 | 8.6 | 9.7 | 58 |
| 4-34 | 24 | 9.4 | 16 | 23 | 100 |
| 4-35 | 7 | 19 | 15 | 31 | 120 |
| 4-37 | 114 | 4.3 | 25 | 13 | 51 |
| 4-39 | 24 | — | 71 | 120 | 46 |
| 4-41 | 485 | — | 24 | 0.3 | 11 |

Aqueous Solubility.

The aqueous solubility of the compounds was determined by an LC-MS assay as described in the specification above. We applied the calibration curve generated for DNQ to the derivatives under the assumption that the UV profile of the derivatives of DNQ would be similar to that of DNQ.

After sonication and filtration most of the aqueous solutions were colorless. The solutions of DNQ, 4-31, and 4-37 were faintly yellow while 4-8, 4-14 and 4-41 were substantially more colored. The solution of 4-8, 4-14 and 4-41 were diluted 10-fold with PBS prior to LC-MS analysis to ensure that the concentrations fell within the range of the calibration curve. The results are given in Table 4.3 and FIG. 7.

As predicted, compounds 4-8 and 4-14 were more soluble than DNQ despite their increased lipophilicity. As the lipophilicity of derivatives increased further, however, solubility deceased. A few derivatives, such as 4-31 and 4-37, were substantially more soluble than derivatives of similar lipophilicity such as 4-22 and 4-23 indicating some advantage of moderate steric bulk near the nitrogen. It is unsurprising that compound 4-41 was the most soluble DNQ derivative. This highlights the necessity of making a series of alcohol-bearing derivatives in an attempt to find more active derivatives.

Solubility of DNQ Derivatives in HPβCD.

Although we were pleased to find active derivatives of DNQ that were up to 4-fold more soluble in water—sufficiently soluble for continuous IV infusion for human administration—this level of solubility was insufficient for animal studies by bolus injection. We therefore determined the solubility of all the most active derivatives ($IC_{50}$ below 500 nM) in 20% HPβCD solution. We used the same pH modulation protocol outlined for DNQ described in the specification above. The results are organized in Table 4.3 and FIG. 8. While all compounds were more soluble in HPβCD than in buffer alone, the fold increase in solubility varied widely.

We observed that, in general, the more lipophilic the compound the greater the enhancement of solubility by HPβCD. Of particular note is 4-35 which, although very poorly soluble in water, is the most soluble derivative in HPβCD, with a fold enhancement of ~3000. This fold enhancement in solubility is among the highest ever reported for HPβCD formulations (Stella and He, "Cyclodextrins" *Toxicol. Pathol.* 2008, 36, 30). In addition to being the most soluble derivative, 4-35 also appears to be the least sensitive to acidic pH. As the pH of the solution is lowered beyond the $pK_a$ of the N—H proton, the derivatives become substantially less soluble and precipitate rapidly. This is especially true for 4-8. However, once dissolved with HPβCD in basic solution, 4-35 remained in solution even when the pH was rendered acidic. This may result from a binding orientation between 4-35 and HPβCD which favors both a tight binding of the t-butyl in the cyclodextrin pocket as well as a strong hydrogen-bond between the deprotonated lactam and the hydroxyls at the rim of the cavity. This hydrogen bonding must be sufficiently strong to "hide" the deprotonated lactam from protons in the surrounding bulk water. This phenomenon of stability to acidic pH is displayed to varying lesser extents with the other derivatives. It is likely that compound 4-8 is oriented with the ethyl group in the cavity of the cyclodextrin which results in the deprotonated lactam being exposed to the bulk solvent. This would explain the strong dependence of the solubility of this compound on the pH of the solution.

Solubility in Organic Solvents.

Figure 9:
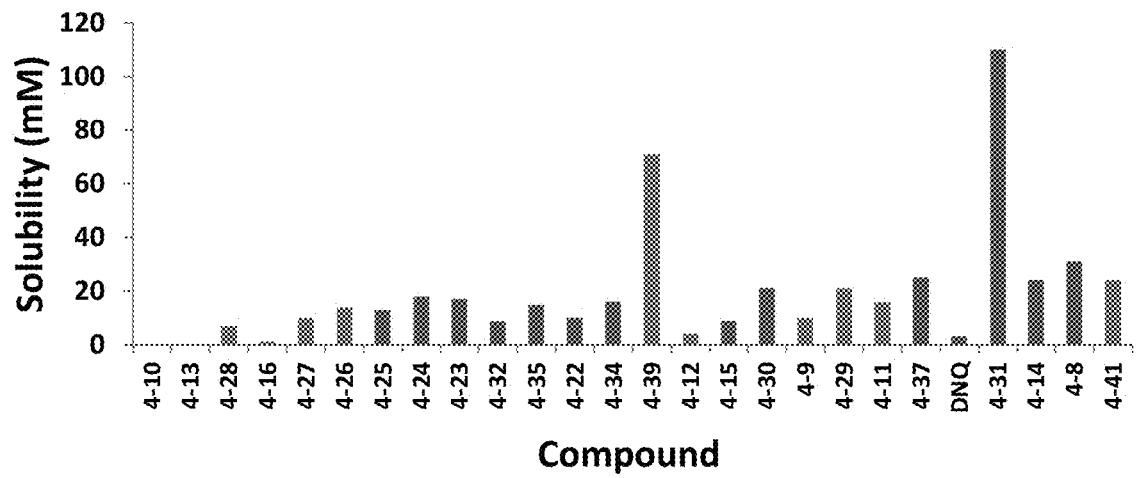
FIG. 9. Solubility of DNQ derivatives in DMSO. Compounds 4-25, 4-24, 4-23, 4-32, 4-35, 4-22, 4-34, 4-15, 4-30, 4-37, DNQ 4-31, 4-14, and 4-8 are "active" compounds (IC$_{50}$<500 nM), while compounds 4-28, 4-16, 4-27, 4-26, 4-39, 4-12, 4-9, 4-29, 4-11, and 4-41 are generally "inactive" compounds (IC$_{50}$>500 nM).
Figure 10:
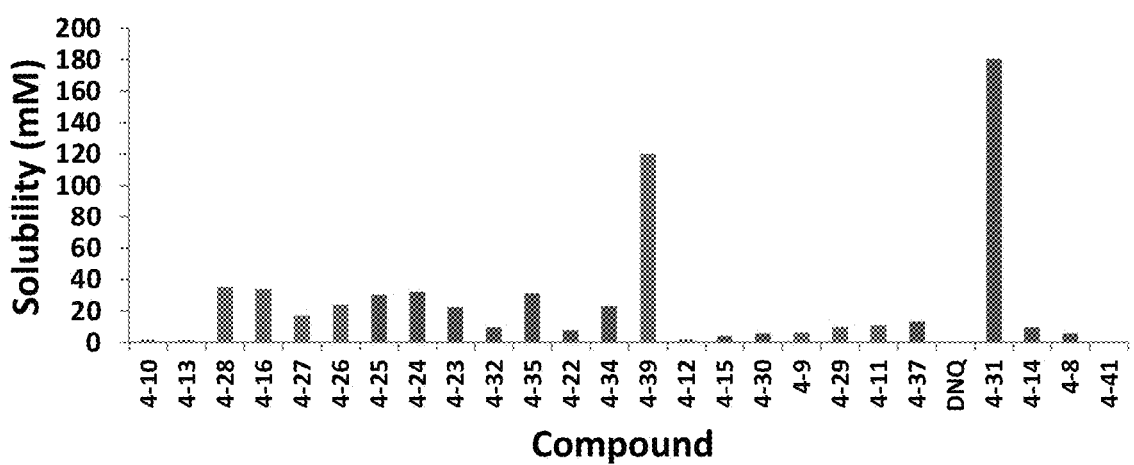
FIG. 10. Solubility of DNQ derivatives in dichloromethane. Compounds 4-25, 4-24, 4-23, 4-32, 4-35, 4-22, 4-34, 4-15, 4-30, 4-37, DNQ 4-31, 4-14, and 4-8 are "active" compounds (IC$_{50}$<500 nM), while compounds 4-10, 4-13, 4-28, 4-16, 4-27, 4-26, 4-39, 4-12, 4-9, 4-29, 4-11, and 4-41 are generally "inactive" compounds (IC$_{50}$>500 nM).
Figure 11:
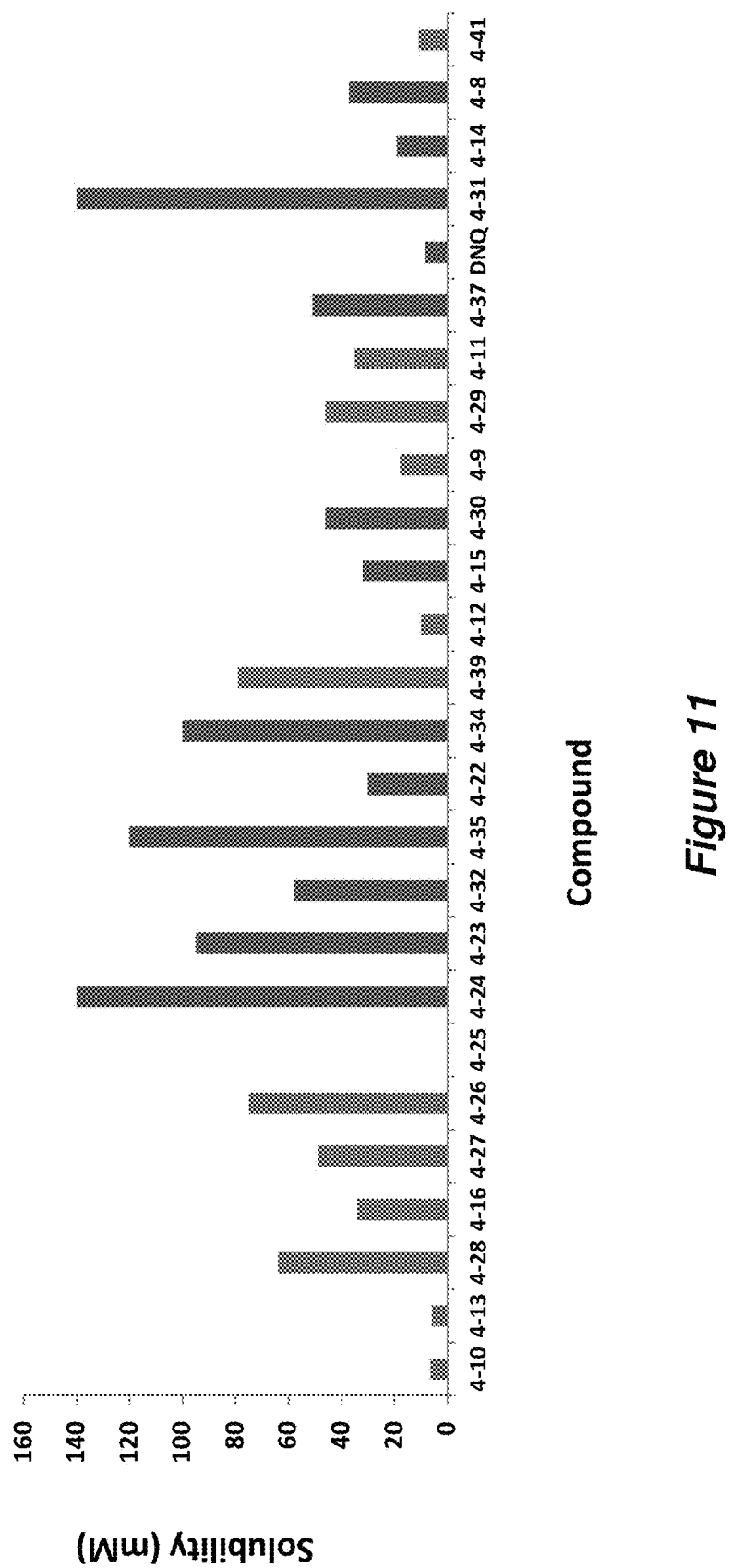
FIG. 11. Solubility of DNQ derivatives in 33% methanol in dichloromethane. Compounds 4-24, 4-23, 4-32, 4-35, 4-22, 4-34, 4-15, 4-30, 4-37, DNQ 4-31, 4-14, and 4-8 are "active" compounds (IC$_{50}$<500 nM), while compounds 4-10, 4-13, 4-28, 4-16, 4-27, 4-26, 4-39, 4-12, 4-9, 4-29, 4-11, and 4-41 are generally "inactive" compounds (IC$_{50}$>500 nM).

The solubility of DNQ derivatives in organic solvents was determined by measuring the amount of a given solvent required to dissolve a known amount of compound. Solvent was added to the compound in 50 µL aliquots and the slurry was sonicated. This process was repeated until all the solid had dissolved, leaving a clear red solution. The endpoint was generally very well defined. Solubility was assessed in DMSO, dichloromethane, and 33% methanol in dichloromethane (FIGS. 9, 10, and 11, respectively).

All but a few derivatives were more soluble in organic solvents than was DNQ. Only alcohol derivative 4-41 and the derivatives with dodecyl chains (4-10 and 4-13) were less soluble. Two compounds, active derivative 4-31 and a less active derivative 4-39, stood out as far more soluble than the others in both DMSO and dichloromethane. While we assume that the solubility of cyclooctyl compound 4-39 stems from its complete disruption of π-stacking as well as its high lipophilicity, we cannot explain the impressive solubility of 4-31. Other compounds, such as active n-hexyl derivative 4-24 displayed good solubility and appear to be reasonable candidates for micellar formulations.

Properties of 4-31 Measured by Absorption Systems.

A sample of compound 4-31 was delivered to Absorption Systems, a company that specializes in preclinical formulation and stability studies. They examined a large number of formulation and excipients but did not find conditions which better solubilized 4-31 than the HPβCD formulation described above. They measured a few physical properties of 4-31, including $pK_a$, log P and log D. Through potentiometric titrations they measured the $pK_a$ of 4-31 to be 8.0. The log P (octanol/0.15 M KCl partition coefficient of unionized compound) was found to be 1.8. The log D (octanol/0.15 M KCl partition coefficient of ionized compound) values at various pHs are shown in Table 4.4.

TABLE 4.4 logD of compound 4-31 between pH 3.0 and pH 9.0.

| pH | 3.0 | 4.0 | 6.8 | 7.0 | 8.0 | 9.0 |
|---|---|---|---|---|---|---|
| logD | 1.78 | 1.78 | 1.76 | 1.75 | 1.49 | 0.76 |

Absorption Systems measured the stability of 4-31 during incubation in rat, dog, and human plasma, whole blood, and liver microsomes. They report that 4-31 shows no sign of degradation after 2 hours in plasma or whole blood or after 1 hour in liver microsomes from any of the three species. This is in strong contrast to β-lap, which has been reported to be completely degraded within about 30 min in whole blood.

Maximum Tolerated Dose in Mice.

Thirteen of the 30 derivatives synthesized were found to be approximately equipotent to DNQ in cell culture and were at least as soluble as DNQ in HPβCD. All of these derivatives are currently being assessed for their maximum tolerated dose (MTD) in healthy mice. Compounds are formulated in HPβCD and delivered by IP injection to two mice once daily for five days. Initial results for DNQ and nine of the derivatives are shown in Table 4.5. MTD is displayed both in mg/kg and in µmol/kg to facilitate direct comparison with DNQ without the larger molecular weights of the derivatives obfuscating the results. All the derivatives cause the same phenotype in mice: at the MTD, mice are lethargic and unresponsive to touch for up to one hour, after which time they recover fully. Thus far, 4-35 is the best tolerated; it is tolerated at 3.5 folder higher concentration than DNQ.

TABLE 4.5

Maximum tolerated dose of DNQ and nine derivatives in mice.

|  | mg/kg | µmol/kg |
|---|---|---|
| DNQ | 5 | 18 |
| 4-8 | ≤10 | ≤35 |
| 4-14 | 10 | 35 |
| 4-15 | ≥14 | ≥44 |
| 4-23 | ≥15 | ≥44 |
| 4-24 | ≥16 | ≥44 |
| 4-31 | 14 | 44 |
| 4-32 | 15 | 44 |
| 4-34 | ≥15 | ≥44 |
| 4-35 | 22 | 62 |

In summary, we have reported our efforts to develop deoxynyboquinone derivatives as new candidates for the personalized treatment of cancer. We identified DNQ through a high-throughput screen for cytotoxicity and subsequently designed a flexible and modular synthetic route to DNQ and its derivatives. We demonstrated that DNQ kills cells through rapid ROS generation and that ROS generation occurred through a 2-electron bioreduction/oxidation process mediated exclusively by NQO1. We showed that DNQ was able to slow tumor growth in a mouse model of cancer but that the most efficacious doses were poorly tolerated by mice. We then synthesized a library of derivatives of DNQ and assessed them for cytotoxicity, solubility, and tolerance in mice. Through this process we identified a number of compounds that are more soluble than, equipotent to, and better tolerated by mice than DNQ. The most promising of these derivatives are being assessed in mouse models of cancer to identify a candidate molecule for further evaluation in preclinical and human clinical trials.

Preparation of DNQ Derivatives.

The materials and methods are analogous to those described for Example 1.

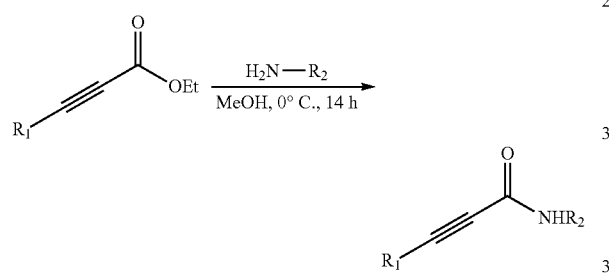

General Protocol A: Amidation of Ester.

To a solution of alkynyl ester (1 equiv.) in methanol (2 mM), chilled in an ice-water bath was added alkyl amine (1.2 equiv.). The reaction was stirred at 0° C. for 14 h. The solvent was evaporated directly from the flask and the residue was separated by silica gel chromatography to yield the desired alkynyl amide.

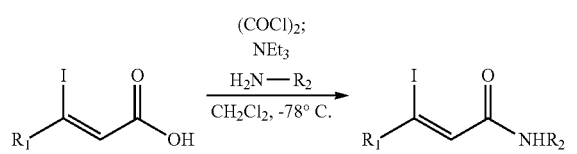

General Protocol B: Amidation of Acid Chloride.

To an oven-dried Schlenk flask with a stirbar was added iodoacid 2-73 and the flask was evacuated and backfilled with argon. Dry $CH_2Cl_2$ was added and the solution was chilled on an ice-water bath. Oxalyl chloride (3 equiv.) was added by syringe and the cold bath was removed. After 5 h at room temperature the volatile components were evaporated directly from the flask. Dry $CH_2Cl_2$ (10 mL) was added to the residual oil and the vial was chilled on a dry ice/isopropanol bath. Freshly distilled p-methoxybenzyl amine (1.1 equiv.) was added dropwise by syringe followed by $NEt_3$ (1.2 equiv.). The mixture was stirred for 10 minutes then was allowed to warm to RT. 1 M HCl (20 mL) was added and the solution was poured into a separatory funnel with $CH_2Cl_2$ (10 mL), shaken and separated. The aqueous fraction was extracted with $CH_2Cl_2$ (4×10 mL) then dried over $MgSO_4$ and evaporated. The residue was purified by silica gel chromatography.

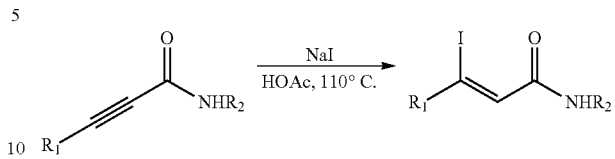

General Protocol C: Hydroiodination.

Alkynyl amide (1 equiv.), NaI (2 equiv.), and acetic acid (10 equiv.) were combined and heated to 115° C. for 8 h. Reaction completion was determined by removing aliquots for $^1$H-NMR analysis. The deep red reaction mixture was diluted with water and $CH_2Cl_2$, treated with $NaHSO_3$ until colorless, and carefully neutralized with a saturated aqueous solution of $NaHCO_3$. This mixture was poured into a separatory funnel with $CH_2Cl_2$, shaken and separated. The aqueous fraction was extracted with $CH_2Cl_2$. The combined organic fractions were washed with brine, dried over $MgSO_4$, and evaporated to yield the desired iodoamide.

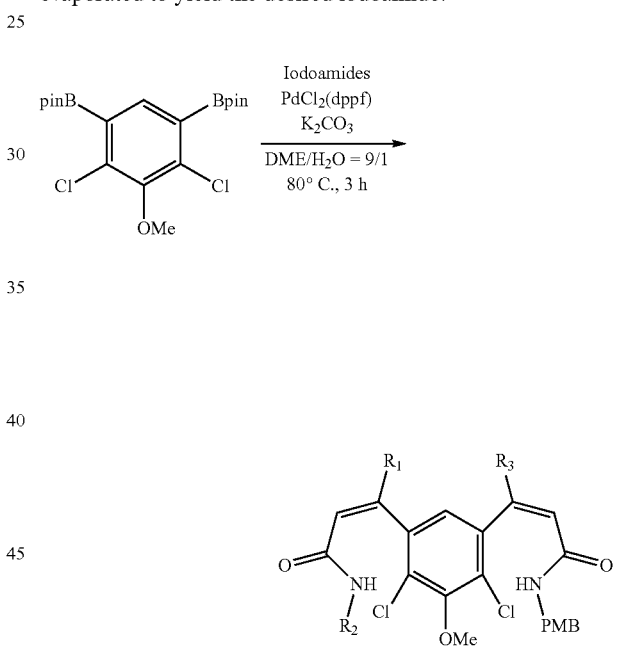

General Protocol D: Suzuki Cross-Coupling.

To a Schlenk flask with a stir bar was added pure (recrystallized) bispinacolboronate 4-6 (1 equiv.), $PdCl_2(dppf)$ (20 mol %), $K_2CO_3$ (6 equiv.), and both desired iodoamides (1.3 equiv. of amide bearing PMB, 1.5 equiv. of N-alkyl amide) and the flask was evacuated and backfilled with argon three times. Water (1 mL) and DME (9 mL) were added by syringe after degassing the solvents by bubbling with argon for 45 minutes. The flask was plunged into an oil bath at 80° C. for 3 h. The mixture was poured into a separatory funnel and diluted with water (5 mL). The mixture was extracted with EtOAc (2×20 mL). The combined organic extracts were dried over $MgSO_4$, filtered and evaporated to a deep red oil. The crude product was dissolved in $CH_2Cl_2$ and separated by silica gel chromatography. The purity of the diamide product was highly variable and the product was subjected to intramolecular amidation without further purification.

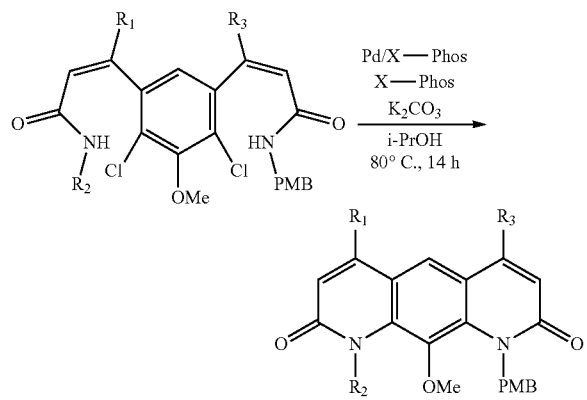

General Protocol E: Intramolecular Aryl Amidation.

In a Schlenk flask or a vial with a Teflon-lined cap were combined the diamide starting material, $K_2CO_3$ (6 equiv.), Pd/X-Phos (10 mol %), and X-Phos (10 mol %). The flask was cycled between vacuum and argon three times and argon-sparged i-PrOH was added by syringe. The mixture was heated to 80° C. with stirring for 14 h. Insoluble materials were removed by filtration through Celite and rinsed with $CH_2Cl_2$. The filtrate was evaporated and the residue was used directly in the next step.

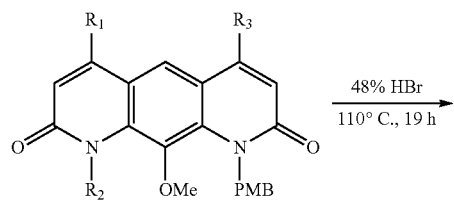

General Protocol F: HBr Deprotection.

The crude diazaanthracene was dissolved in 48% HBr and heated to 110° C. After 19 hours the reaction was removed from heat. The mixture was cooled on an ice bath and was carefully rendered basic by adding 10 M NaOH. The residual solid was removed by filtration through hardened filter paper and discarded. The filtrate was rendered acidic with 1 M HCl, whereupon a colloidal precipitate formed. The mixture was then centrifuged (3220×g for 5 minutes). The resulting semi-compact gelatinous solid was collected by filtration through hardened filter paper and dried to a constant mass under vacuum to yield the desired diazaanthracenol in frequently high purity as assessed by NMR.

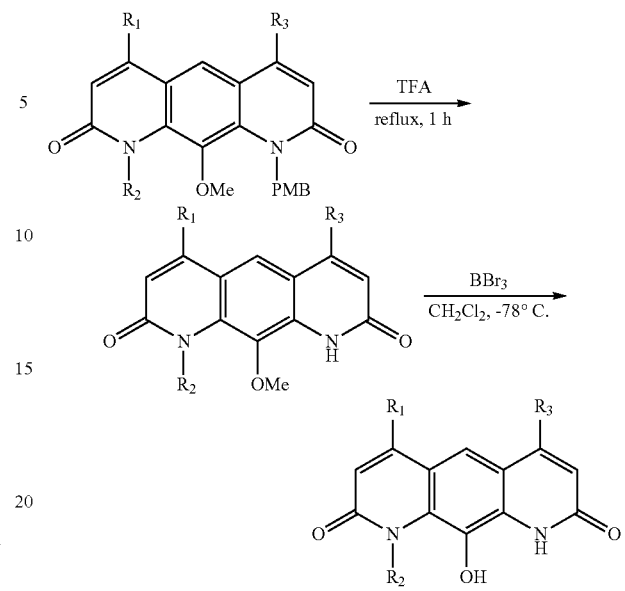

General Protocol G: $BBr_3$ Deprotection and Oxidation without Isolation.

For substrates that proved sensitive to global deprotection by HBr, the following protocol was employed. The product of intramolecular amidation (General Protocol E) was dissolved in TFA and heated to reflux for 1 h. The solvent was then evaporated and the residue was purified by silica gel chromatography.

In a Schlenk flask containing the PMB-deprotected material under Ar was added DCM and the solution was cooled in a dry ice/isopropanol bath. $BBr_3$ (6 equiv.) was added by syringe and the solution was stirred until starting material was consumed as shown by TLC. Residual $BBr_3$ was quenched by the addition of conc. $NaHCO_3$ solution until pH neutral. The solvents were evaporated. The residue was oxidized and the resulting DNQ derivative was purified using General Protocol H.

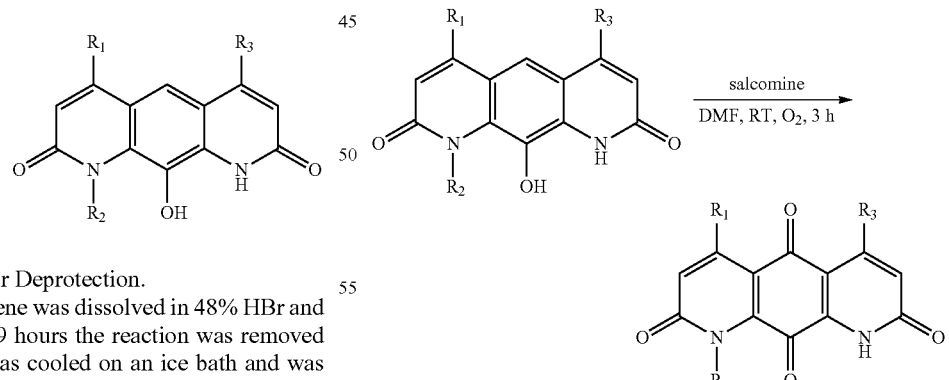

General Protocol H: Oxidation.

To a flask containing the diazaanthracenol starting material was added salcomine (10 mol %) and DMF. A balloon containing $O_2$ was fitted over the mouth of the flask and the slurry was stirred at room temperature. The solid dissolved after about 30 minutes. After 3 h stirring, the mixture was diluted with one volume each of DCM and hexanes and loaded directly onto a chromatography column consisting of a layer of basic alumina (5 cm) under a layer of silica gel (5 cm) prepared in DCM. The column was flushed with increasing amounts of methanol (0-2%) in DCM until the red product band entered the alumina layer which retained the product, allowing coeluting impurities to be removed. The product was then released from the basic alumina by adding 1% HOAc to the mobile phase. The red fractions were evaporated and purified by chromatography through silica gel (0-5% MeOH in DCM) to yield the desired DNQ derivative as an orange, red, or red-pink solid.

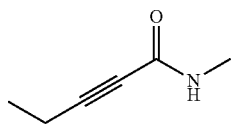

Synthesized by General Protocol A. 78% yield.

$^1$H-NMR (CDCl$_3$, 500 MHz): δ 6.1 (bs, 1H), 2.99 (d, 3H, J=5.0 Hz, minor rotamer), 2.81 (d, 3H, J=5.0 Hz, major rotamer), 2.35 (t, 2H, J=7.0 Hz, minor rotamer), 2.22 (t, 2H, J=7.0 Hz, major rotamer), 1.19 (t, 3H, J=7.5 Hz, minor rotamer), 1.13 (t, 3H, J=7.5 Hz, major rotamer). $^{13}$C-NMR (CDCl$_3$, 125 MHz): δ 154.50, 88.44, 74.95, 26.58, 12.93, 12.40.

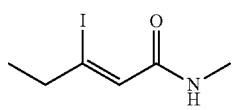

Synthesized by General Protocol C. 92% yield.

$^1$H-NMR (CDCl$_3$, 500 MHz): δ 6.28 (q, 1H. J=1.5 Hz, vinyl CH), 5.9 (bs, 1H, NH), 2.88 (d, 3H, J=5.0 Hz, NCH$_3$), 2.62 (dq, 2H, J=1.5 Hz, 7.5 Hz, allylic CH$_2$), 1.11 (t, 3H, J=7.5 Hz, —CH$_3$). $^{13}$C-NMR (CDCl$_3$, 125 MHz): δ 166.14, 127.91, 115.56, 40.94, 26.39, 14.67. HRMS (ESI-TOF) calcd for C$_6$H$_{11}$NOI (M+H)$^+$: 239.9885. found: 239.9885.

4-8

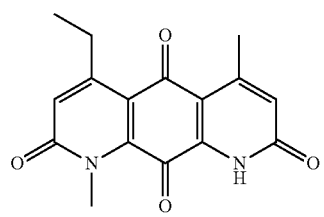

Synthesized by General Protocols D, E, F, and H. 7.4% yield over 4 steps.

$^1$H-NMR (2:1 CDCl$_3$:CD$_3$OD, 500 MHz): δ 6.81 (d, 1H, J=1.0 Hz, vinyl CH), 6.67 (d, 1H, J=1.0 Hz, vinyl CH), 3.92 (s, 3H), 3.09 (dq, 2H, J=7.0, 0.5 Hz, allylic CH$_2$), 2.64 (d, 3H, J=1.5 Hz, allylic CH$_3$), 1.26 (t, 3H, J=7.5 Hz, CH$_3$). $^{13}$C-NMR (CDCl$_3$, 125 MHz): δ 181.33, 175.31, 162.29, 161.90, 155.57, 151.68, 140.24, 138.50, 127.15, 125.27, 118.83, 115.06, 33.98, 27.88, 21.83, 13.55. HRMS (ESI-TOF) calcd for C$_{16}$H$_{15}$N$_2$O$_4$ (M+H)$^+$: 299.1032. found: 299.1034.

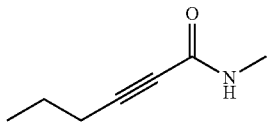

Synthesized by General Protocol A. 92% yield.

$^1$H-NMR (CDCl$_3$, 500 MHz): δ 6.04 (bs, 1H, major rotamer NH), 5.89 (bs, 1H, minor rotamer), 2.99 (d, 3H, J=5.0 Hz, minor rotamer), 2.81 (d, 3H, J=5.0 Hz, major rotamer), 2.33 (t, 2H, J=7.0 Hz, minor rotamer), 2.22 (t, 2H, J=7.0 Hz, major rotamer), 1.59 (sext, 2H, J=7.0 Hz, minor rotamer), 1.54 (sext, 2H, J=7.0 Hz, major rotamer), 0.99 (t, 3H, J=7.5 Hz, minor rotamer), 0.96 (t, 3H, J=7.5 Hz, major rotamer). $^{13}$C-NMR (CDCl$_3$, 125 MHz): δ 54.47 (major), 87.18 (major), 75.76 (major), 29.87 (minor), 26.58 (major), 21.43 (major), 20.97 (minor), 20.65 (major), 13.60 (major). HRMS (ESI) calcd for C$_7$H$_{12}$NO (M+H)$^+$: 126.0919. found: 126.0920.

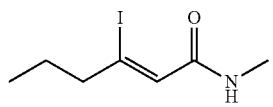

Synthesized by General Protocol C. 96% yield.

$^1$H-NMR (CDCl$_3$, 500 MHz): δ 6.40 (bs, 1H, NH), 6.30 (s, 1H, vinyl CH), 2.82 (d, 3H, J=5.0 Hz, NCH$_3$), 2.53 (t, 2H, J=7.0 Hz, allylic CH$_2$), 1.54 (sext, 2H, J=7.5 Hz), 0.86 (t, 3H, J=7.5 Hz). $^{13}$C-NMR (CDCl$_3$, 125 MHz): δ 165.86, 128.49, 114.01, 49.03, 26.30, 22.52, 12.82. HRMS (ESI-TOF) calcd for C$_7$H$_{13}$NOI (M+H)$^+$: 254.0042. found: 254.0045.

4-9

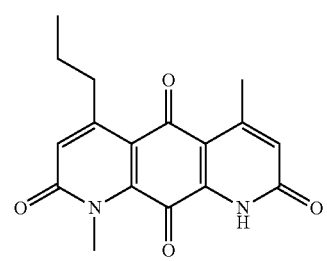

Synthesized by General Protocols D, E, F, and H. 3.4% yield over 4 steps.

$^1$H-NMR (CDCl$_3$, 500 MHz): δ 6.80 (s, 1H, vinyl CH), 6.68 (d, 1H, J=1.0 Hz, vinyl CH), 3.93 (s, 3H), 2.98 (t, 2H, J=7.5 Hz, allylic CH$_2$), 2.62 (d, 3H, J=1.0 Hz, allylic CH$_3$), 1.61 (q, 2H, J=7.5 Hz), 1.03 (t, 3H, J=7.5 Hz, CH(CH$_3$)$_2$). HRMS (ESI-TOF) calcd for C$_{17}$H$_{17}$N$_2$O$_4$(M+H)$^+$: 313.1188. found: 313.1189.

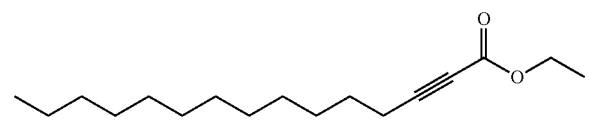 [SMILES: CCCCCCCCCCCCC#CC(=O)OCC]

To an oven-dried Schlenk flask was added 1-tetradecyne (0.748 g, 3.85 mmol) and THF (10 mL). Chilled to −78° C. Added n-BuLi (2.7 mL, 4.32 mmol) dropwise then stirred for 10 minutes. Added ethyl chloroformate (0.56 mL, 5.86 mmol) then allowed the reaction to warm to RT. The solvent was evaporated and the residue was purified by silica gel chromatography. Product was collected as a colorless oil (1.01 g, 3.79 mmol, 98.5% yield).

$^1$H-NMR (CDCl$_3$, 500 MHz): δ 4.19 (q, 2H, J=7.5 Hz), 2.30 (t, 2H, J=7.5 Hz), 1.56 (pent, 2H, J=7.5 Hz), 1.37 (bpent, 2H, J=8.0 Hz), 1.29 (t, 3H, J=7.5 Hz), 1.28-1.21 (m, 16H), 0.86 (t, 3H, J=7.0 Hz). $^{13}$C-NMR (CDCl$_3$, 125 MHz): δ 154.06, 89.66, 73.33, 61.91, 32.10, 29.82, 29.81, 29.77, 29.60, 29.53, 29.21, 29.04, 27.73, 22.87, 14.29, 14.21.

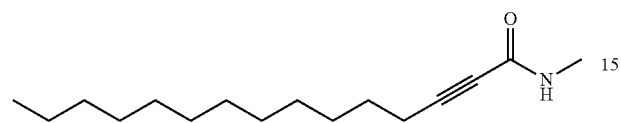

Synthesized by General Protocol A. 66% yield.

$^1$H-NMR (CDCl$_3$, 500 MHz): δ 6.42 (bs, 1H, major rotamer NH), 6.24 (bs, 1H, minor rotamer NH), 2.93 (d, 3H, J=5.0 Hz, minor rotamer NCH$_3$), 2.75 (d, 3H, J=5.0 Hz, major rotamer NCH$_3$), 2.29 (t, 2H, J=7.0 Hz, minor rotamer allylic CH$_2$), 2.18 (t, 2H, J=7.0 Hz, J=7.0 Hz, major rotamer allylic CH$_2$), 1.50 (pent, 2H, J=7.0 Hz, minor rotamer), 1.45 (pent, 2H, J=7.5 Hz, major rotamer), 1.29 (bpent, 2H, J=7.5 Hz, major rotamer), 1.25-1.13 (m, 16H), 0.79 (t, 3H, J=7.0 Hz). $^{13}$C-NMR (CDCl$_3$, 125 MHz): δ 157.35 (minor), 154.47 (major), 94.59 (minor), 87.17 (major), 75.50 (major), 73.14 (minor), 31.92 (major), 29.66 (major), 29.64 (2C, major), 29.48 (major), 29.36 (major), 29.10 (major), 28.90 (major), 27.83 (major), 26.43 (major), 22.69 (major), 18.57 (major), 14.11 (major).

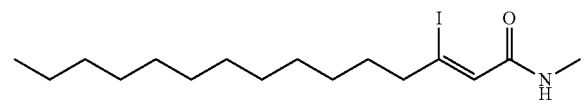 [SMILES: CCCCCCCCCCCC/C(I)=C/C(=O)NC]

Synthesized by General Protocol C. 100% yield.

$^1$H-NMR (CDCl$_3$, 500 MHz): δ 6.27 (s, 1H, vinyl CH), 5.74 (bs, 1H, NH), 2.89 (d, 3H, J=4.5 Hz), 2.59 (t, 2H, J=7.5 Hz), 1.56 (bt, 2H, J=7.0), 1.33-1.22 (m, 18H), 0.88 (t, 3H, J=7.0 Hz). $^{13}$C-NMR (CDCl$_3$, 125 MHz): δ 165.96, 128.50, 114.45, 47.23, 32.07, 29.81, 29.80, 29.77, 29.66, 29.51, 29.50, 29.36, 28.44, 26.36, 22.84, 14.29.

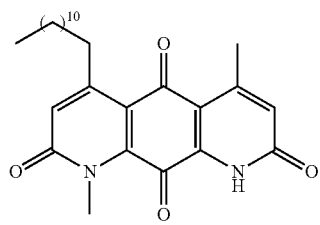

4-10

Synthesized by General Protocols D, E, F, and H. 7.0% yield over 4 steps.

$^1$H-NMR (2:1 CDCl$_3$:CD$_3$OD, 500 MHz): δ 6.78 (s, vinyl CH), 6.67 (s, 1H, J=1.0 Hz, vinyl CH), 3.91 (s, 3H), 3.03 (t, J=8.0 Hz), 2.64 (d, 3H, J=1.0 Hz, allylic CH$_3$), 1.58 (p, 2H, J=7.5 Hz), 1.44 (p, 2H, J=7.5 Hz), 1.27-1.4 (m, 16H), 0.89 (t, 3H, J=7.5 Hz). $^{13}$C-NMR (d-TFA, 125 MHz): δ 182.13, 176.16, 166.58 (bs), 163.92 (bs), 160.66, 141.89, 139.75, 128.19 (bs), 126.92, 125.93, 120.93, 38.25, 37.45, 33.96, 32.05, 31.63 (2C), 31.57, 31.52, 31.41, 31.36, 31.15, 24.53, 23.41, 14.85.

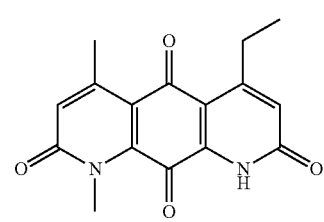

4-11

Synthesized by General Protocols D, E, F, and H. 6.2% yield over 4 steps.

$^1$H-NMR (2:1 CDCl$_3$:CD$_3$OD, 500 MHz): δ 6.78 (d, 1H, J=1.0 Hz, vinyl CH), 6.70 (s, 1H, vinyl CH), 3.92 (s, 3H), 3.09 (qd, 2H, J=7.5, 1.0 Hz), 2.64 (d, 3H, J=1.0 Hz, allylic CH$_3$), 1.26 (t, 3H, J=7.5 Hz, CH(CH$_3$)$_2$).

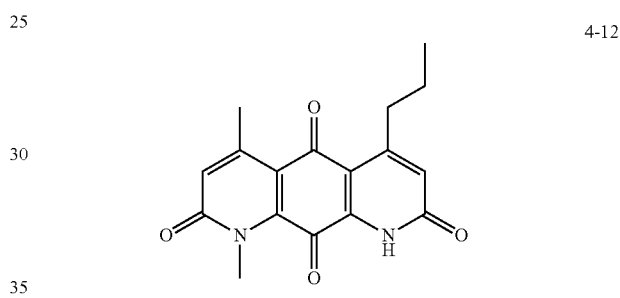

4-12

Synthesized by General Protocols D, E, F, and H. 11% yield over 4 steps.

$^1$H-NMR (CDCl$_3$, 500 MHz): δ 9.48 (bs, 1H, NH), 6.79 (d, 1H, J=1.5 Hz, vinyl CH), 6.69 (s, 1H, vinyl CH), 3.93 (s, 3H), 3.00 (t, 2H, J=7.5 Hz) 2.61 (d, 3H, J=1.0 Hz, allylic CH$_3$), 1.62 (sext, 2H, J=7.5 Hz), 1.04 (t, 3H, J=7.5 Hz). HRMS (ESI-TOF) calcd for C$_{17}$H$_{17}$N$_2$O$_4$ (M+H)$^+$: 313.1188. found: 313.1187.

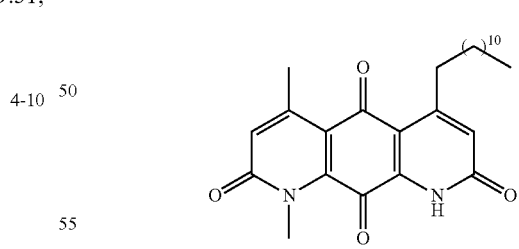

4-13

Synthesized by General Protocols D, E, F, and H. 20% yield over 4 steps.

$^1$H-NMR (2:1 CDCl$_3$:CD$_3$OD, 500 MHz): δ 6.78 (s, vinyl CH), 6.67 (s, 1H), 3.92 (s, 3H), 3.03 (t, J=7.5 Hz), 2.64 (d, 3H, J=1.0 Hz, allylic CH$_3$), 1.58 (p, 2H, J=7.5 Hz), 1.44 (p, 2H, J=7.5 Hz), 1.27-1.4 (m, 16H), 0.89 (t, 3H, J=7.5 Hz). $^{13}$C-NMR (d-TFA, 125 MHz): δ 182.21, 176.18, 166.64, 166.55, 165.56, 158.87, 141.347, 140.27, 128.14, 127.13, 126.09, 120.54, 37.93, 36.73, 33.95, 31.84, 31.61 (2H), 31.54, 31.42, 31.38, 31.34, 31.13, 24.50 24.37, 14.79.

4-29

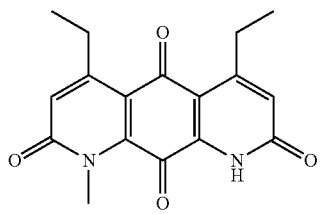

Synthesized by General Protocols D, E, F, and H. 17% yield over 4 steps.

$^1$H-NMR (CDCl$_3$, 500 MHz): δ 10.28 (bs, 1H), 6.83 (s, 1H, vinyl CH), 6.75 (s, 1H, vinyl CH), 3.93 (s, 3H), 3.07 (dq, 2H, J=7.5 Hz, 1.0 Hz), 3.04 (dq, 2H, J=7.5 Hz, 1.0 Hz), 1.25 (t, 3H, J=7.5 Hz), 1.24 (t, 3H, J=7.5 Hz). $^{13}$C-NMR (2:1 CDCl$_3$: CD$_3$OD, 125 MHz): δ 181.29, 175.34, 162.29, 162.15, 157.28, 155.52, 140.00, 138.78, 33.96, 27.90, 27.27, 13.62, 13.34.

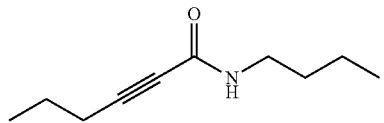

Synthesized by General Protocol A. 68% yield.

$^{13}$C-NMR (CDCl$_3$, 125 MHz): δ 153.76 (major), 89.96 (major), 75.94 (major), 43.21 (minor), 39.66 (major), 32.77 (minor), 31.51 (major), 21.43 (major), 20.96 (minor), 20.67 (major), 20.14 (major), 19.83 (minor), 13.8 (major), 13.8 (minor), 13.6 (major), 13.6 (minor). HRMS (ESI) calcd for C$_{10}$H$_{15}$NO (M+H)$^+$: 168.1388. found: 168.1382.

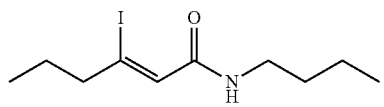

Synthesized by General Protocol C. 98% yield.

$^1$H-NMR (CDCl$_3$, 500 MHz): δ 6.26 (s, 1H, vinyl CH), 3.25 (q, 2H, J=7.0 Hz), 2.51 (t, 2H, J=7.5 Hz), 1.54 (sext, 2H, J=7.5 Hz), 1.48 (pent, 2H, J=7.5 Hz), 1.32 (sext, 2H, J=8.0 Hz), 0.86 (t, 3H, J=7.0 Hz), 0.85 (t, 3H, J=7.5 Hz). $^{13}$C-NMR (CDCl$_3$, 125 MHz): δ 165.13, 128.87, 113.51, 49.01, 39.36, 31.54, 22.51, 20.27, 13.81, 12.83. HRMS (ESI-TOF) calcd for C$_{10}$H$_{19}$NOI (M+H)$^+$: 296.0511. found: 296.0503.

4-26

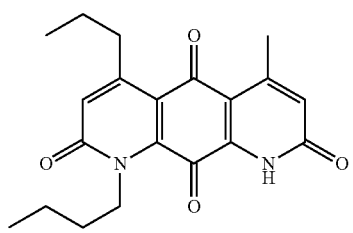

Synthesized by General Protocols D, E, F, and H. 6.3% yield over 4 steps.

$^1$H-NMR (CDCl$_3$, 500 MHz): δ 9.46 (s, 1H, NH), 6.77 (s, 1H, vinyl CH), 6.67 (d, 1H, J=1.0 Hz, vinyl CH), 4.50 (m, 2H), 2.97 (t, 2H, J=7.5 Hz, allylic CH$_2$), 2.61 (d, 3H, J=1.0 Hz, allylic CH$_3$), 1.69 (pent, 2H, J=8.0 Hz), 1.60 (sext, 2H, J=7.5 Hz), 1.47 (sext, 2H, J=8.0 Hz), 1.03 (t, 3H, J=7.5 Hz, CH$_3$), 0.99 (t, 3H, J=7.5 Hz, CH$_3$). $^{13}$C-NMR (CDCl$_3$, 125 MHz): δ 181.73, 175.37, 161.47, 160.91, 153.23, 151.31, 139.49, 137.78, 128.40, 127.82, 119.67, 114.98, 46.35, 39.15, 31.40, 23.14, 22.40, 20.40, 14.28, 13.93. HRMS (ESI-TOF) calcd for C$_{20}$H$_{23}$N$_2$O$_4$ (M+H)$^+$: 355.1658. found: 355.1655.

4-27

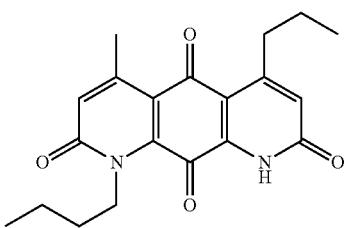

Synthesized by General Protocols D, E, F, and H. 6.7% yield over 4 steps.

$^1$H-NMR (CDCl$_3$, 500 MHz): δ 9.52 (s, 1H, NH), 6.77 (d, 1H, J=1.0 Hz, vinyl CH), 6.68 (s, 1H, vinyl CH), 4.52-4.49 (m, 2H), 2.99 (t, 2H, J=7.5 Hz, allylic CH$_2$), 2.59 (d, 3H, J=1.0 Hz, allylic CH$_3$), 1.68 (pent, 2H, J=7.5 Hz), 1.61 (sext, 2H, J=8.0 Hz, CH$_2$CH$_2$CH$_3$), 1.47 (sext, 2H, J=8.0 Hz, CH$_2$CH$_2$CH$_3$), 1.04 (t, 3H, J=7.5 Hz, CH$_3$), 1.00 (t, 3H, J=7.5 Hz, CH$_3$). $^{13}$C-NMR (CDCl$_3$, 125 MHz): δ 181.67, 175.28, 161.28, 160.96, 155.41, 149.27, 138.84, 138.25, 128.69, 127.59, 120.12, 114.40, 46.20, 36.30, 31.40, 23.53, 22.88, 20.39, 14.13, 13.92. HRMS (ESI-TOF) calcd for C$_{20}$H$_{23}$N$_2$O$_4$ (M+H)$^+$: 355.1658. found: 355.1658.

4-28

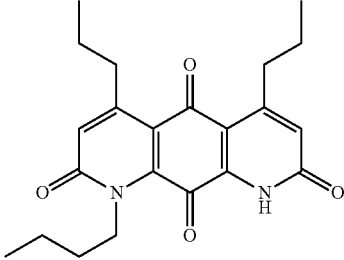

Synthesized by General Protocols D, E, F, and H. 13% yield over 4 steps.

$^1$H-NMR (CDCl$_3$, 500 MHz): δ 9.67 (s, 1H, NH), 6.77 (s, 1H, vinyl CH), 6.68 (s, 1H, vinyl CH), 4.49 (m, 2H), 2.98 (t, 2H, J=7.0 Hz, allylic CH$_2$), 2.95 (t, 2H, J=7.0 Hz, allylic CH$_2$), 1.69 (pent, 2H, J=8.5 Hz, CH), 1.72-1.65 (m, 2H), 1.65-1.55 (m, 4H), 1.47 (sext, 2H, J=7.5 Hz), 1.03 (t, 3H, J=7.0 Hz), 1.03 (t, 3H, J=7.5 Hz), 1.00 (t, 3H, J=7.5 Hz, CH$_3$). $^{13}$C-NMR (CDCl$_3$, 125 MHz): δ 181.70, 175.33, 161.47, 160.79, 155.34, 153.19, 139.15, 138.01, 127.93, 127.62, 120.10, 114.69, 46.31, 37.09, 36.23, 31.41, 23.25, 22.98, 20.40, 14.28, 14.14, 13.93. HRMS (ESI-TOF) calcd for C$_{22}$H$_{27}$N$_2$O$_4$ (M+H)$^+$: 383.1971. found: 383.1969.

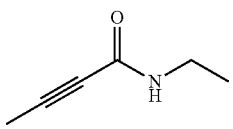

Synthesized by General Protocol A. 83% yield.
$^1$H-NMR (CDCl$_3$, 500 MHz): δ 6.25 (bs, 1H), 3.35 (pent, 2H, J=7.0 Hz, minor rotamer NCH$_2$), 3.23 (pent, 2H, J=7.5 Hz, major rotamer), 1.95 (s, 3H, minor rotamer), 1.85 (s, 3H, major rotamer), 1.12 (t, 3H, J=7.5 Hz, minor rotamer), 1.08 (t, 3H, J=7.0 Hz, major rotamer). $^{13}$C-NMR (CDCl$_3$, 125 MHz): δ 153.58 (major), 82.80 (major), 75.05 (major), 38.20 (minor), 34.66. (major), 15.91 (minor), 14.51 (major), 3.93 (minor), 3.59 (major). HRMS (ESI) calcd for C$_6$H$_{10}$NO (M+H)$^+$: 112.0762. found: 112.0764.

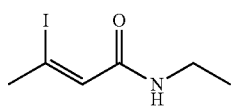

Synthesized by General Protocol C. 98% yield.
$^1$H-NMR (CDCl$_3$, 500 MHz): δ 6.28 (bs, 1H, NH), 6.22 (s, 1H, vinyl CH), 3.30 (pent, 2H, J=7.5 Hz, NCH$_2$), 2.59 (s, 3H, allylic CH$_3$), 1.12 (s, 3H). $^{13}$C-NMR (CDCl$_3$, 125 MHz): δ 164.85, 129.28, 105.58, 35.75, 34.45, 14.74. HRMS (ESI-TOF) calcd for C$_6$H$_{11}$NOI (M+H)$^+$: 139.9885. found: 139.9884.

4-14

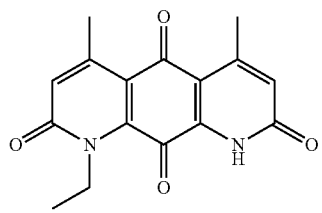

Synthesized by General Protocols D, E, F, and H. 13% yield over 4 steps.
$^1$H-NMR (2:1 CDCl$_3$:CD$_3$OD, 500 MHz): δ 6.76 (d, 1H, J=1.0 Hz, vinyl CH), 6.67 (d, 1H, J=1.0 Hz, vinyl CH), 4.51 (q, 2H, J=8.0 Hz), 2.36 (m, 6H, allylic CH$_3$), 1.45 (t, 3H, J=7.0 Hz).

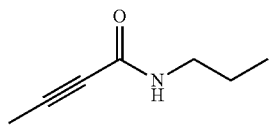

Synthesized by General Protocol A. 71% yield.
$^1$H-NMR (CDCl$_3$, 500 MHz): δ 5.99 (bs, 1H), 3.31 (q, 2H, J=7.0 Hz, minor rotamer NCH$_2$), 3.20 (q, 2H, J=7.5 Hz, major rotamer NCH$_2$), 1.98 (s, 3H, minor rotamer allylic CH$_3$), 1.89 (s, 3H, major rotamer allylic CH$_3$), 1.50 (sext, 2H, J=7.5 Hz), 0.89 (t, 3H, J=7.5 Hz). $^{13}$C-NMR (CDCl$_3$, 125 MHz): δ 153.71 (major), 89.96 (major), 75.13 (major), 45.15 (minor), 41.57 (major), 23.92 (minor), 22.69 (major), 11.39 (major), 11.18 (minor), 3.69 (major).

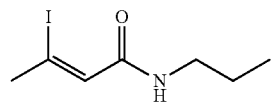

Synthesized by General Protocol C. 98% yield.
$^1$H-NMR (CDCl$_3$, 500 MHz): δ 6.23 (d, 1H. J=1.5 Hz, vinyl CH), 6.22 (bs, 1H, NH), 3.23 (d, 2H, J=7.0 Hz, NCH$_2$), 2.60 (d, 3H, J=1.5 Hz, allylic CH$_3$), 1.53 (sext, 2H, J=7.0 Hz), 0.90 (t, 3H, 7.5 Hz). $^{13}$C-NMR (CDCl$_3$, 125 MHz): δ 164.98, 129.47, 105.47, 41.34, 35.76, 22.77, 11.61. HRMS (ESI-TOF) calcd for C$_7$H$_{13}$NOI (M+H)$^+$: 254.0042. found: 254.0044.

4-15

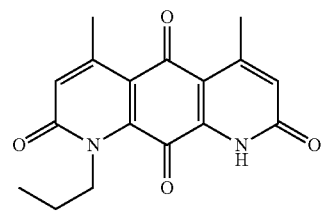

Synthesized by General Protocols D, E, F, and H. 13% yield over 4 steps.
$^1$H-NMR (CDCl$_3$, 500 MHz): δ 6.77 (d, 1H, J=1.0 Hz, vinyl CH), 6.68 (d, 1H, J=1.5 Hz, vinyl CH), 4.60 (m, 2H), 2.62 (d, 3H, J=1.5 Hz, allylic CH$_3$), 2.60 (d, 3H, J=1.0 Hz, allylic CH$_3$), 1.73 (sext, 2H, J=8.0 Hz, CH), 1.04 (t, 3H, J=7.5 Hz). $^{13}$C-NMR (CDCl$_3$, 125 MHz): δ 181.48, 175.09, 161.87, 161.75, 151.69, 149.97, 139.36, 138.58, 127.43, 127.21, 119.48, 114.79, 22.87, 22.20, 21.81, 10.72.

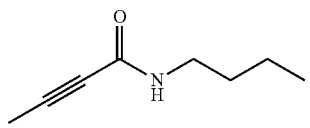

Synthesized by General Protocol A. 78% yield.
$^1$H-NMR (CDCl$_3$, 500 MHz): δ 6.01 (bs, 1H), 3.34 (q, 2H, J=7.0 Hz, minor rotamer NCH$_2$), 3.23 (q, 2H, J=6.0 Hz, major rotamer NCH$_2$), 1.98 (s, 3H, minor rotamer allylic CH$_3$), 1.89 (s, 3H, major rotamer allylic CH$_3$), 1.46 (pent, 2H, J=7.0 Hz), 1.31 (sext, 2H J=7.5 Hz), 0.88 (t, 3H, J=7.5 Hz). $^{13}$C-NMR (CDCl$_3$, 125 MHz): δ 153.71 (major), 89.96 (major), 75.13 (major), 45.15 (minor), 41.57 (major), 23.92 (minor), 22.69 (major), 11.39 (major), 11.18 (minor), 3.69 (major).

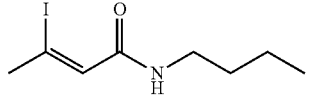

Synthesized by General Protocol C. 97% yield.
$^1$H-NMR (CDCl$_3$, 500 MHz): δ 6.23 (d, 1H. J=1.5 Hz, vinyl CH), 3.26 (q, 2H, J=7.0 Hz, NCH$_2$), 2.59 (d, 3H, J=1.5 Hz, allylic CH$_3$), 1.48 (p, 2H, J=7.5 Hz), 1.32 (sext, 2H, J=7.5 Hz), 0.87 (t, 3H, J=7.5 Hz). $^{13}$C-NMR (CDCl$_3$, 125 MHz): δ 164.93, 129.47, 105.41, 39.35, 35.75, 31.55, 20.26, 13.83. HRMS (ESI-TOF) calcd for C$_8$H$_{15}$NOI (M+H)$^+$: 268.0198. found: 268.0197.

4-22

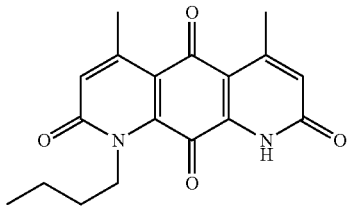

Synthesized by General Protocols D, E, F, and H. 9.9% yield over 4 steps.
$^1$H-NMR (CDCl$_3$, 500 MHz): δ 9.54 (bs, 1H), 6.77 (q, 1H, J=1.0 Hz, vinyl CH), 6.68 (q, 1H, J=1.0 Hz, vinyl CH), 4.53-4.50 (m, 2H), 2.62 (d, 3H, J=1.0 Hz, allylic CH$_3$), 2.60 (d, 3H, J=1.0 Hz, allylic CH$_3$), 1.68 (pent, 2H, J=7.5 Hz), 1.47 (sext, 2H, J=7.5 Hz), 1.00 (t, 3H, J=7.5 Hz). HRMS (ESI-TOF) calcd for C$_{17}$H$_{17}$N$_2$O$_4$(M+H)$^+$: 313.1188. found: 313.1190.

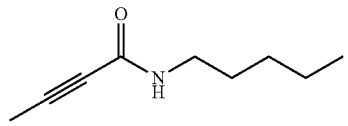

Synthesized by General Protocol A. 86% yield.
HRMS (ESI) calcd for C$_9$H$_{16}$NO (M+H)$^+$: 154.1232. found: 154.1231.

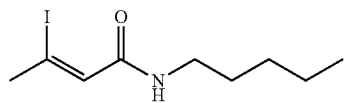

Synthesized by General Protocol C. 81% yield.
$^1$H-NMR (CDCl$_3$, 500 MHz): δ 6.22 (d, 1H. J=1.5 Hz, vinyl CH), 5.77 (bs, 1H, NH), 3.32 (q, 2H, J=7.0 Hz, NCH$_2$), 2.64 (d, 3H, J=1.5 Hz, allylic CH$_3$), 1.55 (pent, 2H, J=7.0 Hz), 1.35-1.30 (m, 4H), 0.89 (t, 3H, J=7.0 Hz). HRMS (ESI-TOF) calcd for C$_9$H$_{17}$NOI (M+H)$^+$: 282.0355. found: 282.0356.

4-23

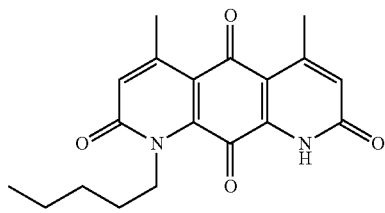

Synthesized by General Protocols D, E, F, and H. 11% yield over 4 steps.
$^1$H-NMR (2:1 CDCl$_3$:CD$_3$OD, 500 MHz): δ 6.76 (d, 1H, J=1.0 Hz, vinyl CH), 6.67 (d, 1H, J=1.5 Hz, vinyl CH), 4.48-4.43 (m, 2H), 2.63 (d, 3H, J=1.5 Hz, allylic CH$_3$), 2.63 (d, 3H, J=1.0 Hz, allylic CH$_3$), 1.77 (pent, 2H, J=7.5 Hz), 1.48-1.40 (m, 4H), 0.95 (t, 3H, J=7.0 Hz). $^{13}$C-NMR (2:1 CDCl$_3$:CD$_3$OD, 125 MHz): δ 181.47, 175.05, 161.83, 161.68, 151.66, 149.89, 139.31, 138.53, 127.40, 127.19, 119.45, 114.75, 46.52, 28.82, 28.48, 22.87, 22.07, 21.81, 13.58. HRMS (ESI-TOF) calcd for C$_{19}$H$_{21}$N$_2$O$_4$ (M+H)$^+$: 341.1501. found: 341.1496.

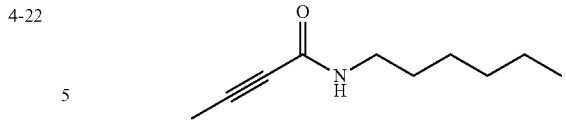

Synthesized by General Protocol A. 79% yield.
$^1$H-NMR (CDCl$_3$, 500 MHz): δ 5.85 (bs, 1H, major rotamer NH), 3.35 (q, 2H, J=7.0 Hz, minor rotamer), 3.23 (q, 2H, J=7.0 Hz, major rotamer), 2.00 (s, 3H, minor rotamer), 1.91 (s, 3H, major rotamer), 1.48 (pent, 2H, J=7.0 Hz), 1.33-1.23 (m, 6H), 0.86 (t, 3H, J=7.0 Hz). HRMS (ESI) calcd for C$_{10}$H$_{18}$NO (M+H)$^+$: 168.1388. found: 168.1391.

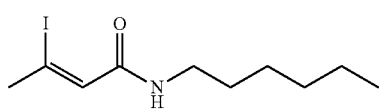

Synthesized by General Protocol C. 98% yield.
$^1$H-NMR (CDCl$_3$, 500 MHz): δ 6.22 (q, 1H. J=1.5 Hz, vinyl CH), 5.73 (bs, 1H, NH), 3.32 (q, 2H, J=7.0 Hz), 2.64 (d, 3H, J=1.5 Hz, allylic CH$_3$), 1.55 (pent, 2H, J=7.0 Hz), 1.38-1.27 (m, 6H), 0.88 (t, 3H, J=7.0 Hz). HRMS (ESI-TOF) calcd for C$_{10}$H$_{19}$NOI (M+H)$^+$: 296.0511. found: 296.0510.

4-24

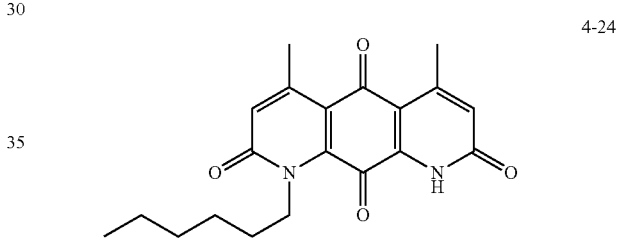

Synthesized by General Protocols D, E, F, and H. 12% yield over 4 steps.
$^1$H-NMR (2:1 CDCl$_3$:CD$_3$OD, 500 MHz): δ 6.76 (s, 1H), 6.67 (s, 1H), 4.45 (m, 2H), 2.63 (d, 3H, J=1.0 Hz, allylic CH$_3$), 2.63 (d, 3H, J=1.0 Hz, allylic CH$_3$), 1.76 (pent, 2H, J=7.5 Hz), 1.46 (pent, 2H, J=7.0 Hz), 1.40-1.34 (m, 4H), 0.92 (t, 3H, J=7.0 Hz). $^{13}$C-NMR (2:1 CDCl$_3$:CD$_3$OD, 125 MHz): δ 181.46, 175.04, 161.82, 161.66, 151.65, 149.88, 139.30, 138.53, 127.40, 127.20, 119.44, 114.74, 46.57, 31.18, 28.76, 26.36, 22.87, 22.35, 21.81, 13.58. HRMS (ESI-TOF) calcd for C$_{20}$H$_{23}$N$_2$O$_5$ (M+H)$^+$: 355.1658. found: 355.1660.

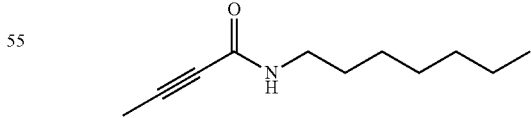

Synthesized by General Protocol A. 55% yield.
$^1$H-NMR (CDCl$_3$, 500 MHz): δ 5.95 (bs, 1H, NH), 3.34 (q, 2H, J=7.0 Hz, minor rotamer NCH$_2$), 3.22 (dt, 2H, J=7.0 Hz, major rotamer), 1.98 (s, 3H, minor rotamer), 1.89 (s, 3H, major rotamer), 1.47 (pent, 2H, J=7.5 Hz), 1.30-1.20 (m, 8H), 0.84 (t, 3H, J=7.0 Hz). $^{13}$C-NMR (CDCl$_3$, 125 MHz): δ 156.51 (minor), 153.65 (major), 89.75 (minor), 82.97 (major), 75.14 (major), 72.80 (minor), 43.44 (minor), 39.93, (major), 31.84 (major), 30.67 (minor), 29.44 (major), 29.04 (major), 28.97 (minor), 26.94 (major), 26.59 (minor), 22.69 (major).

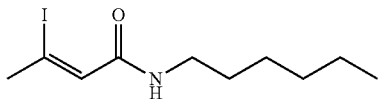

Synthesized by General Protocol C. 86% yield.

$^1$H-NMR (CDCl$_3$, 500 MHz): δ 6.24 (q, 1H. J=1.5 Hz, vinyl CH), 5.73 (bs, 1H, NH), 3.33 (q, 2H, J=6.5 Hz), 2.65 (d, 3H, J=1.5 Hz, allylic CH$_3$), 1.55 (pent, 2H, J=7.0 Hz), 1.38-1.23 (m, 8H), 0.88 (t, 3H, J=7.0 Hz).

4-25

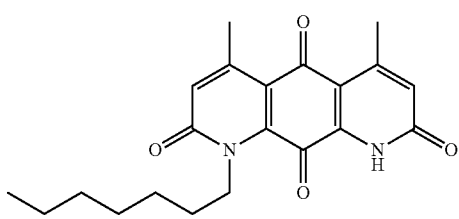

Synthesized by General Protocols D, E, F, and H. 10% yield over 4 steps.

$^1$H-NMR (2:1 CDCl$_3$:CD$_3$OD, 500 MHz): δ 6.76 (q, 1H, J=1.5 Hz, vinyl CH), 6.66 (q, 1H, J=1.0 Hz, vinyl CH), 4.47-4.44 (m, 2H), 2.63 (d, 3H, J=1.0 Hz, allylic CH$_3$), 2.63 (d, 3H, J=1.0 Hz, allylic CH$_3$), 1.77 (bpent, 2H, J=8.0 Hz), 1.46 (bpent, 2H, J=8.0 Hz), 1.42-1.26 (m, 6H), 0.90 (t, 3H, J=7.0 Hz).

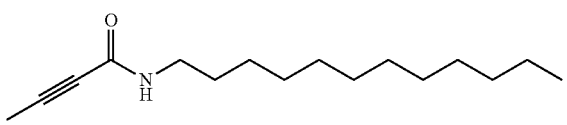 [SMILES: CC#CC(=O)NCCCCCCCCCCCC]

Synthesized by General Protocol A. 72% yield.

$^1$H-NMR (CDCl$_3$, 500 MHz): δ 5.72 (bs, 1H, major rotamer NH), 5.64 (bs, 1H, minor rotamer NH), 3.37 (q, 2H, J=7.0 Hz, minor rotamer NCH$_2$), 3.26 (q, 2H, J=7.0 Hz, major rotamer NCH$_2$), 2.01 (d, 3H, J=1.0 Hz, minor rotamer allylic CH$_3$), 1.93 (d, 3H, J=1.0 Hz, major rotamer allylic CH$_3$), 1.50 (pent, 2H, J=7.0 Hz), 1.34-1.20 (m, 18H), 0.87 (t, 3H, J=7.0 Hz). $^{13}$C-NMR (CDCl$_3$, 125 MHz): δ 153.61 (major), 82.73 (major), 75.05 (major), 43.36 (minor), 39.81 (major), 31.92 (major), 30.55 (minor), 29.66 (major), 29.64 (major), 29.61 (major), 29.56 (major), 29.37 (major), 29.31 (2C, major), 26.90 (major), 26.53 (minor), 22.69 (major), 14.12 (major), 3.95 (minor), 3.62 (major).

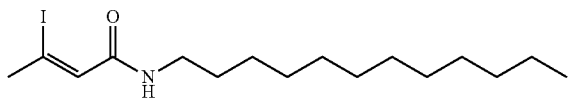 [SMILES: CCCCCCCCCCCCNC(=O)/C=C(/C)I]

Synthesized by General Protocol C. 98% yield.

$^1$H-NMR (CDCl$_3$, 500 MHz): δ 6.22 (q, 1H. J=1.5 Hz, vinyl CH), 5.93 (bs, 1H, NH), 3.29 (q, 2H, J=6.0 Hz), 2.62 (d, 3H, J=1.5 Hz, NCH$_3$), 1.52 (pent, 2H, J=7.5 Hz), 1.35-1.20 (m, 18H), 0.85 (t, 3H, J=7.0 Hz). $^{13}$C-NMR (CDCl$_3$, 125 MHz): δ 164.97, 129.73, 105.42, 39.74, 35.80, 32.07, 29.80, 29.79, 29.74, 29.71, 29.59, 29.50, 29.46, 27.20, 22.84, 14.27.

4-16

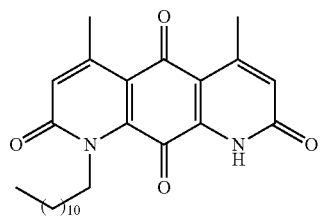

Synthesized by General Protocols D, E, F, and H. 15% yield over 4 steps.

$^1$H-NMR (CDCl$_3$, 500 MHz): δ 10.3 (bs, 1H, NH), 6.75 (d, 1H, J=1.0 Hz, vinyl CH), 6.68 (s, 1H, vinyl CH), 4.48 (t, 2H, J=8.0 Hz, NCH$_2$), 2.61 (d, 3H, J=0.5 Hz, allylic CH$_3$), 2.59 (d, 3H, J=1.0 Hz, allylic CH$_3$), 1.69 (pent, 2H, J=7.5 Hz, NCH$_2$CH$_2$—), 1.42 (pent, 2H, J=7.5 Hz, NCH$_2$CH$_2$CH$_2$—), 1.38-1.18 (m, 16H), 0.86 (t, 3H, J=7.0 Hz, —CH$_2$CH$_3$). $^{13}$C-NMR (CDCl$_3$, 125 MHz): δ 181.78, 175.27, 161.27, 130.99, 151.38, 149.30, 139.13, 137.98, 128.64, 128.40, 119.69, 114.66, 46.50, 32.12, 29.87, 29.85, 29.81, 29.80, 29.55, 29.44, 29.39, 27.14, 23.55, 22.88, 22.44, 14.32. HRMS (ESI-TOF) calcd for C$_{26}$H$_{35}$N$_2$O$_4$(M+H)$^+$: 439.2597. found: 439.2595.

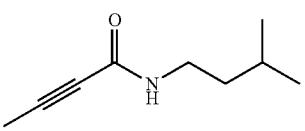

Synthesized by General Protocol A. 73% yield.
HRMS (ESI) calcd for C$_9$H$_{16}$NO (M+H)$^+$: 154.1232. found: 154.1233.

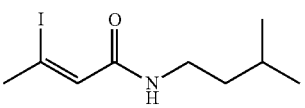

Synthesized by General Protocol C. 95% yield.

$^1$H-NMR (CDCl$_3$, 500 MHz): δ 6.22 (q, 1H, J=1.5 Hz, vinyl CH), 5.82 (bs, 1H, NH), 3.33 (dq, 2H, J=7.5, 1.0 Hz), 2.63 (d, 3H, J=1.5 Hz, allylic CH$_3$), 1.64 (sept, 1H, J=6.5 Hz), 1.43 (q, 2H, J=7.0 Hz), 0.91 (d, 6H, J=6.5 Hz). HRMS (ESI-TOF) calcd for C$_9$H$_{17}$NOI (M+H)$^+$: 282.0355. found: 282.0351.

4-32

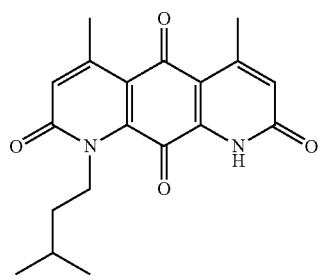

Synthesized by General Protocols D, E, F, and H. 12% yield over 4 steps.

¹H-NMR (2:1 CDCl₃:CD₃OD, 500 MHz): δ 6.76 (q, 1H, J=1.0 Hz, vinyl CH), 6.67 (q, 1H, J=1.5 Hz, vinyl CH), 4.52-4.49 (m, 2H), 2.64 (d, 3H, J=1.0 Hz, allylic CH₃), 2.63 (d, 3H, J=1.0 Hz, allylic CH₃), 1.81 (sept, 1H, J=7.0 Hz, CH), 1.68-1.63 (m, 2H, CH₂CH₂CH), 1.03 (d, 6H, J=6.5 Hz, CH(CH₃)₂). ¹³C-NMR (2:1 CDCl₃:CD₃OD, 125 MHz): δ 181.48, 175.02, 161.83, 161.65, 151.69, 149.89, 139.30, 138.50, 127.42, 127.23, 119.52, 114.77, 45.45, 37.28, 26.49, 22.89, 22.02, 21.83. HRMS (ESI-TOF) calcd for C₁₉H₂₁N₂O₄(M+H)⁺: 341.1501. found: 341.1507.

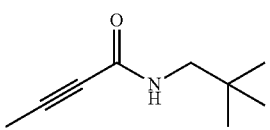

Synthesized by General Protocol A. 25% yield.

¹H-NMR (CDCl₃, 500 MHz): δ 5.75 (bs, 1H, major rotamer NH), 3.17 (d, 2H, J=7.0 Hz, minor rotamer NCH₂), 3.09 (d, 2H, J=6.5 Hz, major rotamer NCH₂), 2.01 (s, 3H, minor rotamer allylic 1.94 (s, 3H, major rotamer allylic CH₃), 0.93 (s, 9H, minor rotamer), 0.92 (s, 9H, major rotamer). HRMS (ESI) calcd for C₉H₁₆NO (M+H)⁺: 154.1232. found: 154.1233.

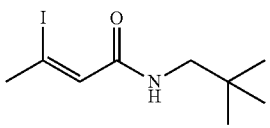

Synthesized by General Protocol C. 96% yield.

¹H-NMR (CDCl₃, 500 MHz): δ 6.29 (q, 1H. J=1.5 Hz, vinyl CH), 5.78 (bs, 1H, NH), 3.16 (d, 2H, J=6.0 Hz), 2.66 (d, 3H, J=1.0 Hz), 0.96 (s, 9H). HRMS (ESI-TOF) calcd for C₉H₁₂NOI (M+H)⁺: 282.0355. found: 282.0354.

4-34

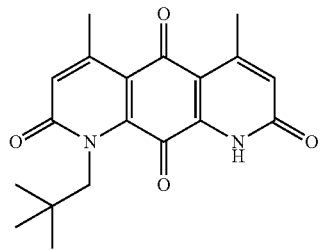

Synthesized by General Protocols D, E, F, and H. 10% yield over 4 steps.

¹H-NMR (2:1 CDCl₃:CD₃OD, 500 MHz): δ 6.75 (d, 1H, J=1.0 Hz, vinyl CH), 6.67 (d, 1H, J=1.0 Hz, vinyl CH), 4.95 (bs, 1H), 4.86 (bs, 1H), 2.64 (s, 6H, allylic CH₃), 0.87 (s, 9H, (CH₃)₃). ¹³C-NMR (CDCl₃, 125 MHz): δ 181.20, 176.32, 162.40, 149.55, 141.41, 139.05, 127.31, 127.19, 119.33, 114.87, 51.10, 34.31, 27.58, 22.80, 21.67. HRMS (ESI-TOF) calcd for C₁₉H₂₁N₂O₄(M+H)⁺: 341.1501. found: 341.1498.

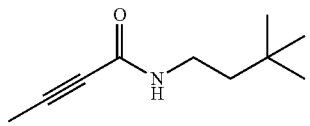

Synthesized by General Protocol A. 76% yield.

¹H-NMR (CDCl₃, 500 MHz): δ 6.00 (bs, 1H, minor rotamer NH), 5.83 (bs, 1H, major rotamer NH), 3.37-3.32 (m, 2H, minor rotamer NCH₂), 3.27-3.23 (m, 2H, major rotamer NCH₂), 1.99 (s, 3H, minor rotamer allylic CH₃), 1.89 (s, 3H, major rotamer allylic CH₃), 1.45-1.42 (m, 2H, minor rotamer), 1.41-1.38 (m, 2H, major rotamer), 0.91 (s, 9H, minor rotamer), 0.89 (s, 9H, major rotamer). HRMS (ESI) calcd for C₁₀H₁₈NO (M+H)⁺: 168.1388. found: 168.1387.

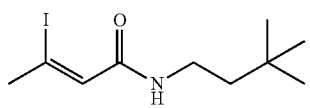

Synthesized by General Protocol C. 93% yield.

¹H-NMR (CDCl₃, 500 MHz): δ 6.20 (q, 1H, J=1.5 Hz, vinyl CH), 5.60 (bs, 1H, NH), 3.37-3.33 (m, 2H), 2.65 (d, 3H, J=1.5 Hz, NCH₃), 1.48-1.45 (m, 2H), 0.94 (s, 9H). HRMS (ESI-TOF) calcd for C₁₀H₁₉NOI (M+H)⁺: 296.0511. found: 296.0513.

4-35

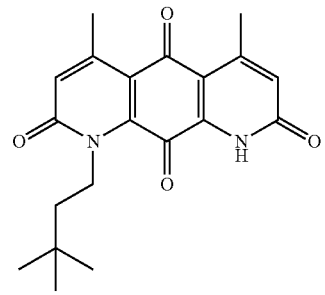

Synthesized by General Protocols D, E, F, and H. 17% yield over 4 steps.

¹H-NMR (2:1 CDCl₃:CD₃OD, 500 MHz): δ 6.75 (d, 1H, J=1.0 Hz, vinyl CH), 6.66 (d, 1H, J=1.0 Hz, vinyl CH), 4.57-4.53 (m, 2H), 2.63 (d, 3H, J=1.0 Hz, allylic CH₃), 2.62 (d, 3H, J=1.0 Hz, allylic CH₃), 1.66 (m, 2H, CH₂CH₂C(CH₃)₃), 1.07 (s, 9H, C(CH₃)₃). ¹³C-NMR (2:1 CDCl₃:CD₃OD, 125 MHz): δ 181.46, 174.98, 161.81, 161.60, 151.64, 149.82, 139.35, 138.45, 127.38, 127.21, 119.53, 114.74, 43.73, 41.45, 29.97, 28.87, 22.88, 21.81. HRMS (ESI-TOF) calcd for C₂₀H₂₃N₂O₄ (M+H)⁺: 355.1658. found: 355.1664.

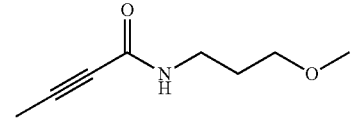

Synthesized by General Protocol A. 65% yield.

¹H-NMR (CDCl₃, 500 MHz): δ 6.27 (bs, 1H, major rotamer NH), 6.02 (bs, 1H, minor rotamer NH), 3.46 (t, 2H, J=6.0

Hz), 3.38 (q, 2H, J=6.5 Hz), 3.34 (s, 3H), 1.92 (s, 3H), 1.77 (pent, 2H, J=6.0 Hz). $^{13}$C-NMR (CDCl$_3$, 125 MHz): δ 156.37 (minor), 153.62 (major), 89.82 (minor), 82.95 (major), 75.00 (major), 72.58 (minor), 71.28 (major), 70.45 (minor), 58.77 (major), 41.34 (minor), 38.04 (major), 30.15 (minor), 28.87 (major), 3.97 (minor), 3.64 (major).

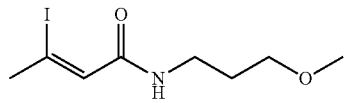

Synthesized by General Protocol C. 96% yield.

$^1$H-NMR (CDCl$_3$, 500 MHz): δ 6.26 (bs, 1H, NH), 6.21 (d, 1H. J=1.0 Hz, vinyl CH), 3.49 (t, 2H, J=6.0 Hz), 3.42 (q, 2H, J=6.5 Hz), 3.34 (s, 3H), 2.64 (d, 3H, J=1.5 Hz), 1.81 (pent, 2H, J=6.0 Hz). $^{13}$C-NMR (CDCl$_3$, 125 MHz): δ 164.90, 129.40, 105.51, 71.65, 58.93, 38.02, 35.78, 29.07.

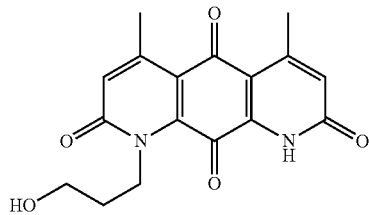 [SMILES: Cc1cc(=O)[nH]c2c1C(=O)c1c(C)cc(=O)n(CCCO)c1C2=O]

Synthesized by General Protocols D, E, G, and H.

$^1$H-NMR (2:1 CDCl$_3$:CD$_3$OD, 500 MHz): δ 6.76 (d, 1H, J=1.0 Hz, vinyl CH), 6.65 (d, 1H, J=1.0 Hz, vinyl CH), 4.58 (t, 2H, J=7.5 Hz), 3.70 (t, 2H, J=6.0 Hz), 2.63 (d, 3H, J=1.0 Hz, allylic CH$_3$), 2.63 (d, 3H, J=1.0 Hz, allylic CH$_3$), 2.06-2.01 (m, 2H). HRMS (ESI-TOF) calcd for C$_{12}$H$_{12}$N$_2$O$_5$ (M+H)$^+$: 329.1137. found: 329.1129.

Molecular Modeling of DNQ in NQO1.

DNQ (or derivative) was built and a 10 Å water layer was built around the molecule. The DNQ structure was then energy minimized using MOE with a MMFF94x forcefield using gas phase calculations and a cutoff of 0.01. Charges were then fixed using an MMFF94 forcefield. The NQO1 structure was downloaded from the PDB (2F1O). One of the homodimers was extracted and protonated. DNQ was then modeled into the protein active site, using the site of dicoumarol to identify the active site. It was docked using the Dock program in MOE which uses Triangle Matching for the placement of the small molecule and London dG for rescoring of the placement of the small molecule. The top 30 configurations were then visually inspected to ensure that the molecule was within the active site and pi stacking with the FAD molecule. Using LigX, the best configuration was protonated and the energy was minimized to obtain the calculated binding energies.

Example 5

Inhibition of Breast Cancer Cells

Figure 12:
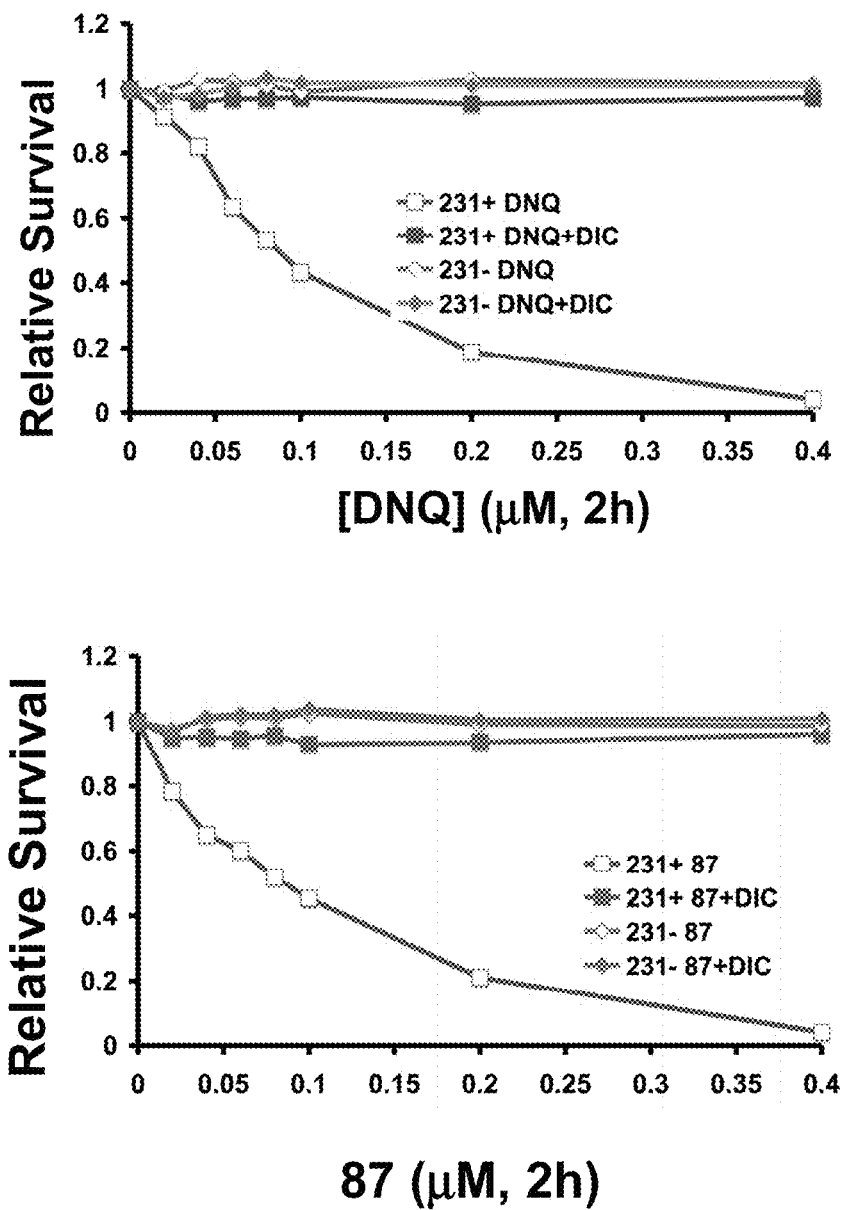
FIG. 12. Efficacy of DNQ and compound 87 vs. the MDA-MB-231 (breast cancer) cell line that expresses NQO1, the version that does not express NQO1, and both these cell lines where NQO1 is inhibited by dicumoral.

FIG. 12 illustrates an embodiment of the efficacy of DNQ and compound 87 vs. the MDA-MB-231 (breast cancer) cell line that expresses NQO1, the version that does not express NQO1, and both these cell lines where NQO1 is inhibited by dicumoral.

Example 6

DNQ Derivative PAR-PARP1 Formation in LLC Tumors In Vivo

Immunoblotting and Antibodies:

Antibodies that specifically detect poly(ADP-ribosyl)ated α-PAR (BD Pharmingen, San Jose, Calif.) proteins (e.g., the most abundant species, poly(ADP-ribosyl)ated PARP1, PAR-PARP1) and α-PARP1 (sc-8007, Santa Cruz Biotechnology) antibodies were used at 1:4000 and 1:2000 dilutions, respectively. α-Tubulin was monitored for loading.

PARP1 Hyperactivation In Vivo Using the Orthotopic Lewis Lung Carcinoma (LLC) Model:

To generate a known control to monitor the formation of poly(ADP-ribose)ylated-polymerase 1 (PAR-PARP1) in cells, LLC tumor cells were treated in vitro with hydrogen peroxide (H$_2$O$_2$, 0.5 μM) for 15 minutes, and whole cell protein lysates were separated by SDS-PAGE using the α-PAR (BD Pharmingen, San Jose, Calif.) antibody described above. PAR-PARP1 formation was then assessed by immunoblot analyses as previously described in Huang et al., *Cancer Research*, 2012.

Figure 13:
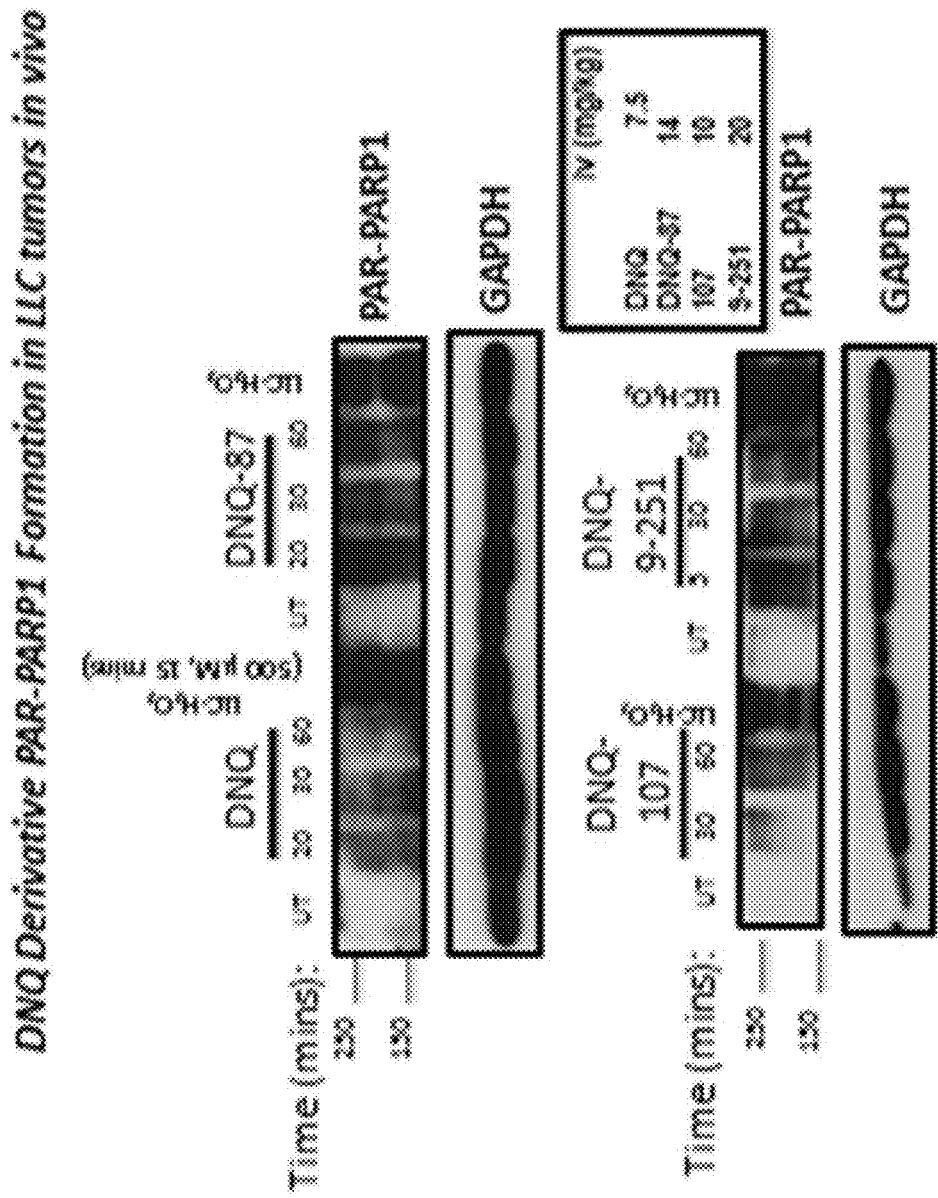
FIG. 13. Immunoblotting analyses of DNQ-87, DNQ-107 and DNQ-9-251, as described in Example 6, according to one embodiment.

LLC cells (1.0×10$^6$) were intravenously (iv) injected into the tail veins of female 18-20 gram NOD/SCID mice. Establishment of tumor nodules in the lungs of exposed mice were confirmed by bioluminescence and mice (5/group) were treated intravenously (via tail vein injection) with: (i) hydroxypropyl-beta-cyclodextrin (HPβCD) vehicle alone; (ii) DNQ (7.5 mg/kg); (ii) DNQ-87 (14 mg/kg); (iii) DNQ-107 (10 mg/kg); or (vi) DNQ 9-251 (20 mg/kg) dissolved in HPβCD. At specific times indicated (in mins) after injection of vehicle or drug, mice were euthanized, lungs removed and tumor nodules harvested. Whole cell extracts were prepared from tumor tissue and formation of PAR-PARP1 was evaluated by immunoblotting analyses. Extracts from cells treated with H$_2$O$_2$ were used as controls for monitoring PAR-PARP1 formation in LLC tumor cells. FIG. 13 shows the immunoblotting analyses of DNQ-87, DNQ-107 and DNQ-9-251.

Results:

Using an orthotopic LLC model in female NOD/SCID mice, PARP1 hyperactivation in vivo was monitored by the formation of PAR-PARP1 after exposure to DNQ DNQ-87, DNQ-107, or DNQ 9-251. Each DNQ drug was used at or near their maximum tolerated doses (MTD5). Analyses of tumor tissue from exposed mice revealed the formation of PAR-PARP1 following treatment with DNQ while tumors treated with vehicle alone did not display PARP1 hyperactivation. Additionally, the treatment of tumor-bearing animals with DNQ-87, DNQ-107 or DNQ 9-251 not only resulted in formation of PAR-PARP1, but higher levels of PAR-PARP1 formation were noted than in mice treated with DNQ.

In vitro, DNQ-87 was also an efficient inducer of specific types of DNA damage. Like DNQ and β-lapachone, DNQ-87 caused extensive initial DNA single strand damage and base lesions as measured by alkaline comet assays (data not shown). In contrast, DNA double strand break (DSB) formation was delayed (appearing 15-30 mins after initial DNA SSBs and base lesions), because DNQ-87-exposed cells demonstrated increases in nuclear staining of phosphorylated (Ser-1981) ATM, γ-H2AX and phosphorylated DNA-PKcs proteins that are hallmarks of exposed DSBs (data not shown). Thus, DNQ-87, like DNQ and β-lapachone, are efficient DNA base and SSB lesions formation, with delayed formation of DSBs most likely due to DNA replication.

Example 7

Preparation of DNQ Compounds

Various DNQ compounds, such as DNQ-P1, DNQ-P2, DNQ-P3, DNQ-P4, and various other derivatives, can be prepared by the methods illustrated in Schemes 7.1 to 7.4. The compounds can be isolated as either the phosphoric acids or, for example, as the corresponding sodium salts. The phosphate compounds can have significantly higher aqueous solubility then the corresponding alkyl compounds.

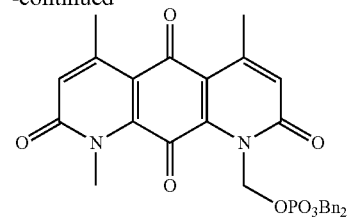

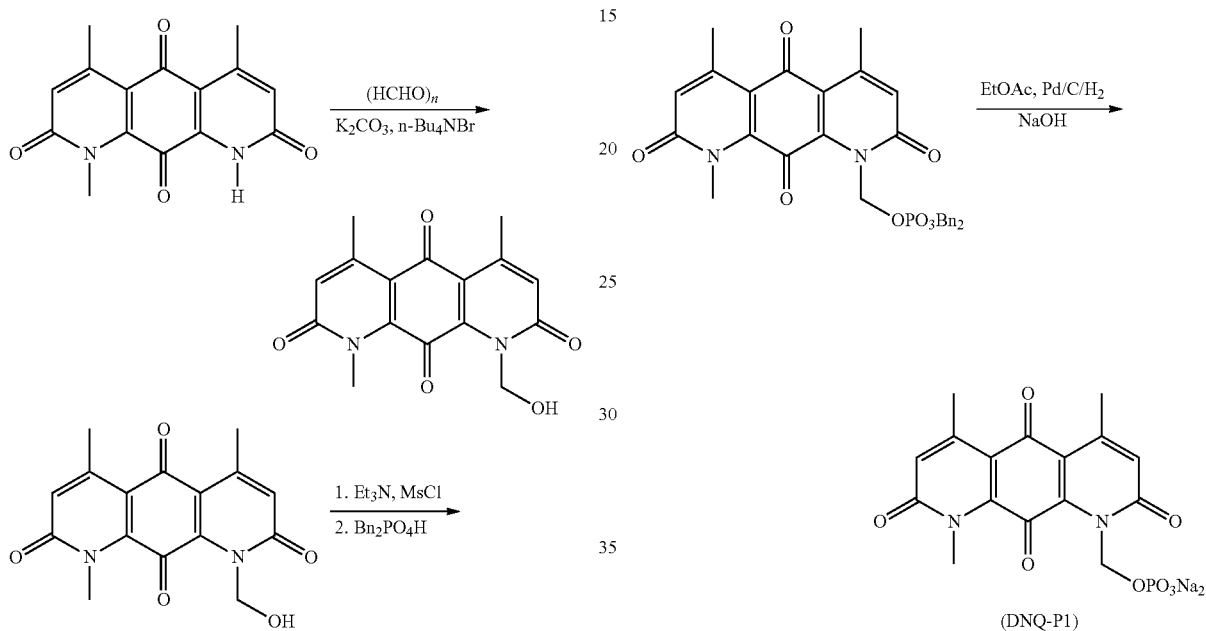

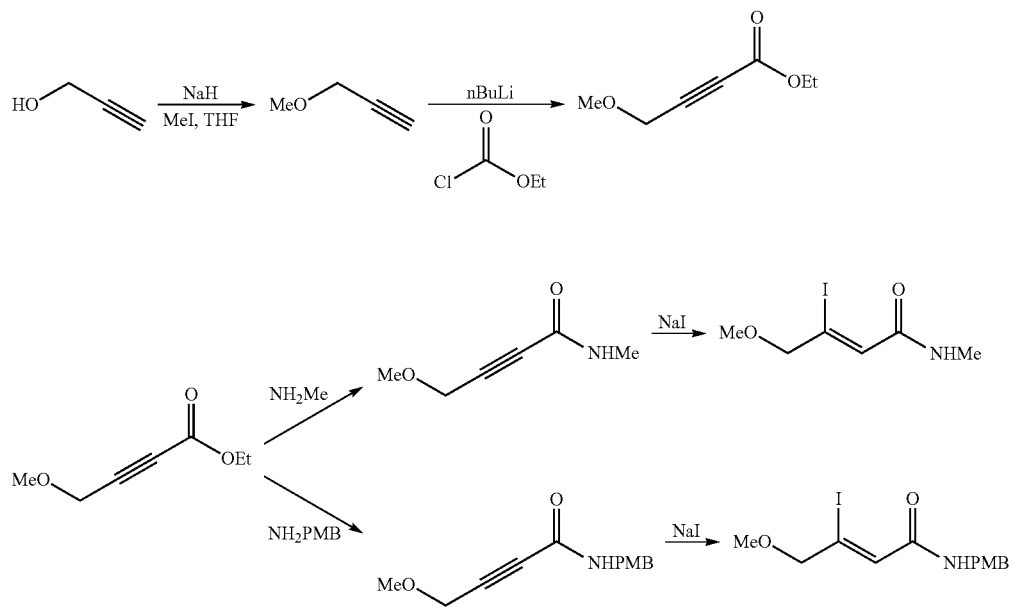

Cross coupling, ring closure, deprotection with HBr and oxidation can then be carried out as shown in Scheme 1.14 and/or as described in Example 4 to provide DNQ-6.2a or DNQ-6.2b, which can then be modified to provide DNQ-P2 or DNQ-P3, respectively, as shown in Scheme 7.3.
Scheme 7.3. Preparation of DNQ-P2 and DNQ-P3.
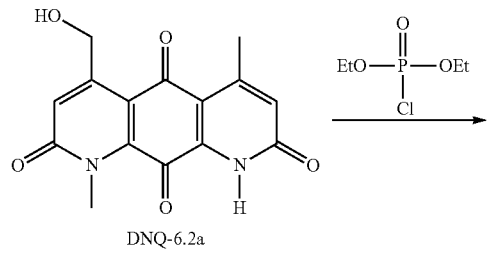
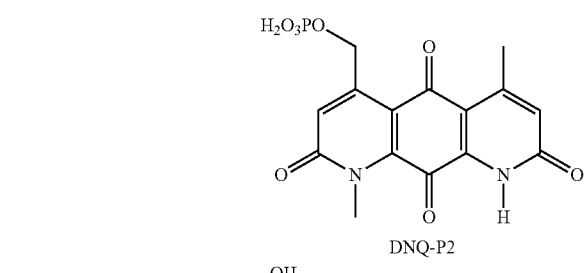
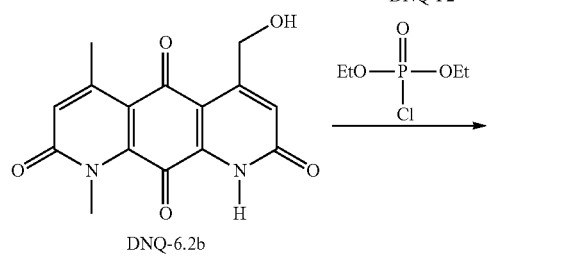
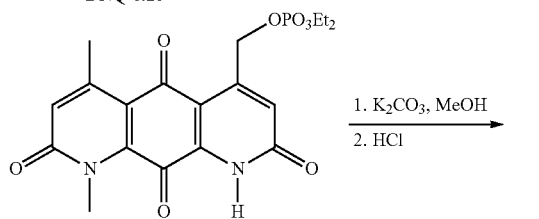
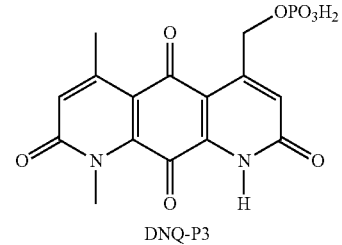
Scheme 7.4. Preparation of DNQ-P4.
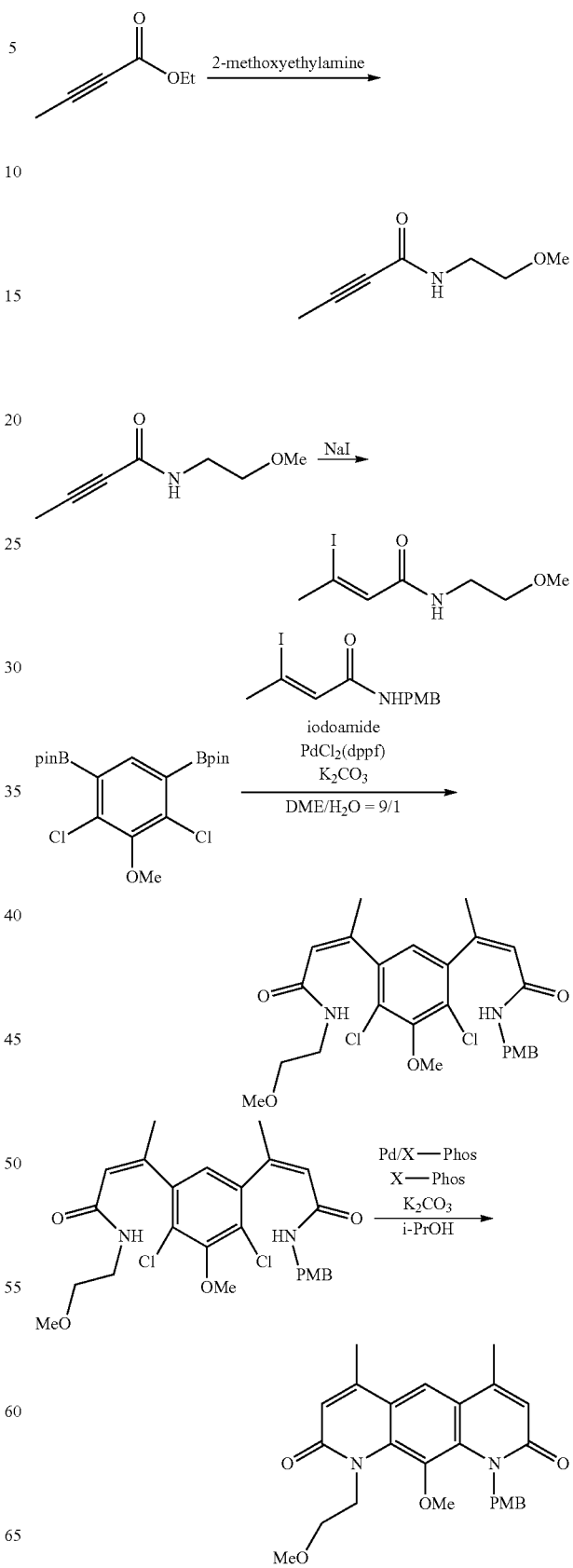

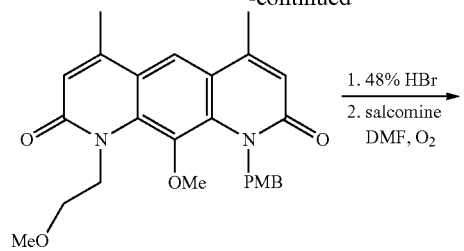

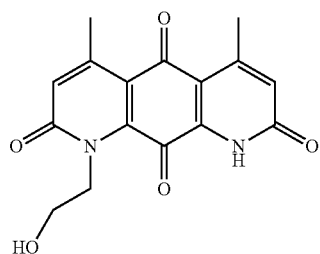

The final intermediate of Scheme 7.4 can be converted to DNQ-P4 by a route similar to that employed in Scheme 7.3 to provide the phosphorylated product, which can be readily isolated as a sodium salt.

Example 8

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 10.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 210.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |

-continued

| (ix) Topical Ointment | wt. % |
|---|---|
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be recognized by one of skill in the art, methods and devices useful for the present methods can include a large number of optional composition and processing elements and steps.

Although the present invention has been described with reference to certain embodiments thereof, other embodiments are possible without departing from the present invention. Although the description herein contains a plurality of specificities, these should not be construed as limiting the scope of the invention but as merely providing illustrations of some of the presently preferred embodiments of the invention. The spirit and scope of the appended claims should not be limited, therefore, to the description of any specific embodiments contained herein. All embodiments that come within the meaning of the claims, either literally or by equivalence are intended to be embraced therein. Furthermore, the advantages described above are not necessarily the only advantages of the invention, and it is not necessarily expected that all of the described advantages will be achieved with every embodiment of the invention.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference). References cited herein are incorporated by reference to indicate the state of the art as of their publication or filing date and it is intended that this information can be employed herein, if needed, to exclude specific embodiments that are in the prior art. For example, when compounds are claimed generically, it should be understood that compounds known and available in the art prior to Applicant's invention, including compounds for which an enabling disclosure is provided in the references cited herein, are not intended to be included in the compounds claims herein.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims.

What is claimed is:

1. A compound of the Formula (I):

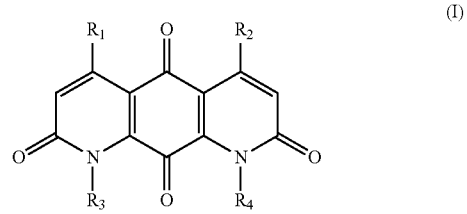

wherein
$R_1$ is alkyl;
$R_3$ is H;
$R_2$ and $R_4$ are each independently —X—R;
each X is independently a direct bond or a bridging group, wherein the bridging group is —O—, —S—, —NH—, —C(═O)—, —O—C(═O)—, —C(═O)—O—, —O—C(═O)—O—, or a linker of the formula —W-A-W—, wherein
each W is independently —N(R')C(═O)—, —C(═O) N(R)—, —OC(═O)—, —C(═O)O—, —O—, —S—, —S(O)—, —S(O)$_2$—, —N(R')—, —C(═O)—, —(CH$_2$)$_n$— where n is 1-10, or a direct bond, wherein each R' is independently H, (C1-C6) alkyl, or a nitrogen protecting group; and each A is independently $(C_1-C_{20})$alkyl, $(C_2-C_{16})$alkenyl, $(C_2-C_{16})$alkynyl, $(C_3-C_8)$cycloalkyl, $(C_6-C_{10})$aryl, —$(OCH_2—CH_2)_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or $(C_1-C_{20})$alkyl, $(C_2-C_{16})$alkenyl, $(C_2-C_{16})$alkynyl, or —$(OCH_2—CH_2)_n$— interrupted between two carbons, or between a carbon and an oxygen, with a cycloalkyl, heterocycle, or aryl group;

each R is independently alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^y$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;

wherein any alkyl or aryl can be optionally substituted with one or more hydroxy, amino, cyano, nitro, or halo groups;

or a salt or solvate thereof;

provided that when R$_1$, R$_2$, and R$_4$ are methyl, R$_3$ is not H or methyl.

2. The compound of claim 1 wherein R$_4$ is a (C$_{1-20}$)alkyl group.

3. The compound of claim 1 wherein R$_1$ is a branched (C$_{1-20}$)alkyl group.

4. The compound of claim 1 wherein R$_2$ is a (C$_{1-20}$)alkyl group.

5. The compound of claim 1 wherein R$_1$ is a straight chain (C$_{1-20}$)alkyl group.

6. The compound of claim 1 wherein R$_4$ is a (C$_{1-20}$)alkyl group.

7. The compound of claim 1 wherein R$_1$ is methyl.

8. The compound of claim 1 wherein R$_2$ is methyl.

9. The compound of claim 1 wherein R$_1$ and R$_2$ are both methyl.

10. The compound of claim 1 wherein R$_4$ is methyl.

11. A compound of Formula (I):

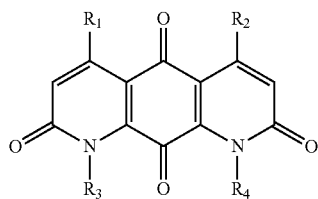

(I)

wherein

R$_1$ and R$_2$ are methyl; R$_3$ is hydrogen; and R$_4$ is 2-methyl-propane;

R$_1$ and R$_2$ are methyl; R$_3$ is hydrogen; and R$_4$ is butyl;

R$_1$ and R$_4$ are methyl and R$_3$ is hydrogen; and R$_2$ is ethyl;

R$_1$ and R$_2$ are methyl and R$_3$ is hydrogen; and R$_4$ is ethyl;

R$_1$ is methyl; R$_3$ is hydrogen; R$_2$ is propyl; and R$_4$ is butyl;

R$_1$ and R$_4$ are methyl; R$_2$ is propyl and R$_3$ is hydrogen;

R$_1$ is propyl; R$_2$ and R$_4$ are methyl and R$_3$ is hydrogen;

R$_1$ and R$_2$ are ethyl; R$_3$ is hydrogen; and R$_4$ is methyl;

R$_1$ is propyl; R$_2$ is methyl; R$_3$ is hydrogen; and R$_4$ is butyl;

R$_1$ and R$_2$ are propyl; R$_3$ is hydrogen; and R$_4$ is butyl;

R$_1$ and R$_2$ are methyl; R$_3$ is hydrogen; and R$_4$ is C$_{12}$alkyl;

R$_1$ and R$_2$ are methyl; R$_3$ is hydrogen; and R$_4$ is tert-butyl;

R$_1$ and R$_2$ are methyl; R$_3$ is hydrogen; and R$_4$ is hydroxypropyl;

R$_1$ and R$_2$ are methyl; R$_3$ is hydrogen; and R$_4$ is 3,3-dimethylbutyl [—CH$_2$CH$_2$C(CH$_3$)$_2$CH$_3$];

R$_1$ and R$_2$ are methyl; R$_3$ is hydrogen; and R$_4$ is 3-methybutyl [—CH$_2$CH$_2$CH(CH$_3$)CH$_3$];

R$_2$ and R$_4$ are methyl; R$_3$ is hydrogen; and R$_1$ is ethyl;

R$_1$ and R$_2$ are methyl; R$_3$ is hydrogen; and R$_4$ is propyl;

R$_1$ and R$_2$ are methyl; R$_3$ is hydrogen; and R$_4$ is n-pentyl;

R$_1$ and R$_2$ are methyl; R$_3$ is hydrogen; and R$_4$ is n-hexyl;

R$_1$ and R$_2$ are methyl; R$_3$ is hydrogen; and R$_4$ is isopropyl;

R$_1$ and R$_2$ are methyl; R$_3$ is hydrogen; and R$_4$ is cyclooctyl;

R$_1$ and R$_2$ are methyl; R$_3$ is hydrogen; and R$_4$ is cyclopropyl;

R$_1$ and R$_2$ are methyl; R$_3$ is hydrogen; and R$_4$ is methylcyclopropyl;

R$_1$ and R$_2$ are methyl; R$_3$ is hydrogen; and R$_4$ is ethylcyclopropyl;

R$_2$ and R$_4$ are methyl; R$_3$ is hydrogen; and R$_1$ is C$_{12}$alkyl;

R$_1$ and R$_4$ are methyl; R$_3$ is hydrogen; and R$_2$ is C$_{12}$alkyl;

R$_2$ is —CH$_2$OPO$_3$Na$_2$; R$_1$ and R$_4$ are methyl; and R$_3$ is hydrogen;

R$_2$ and R$_4$ are methyl; R$_1$ is —CH$_2$OPO$_3$Na$_2$; and R$_3$ is hydrogen;

R$_1$ and R$_2$ are methyl; R$_4$ is —CH$_2$OPO$_3$Na$_2$; and R$_3$ is hydrogen;

R$_1$ and R$_2$ are methyl; R$_4$ is —CH$_2$CH$_2$OPO$_3$Na$_2$; and R$_3$ is hydrogen;

R$_2$ is —CH$_2$OH; R$_1$ and R$_4$ are methyl; and R$_3$ is hydrogen;

R$_2$ and R$_4$ are methyl; R$_1$ is —CH$_2$OH; and R$_3$ is hydrogen;

R$_1$ and R$_2$ are methyl; R$_4$ is —CH$_2$OH; and R$_3$ is hydrogen; or

R$_1$ and R$_2$ are methyl; R$_4$ is —CH$_2$CH$_2$OH; and R$_3$ is hydrogen.

12. A pharmaceutical composition comprising a compound of claim 1 and a pharmaceutically acceptable carrier.

13. A composition comprising a compound of claim 1 and hydroxypropyl-β-cyclodextrin (HPβCD).

14. A method of treating cancer characterized by tumor cells with elevated NQO1 levels comprising:

administering to a patient affected by such cancer a therapeutically effective amount of a compound of Formula (I):

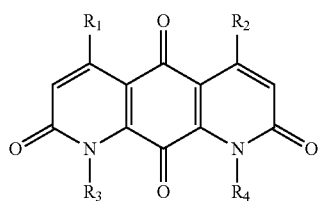

(I)

$R_1$, $R_2$, $R_3$, and $R_4$ are each independently —H or —X—R;

each X is independently a direct bond or a bridging group, wherein the bridging group is —O—, —S—, —NH—, —C(=O)—, —O—C(=O)—, —C(=O)—O—, —O—C(=O)—O—, or a linker of the formula —W-A-W—, wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-10, or a direct bond, wherein each R' is independently H, (C1-C6)alkyl, or a nitrogen protecting group; and each A is independently (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a cycloalkyl, heterocycle, or aryl group;

each R is independently alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^3$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;

wherein any alkyl or aryl can be optionally substituted with one or more hydroxy, amino, cyano, nitro, or halo groups; or a salt or solvate thereof;

provided that when $R_1$, $R_2$, and $R_3$ are methyl, $R_4$ is not H or methyl;

wherein the cancer cells are treated, killed, or inhibited from growing.

15. The method of claim 14 wherein the cancer cells are malignant.

16. The method of claim 15 wherein the malignant cancer cells are Non-Small-Cell Lung Carcinoma.

17. A method of treating a cancer cell having an elevated NQO1 level comprising:

exposing the cancer cell to a therapeutically effective amount of a compound of claim 1, wherein the cancer cell is treated, killed, or inhibited from growing.

18. The method of claim 14 wherein the cancer cells are in the form of a solid tumor.

19. A compound of the Formula (I):

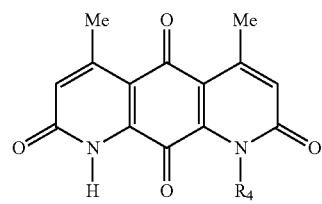

(I)

wherein $R_4$ is —X—R;

X is a bridging group, wherein the bridging group is —C(=O)—, —C(=O)—O—, or a linker of the formula —W-A-W—, wherein each W is independently —N(R')C(=O)—, —C(=O)N(R')—, —C(=O)O—, —S(O)—, —S(O)$_2$—, —N(R')—, —C(=O)—, —(CH$_2$)$_n$— where n is 1-10, or a direct bond, wherein each R' is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$— wherein n is 1 to about 6, —OP(O)(OH)O—, —OP(O)(OH)O(CH$_2$)$_n$— wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a cycloalkyl, heterocycle, or aryl group;

R is alkyl, alkenyl, alkynyl, heteroalkyl, cycloalkyl, cycloalkenyl, heterocycloalkyl, heterocycloalkenyl, (cycloalkyl)alkyl, (heterocycloalkyl)alkyl, (cycloalkyl)heteroalkyl, (heterocycloalkyl)heteroalkyl, aryl, heteroaryl, (aryl)alkyl, (heteroaryl)alkyl, hydrogen, hydroxy, hydroxyalkyl, alkoxy, (alkoxy)alkyl, alkenyloxy, alkynyloxy, (cycloalkyl)alkoxy, heterocycloalkyloxy, amino, alkylamino, aminoalkyl, acylamino, arylamino, sulfonylamino, sulfinylamino, —COR$^x$, —COOR$^x$, —CONHR$^x$, —NHCOR$^x$, —NHCOOR$^x$, —NHCONHR$^x$, —N$_3$, —CN, —NC, —NCO, —NO$_2$, —SH, -halo, alkoxycarbonyl, alkylaminocarbonyl, sulfonate, sulfonic acid, alkylsulfonyl, alkylsulfinyl, arylsulfonyl, arylsulfinyl, aminosulfonyl, R$^x$S(O)R$^y$—, R$^x$S(O)$_2$R$^y$—, R$^x$C(O)N(R$^x$)R$^y$—, R$^x$SO$_2$N(R$^x$)R$^y$—, R$^x$N(R$^x$)C(O)R$^y$—, R$^x$N(R$^x$)SO$_2$R$^y$—, R$^x$N(R$^x$)C(O)N(R$^x$)R$^y$—, carboxaldehyde, acyl, acyloxy, —OPO$_3$H$_2$, —OPO$_3$Z$_2$ where Z is an inorganic cation, or saccharide; where each R$^x$ is independently H, OH, alkyl or aryl, and each R$^y$ is independently a group W;

wherein any alkyl or aryl can be optionally substituted with one or more hydroxy, amino, cyano, nitro, or halo groups;

or a salt or solvate thereof.

20. The compound of claim 19 wherein the compound is:
(4-31)
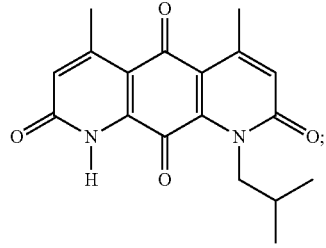
(9-253)
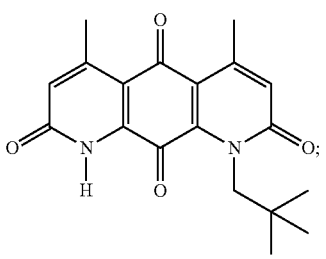
(9-251)
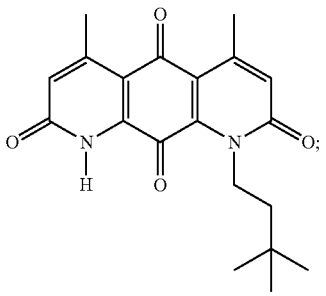
(10-41)
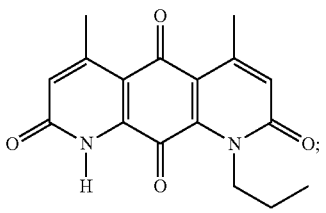
(109)
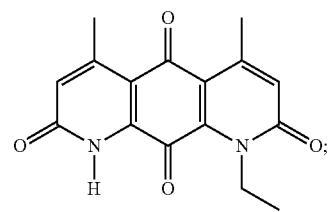
-continued
(9-281)
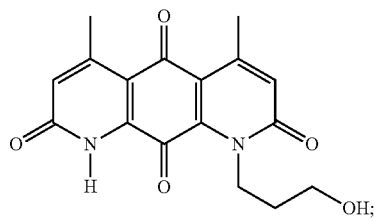
(9-249)
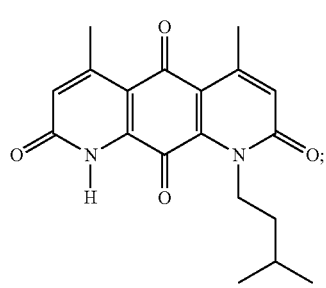
(9-255)
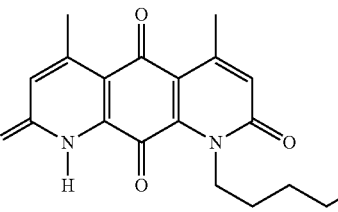
(9-257)
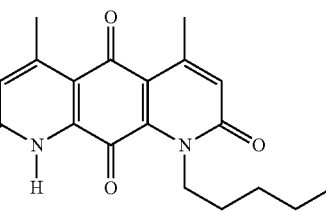
or a salt or solvate thereof.
* * * * *

UNITED STATES PATENT AND TRADEMARK OFFICE
CERTIFICATE OF CORRECTION

Page 1 of 1

PATENT NO.           : 9,233,960 B2
APPLICATION NO.      : 14/351861
DATED                : January 12, 2016
INVENTOR(S)          : Paul J. Hergenrother et al.

It is certified that error appears in the above-identified patent and that said Letters Patent is hereby corrected as shown below:

Claims

Claim 1, at column 96, lines 64-65:
delete "-C(=O)N(R)-," and insert -- C(=O)N(R')-, -- therefor.

Claim 14, at column 99, line 48:
delete "$R^xS(O)R^3$-," and insert -- $R^xS(O)R^y$-, -- therefor.

Signed and Sealed this
Third Day of May, 2016

Michelle K. Lee
*Director of the United States Patent and Trademark Office*